(12) United States Patent
Panchapakesan et al.

(10) Patent No.: US 11,002,737 B2
(45) Date of Patent: May 11, 2021

(54) MICRO-ARRAY DEVICES FOR CAPTURING CELLS IN BLOOD AND METHODS OF THEIR USE

(71) Applicants: Worcester Polytechnic Institute, Worcester, MA (US); University of Louisville Research Foundation, Inc., Louisville, KY (US)

(72) Inventors: Balaji Panchapakesan, Worcester, MA (US); Farhad Khosravi, Worcester, MA (US); Shesh N. Rai, Louisville, KY (US)

(73) Assignees: Worcester Polytechnic Institute, Worcester, MA (US); University of Louisville Research Foundation, Inc., Louisville, KY (US)

( * ) Notice: Subject to any disclaimer, the term of this patent is extended or adjusted under 35 U.S.C. 154(b) by 336 days.

(21) Appl. No.: 15/718,692

(22) Filed: Sep. 28, 2017

(65) Prior Publication Data
US 2018/0088117 A1 Mar. 29, 2018

Related U.S. Application Data

(60) Provisional application No. 62/401,394, filed on Sep. 29, 2016.

(51) Int. Cl.
| | |
|---|---|
| *G01N 33/574* | (2006.01) |
| *G01N 15/10* | (2006.01) |
| *G01N 27/12* | (2006.01) |
| *G01N 15/00* | (2006.01) |

(52) U.S. Cl.
CPC ....... *G01N 33/574* (2013.01); *G01N 15/1031* (2013.01); *G01N 15/1056* (2013.01); *G01N 27/125* (2013.01); *G01N 33/5748* (2013.01); *G01N 33/57415* (2013.01); *G01N 33/57492* (2013.01); *G01N 27/127* (2013.01); *G01N 2015/0065* (2013.01); *G01N 2015/1006* (2013.01); *G01N 2015/1062* (2013.01); *G01N 2333/705* (2013.01); *G01N 2333/71* (2013.01)

(58) Field of Classification Search
None
See application file for complete search history.

(56) References Cited

U.S. PATENT DOCUMENTS

| | | | | |
|---|---|---|---|---|
| 5,994,071 | A * | 11/1999 | Ross | C12Q 1/6886 435/6.14 |
| 8,318,308 | B2 | 11/2012 | Hata et al. | |
| 9,068,923 | B2 | 6/2015 | Yao | |
| 10,378,044 | B1 * | 8/2019 | Erramilli | C12Q 1/6837 |
| 2002/0193327 | A1 * | 12/2002 | Nemerow | A61P 9/10 514/44 R |
| 2003/0186920 | A1 * | 10/2003 | Sirois | C12N 15/1138 514/44 A |
| 2006/0076249 | A1 * | 4/2006 | Meisegeier | G01N 33/5438 205/792 |
| 2006/0275914 | A1 * | 12/2006 | Henley | B82Y 30/00 436/171 |
| 2009/0017553 | A1 * | 1/2009 | Hoying | G01N 21/6428 436/172 |
| 2010/0009394 | A1 * | 1/2010 | Guo | G01N 33/54306 435/7.94 |
| 2011/0224091 | A1 * | 9/2011 | Panchapakesan | G01N 27/4145 506/9 |
| 2013/0057251 | A1 * | 3/2013 | Ahn | G01N 27/4146 324/76.11 |
| 2016/0238553 | A1 | 8/2016 | Shachar | |
| 2017/0045508 | A1 * | 2/2017 | Khattak | B01L 3/523 |
| 2017/0067889 | A1 * | 3/2017 | Tamir | G01N 27/4145 |
| 2018/0372678 | A1 * | 12/2018 | Patolsky | A61B 5/6847 |

OTHER PUBLICATIONS

Khosravi et al. "Ultrasensitive Label-Free Sensing of IL-6 Based on PASE Functionalized Carbon Nanotube Micro-Arrays with RNA-Aptamers as Molecular Recognition Elements," Biosensors, Apr. 17, 2017 (Apr. 17, 2017), vol. 7, Iss. 2, pp. 1-13.
Kim et al., "Langmuir-Blodgett Films of Single-Wall Carbon Nanotubes: Layer-by-layer Deposition and In-plane Orientation of Tubes," Japanese Journal of Applied Sciences, Dec. 10, 2003 (Dec. 10, 2003), vol. 42. Pt. 1, No. 12, pp. 7629-7634.
King et al., "Electrical Detection of Specific Versus Non-Specific Binding Events in Breast Cancer Cells," Proceedings of SPIE—the International Society for Optical Engineering, Oct. 10, 2012 (Oct. 10, 2012), vol. 8460, pp. 1-16.
Qi et al., "Toward Large Arrays of Multiplex Functionalized Carbon Nanotube Sensors for Highly Sensitive and Selective Molecular Detection," Nano Letters, Feb. 6, 2003 (Feb. 6, 2003), vol. 3, Issue 3, pp. 347-351.
International Search Report in International Patent Application No. PCT/US2017/054278 dated Dec. 22, 2017.
Khosravi et al., "Nanotube devices for digital profiling of cancer biomarkers and circulating tumor cells," The 7th IEEE International Conference on Nano/Molecular Medicine and Engineering, IEEE, Nov. 10, 2013 (Nov. 10, 2013), pp. 107-112.
Khosravi et al., "Nanotube Devices for Digital Profiling: A focus on cancer biomarkers and circulating tumor cells," IEEE Nanotechnology Magazine, IEEE, USA, Dec. 1, 2013 (Dec. 1, 2013), vol. 7, No. 4, pp. 20-26.
Rai et al., "Classification of biosensor time series using dynamic time warping: applications in screening cancer cells with characteristic biomarkers," Open Access Medical Statistics, Jun. 1, 2016 (Jun. 1, 2016), pp. 21-29.

* cited by examiner

Primary Examiner — Ann Y Lam
(74) Attorney, Agent, or Firm — Greenberg Traurig, LLP; Roman Fayerberg

(57) ABSTRACT

The present disclosure provides micro-array devices for capturing cells in blood and methods of their use. In some aspects, a method for counting cells in a blood sample is provided, the method comprising applying a blood sample onto a CNT device; allowing cells in the blood sample to differentially settle on the CNT device, and identifying and counting cells of preselected type in the blood sample.

14 Claims, 64 Drawing Sheets

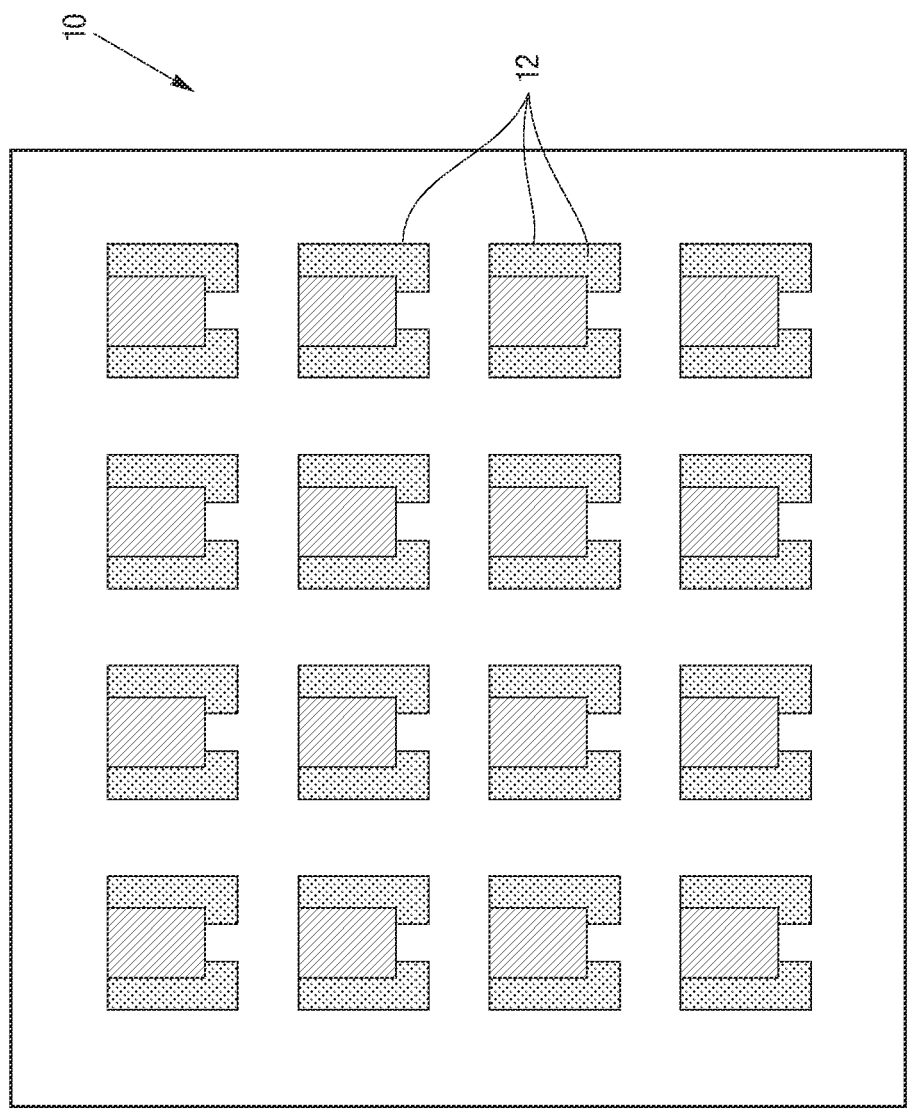

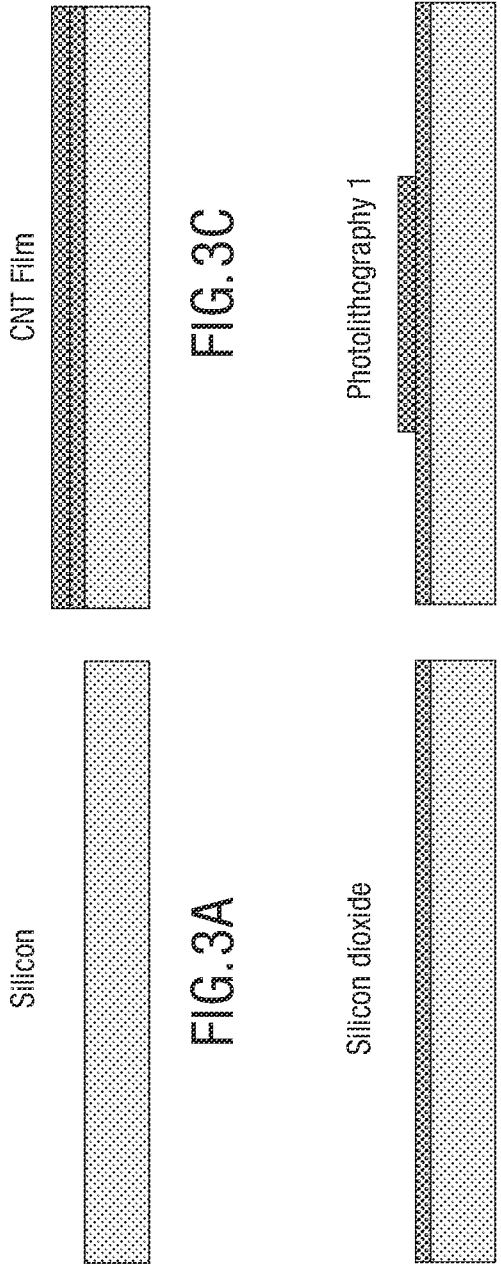

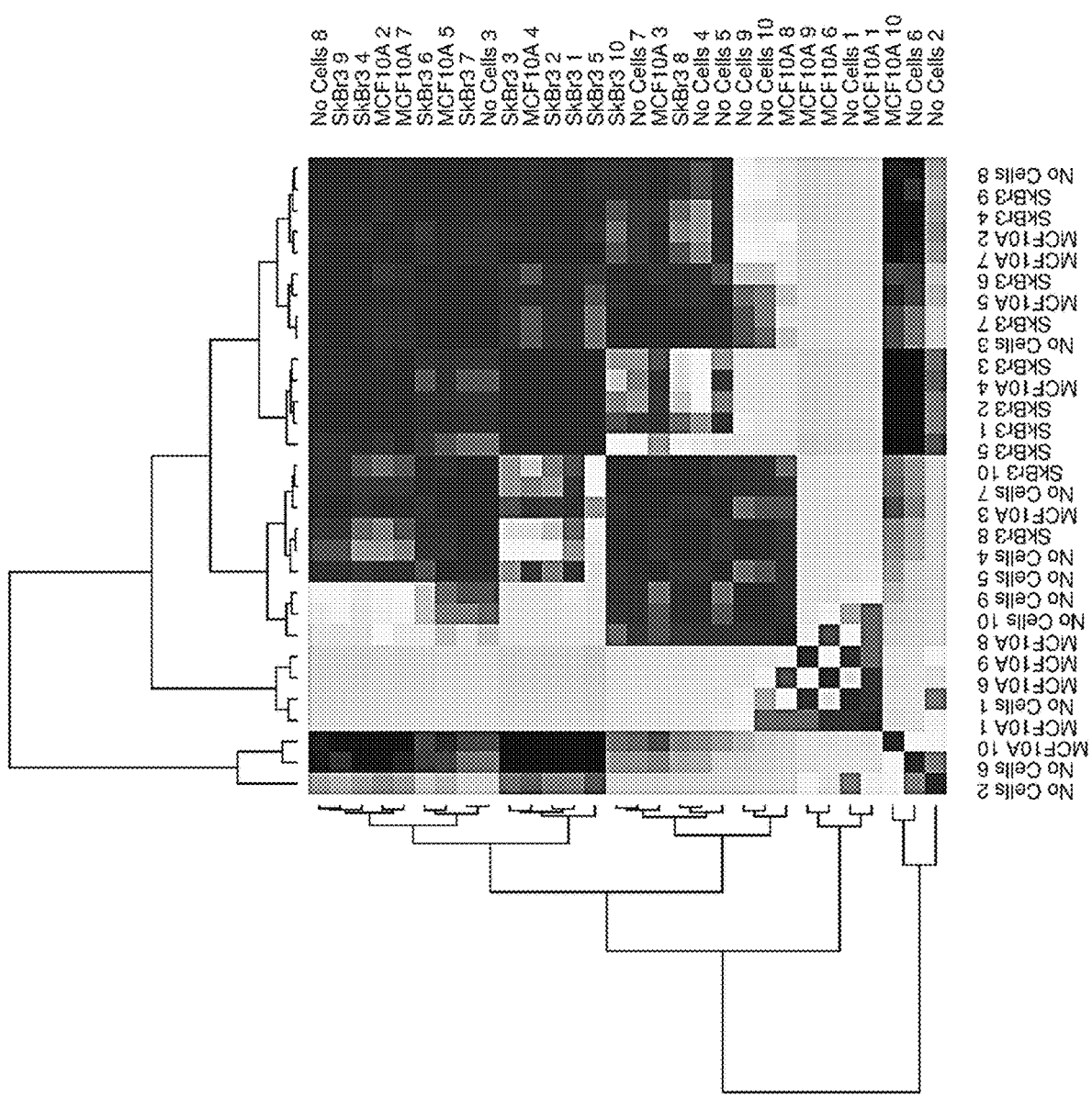

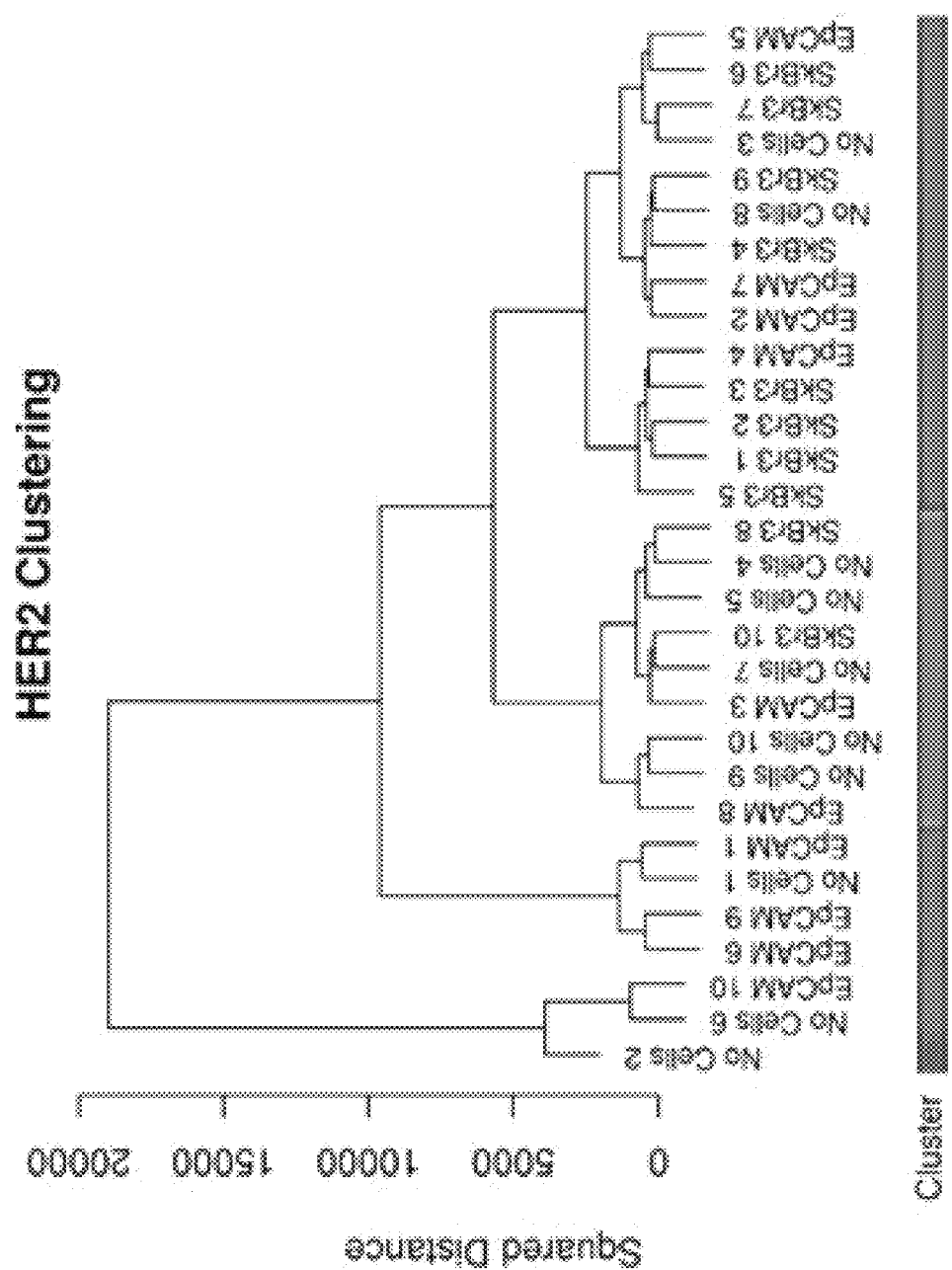

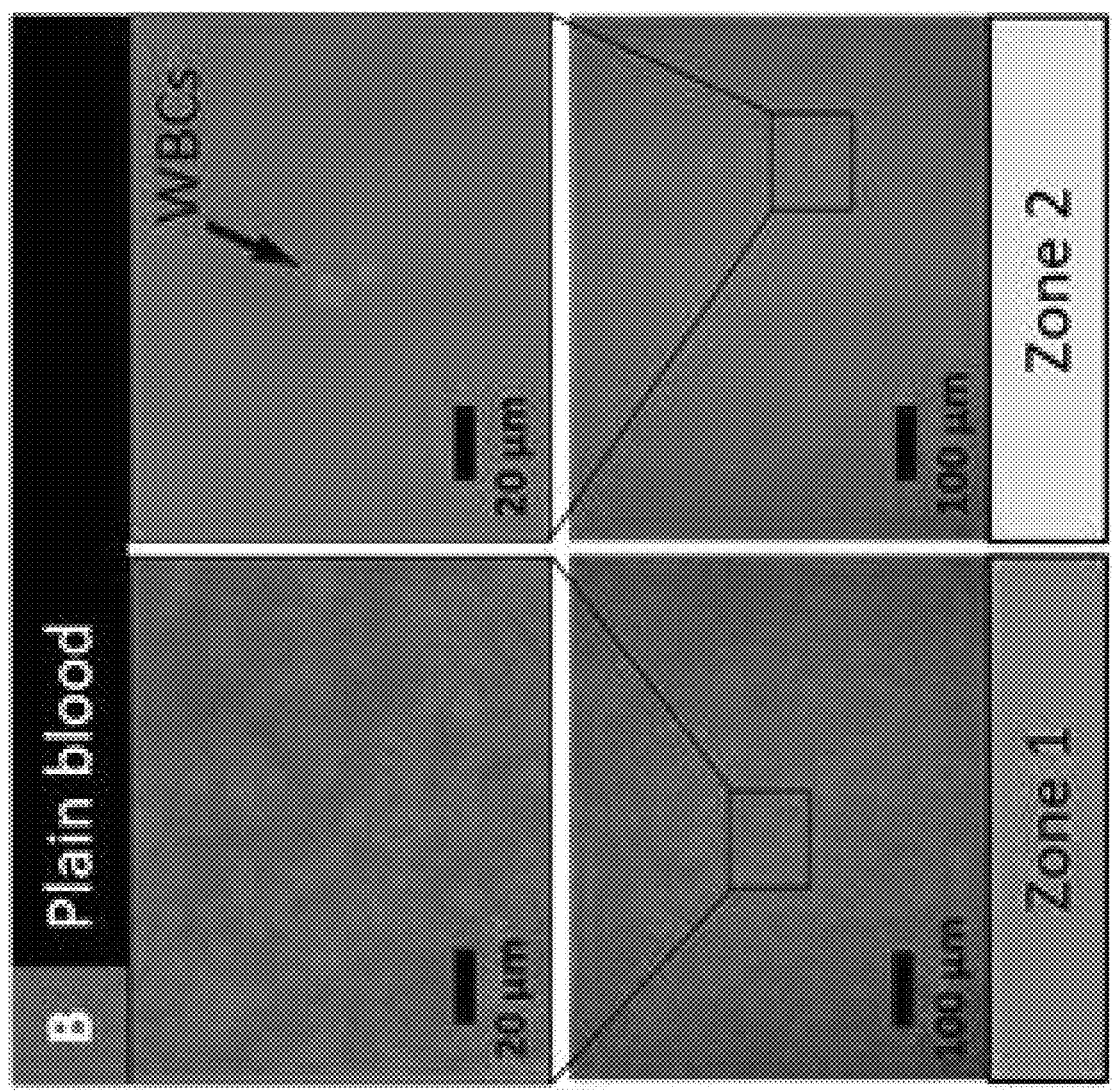

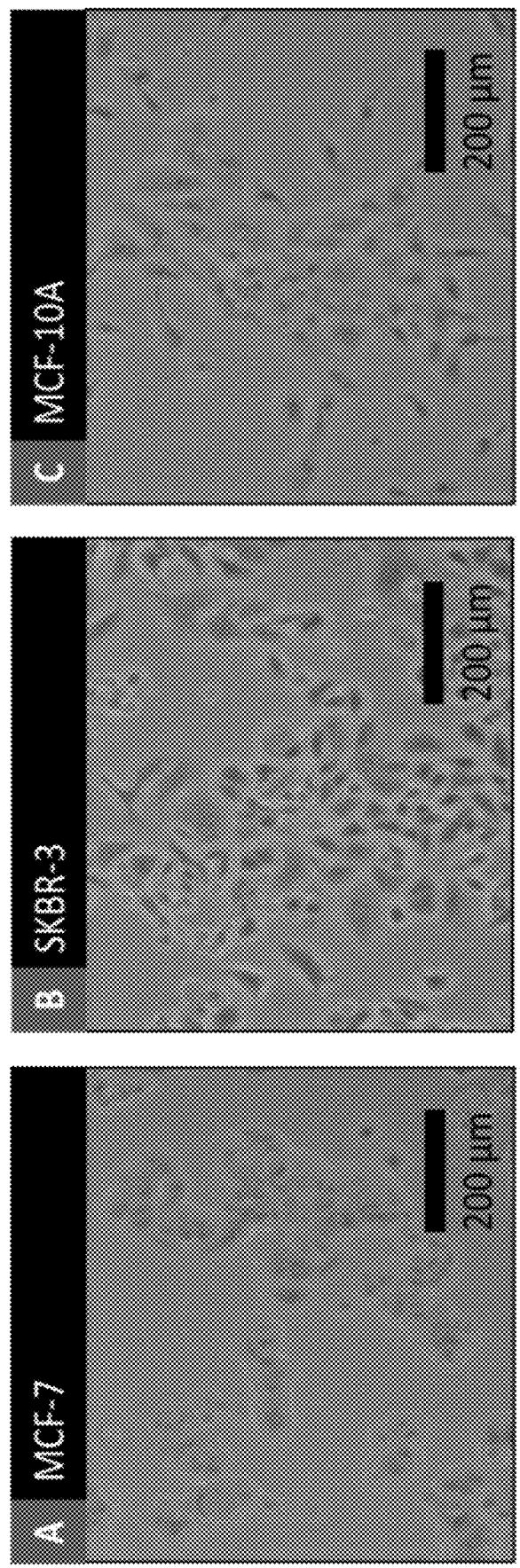

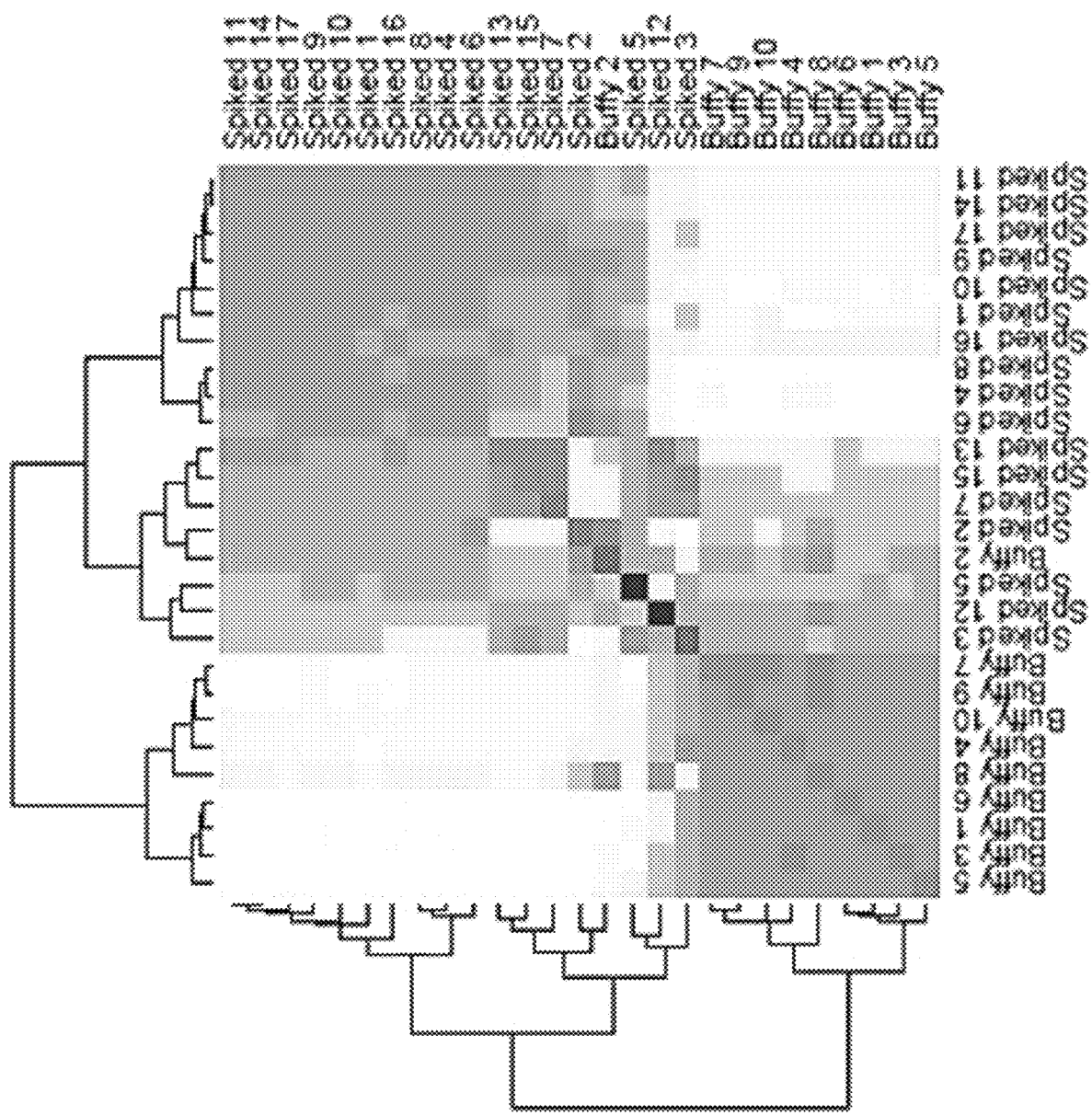

MICRO-ARRAY DEVICES FOR CAPTURING CELLS IN BLOOD AND METHODS OF THEIR USE

CROSS REFERENCE TO RELATED APPLICATION

This application claims priority to and the benefit of U.S. Provisional Patent Application No. 62/401,394, filed on Sep. 29, 2016, the entirety of which is incorporated herein by reference.

STATEMENT OF GOVERNMENT SUPPORT

This invention was made with Government Support under Grant Numbers 1463869, 1410678 and 1463987 awarded by the National Science Foundation and Grant Numbers R15CA156322 and 7R15CA156322 awarded by the National Cancer Institute. The Government has certain rights in the invention.

BACKGROUND

Circulating tumor cells (CTC) detection in blood can help study various cancers. The field of isolation and study of circulating tumor cells has been growing with many types of devices reported in the recent past based on immunomagnetic methods, microfluidic chips, laser scanning cytometry, high-throughput optical-imaging systems fiber optic array scanning technology and nano-Velcro arrays. While each method has advantages, there also many disadvantages associated with each method. However, there is still a need for devices and methods for isolation of CTCs from blood.

SUMMARY

The present disclosure provides micro-array devices for capturing cells in blood and methods of their use.

In some aspects, a method for counting cells in a blood sample is provided, the method comprising applying a blood sample onto a CNT device; allowing cells in the blood sample to differentially settle on the CNT device, and identifying and counting cells of preselected type in the blood sample.

In some aspects, there is provided a method for rapid and label-free capturing of cellular targets in a blood sample comprising applying a blood sample onto a carbon nanotubes (CNT) device; allowing cellular targets in the blood sample to adsorb onto the CNT device; and identifying and counting the cellular targets absorbed onto the CNT device. In some embodiments, the cellular targets are breast cancer cells.

In some aspects, a method for specific detection of cellular targets in the blood sample is provide, the method comprising applying a blood sample onto a CNT device; receiving an electrical signal from the CNT device, the signal being indicative of interactions between cellular targets in the blood sample and the CNT device; and applying a statistical method to distinguish between specific interactions and non-specific interactions.

In some aspects, a method for specific detection of cellular targets in a blood sample is provided, the method comprising applying a blood sample onto a CNT device; receiving an electrical signal from the CNT device, the signal being indicative of interactions between the blood sample and the CNT device; assigning the electrical signal into a zone of a zone classification scheme, wherein the zone is indicative of interactions between the blood sample and the CNT device; and distinguishing between specific interactions and non-specific interactions based on the assigned zone.

In some aspects, a method for counting cells in a blood sample is provided, the method comprising applying a blood sample onto a CNT device; allowing cells in the blood sample to differentially settle on the CNT device, and identifying and counting cells of preselected type in the blood sample.

In some embodiments, the CNT device comprises a substrate; a thin film of carbon nanotubes (CNTs) disposed on the substrate, the CNTS being functionalized with one or more antibodies capable to bind to a cellular target to be captured; and a plurality of conductive contacts disposed on the substrate and electrically coupled to the thin film, wherein the plurality of conductive contacts are configured detect a capture of the cellular targets by the one or more antibodies.

BRIEF DESCRIPTION OF THE DRAWINGS

The present disclosure is further described in the detailed description which follows, in reference to the noted plurality of drawings by way of non-limiting examples of exemplary embodiments, in which like reference numerals represent similar parts throughout the several views of the drawings, and wherein:

FIG. 1 presents a diagnostic chip according to some embodiments of the present disclosure.

FIGS. 3A-3H presents a biosensor array micro-fabrication process.

FIG. 4A presents a specific interaction with an Anti-Her2 functionalized device with 1000 SKBR3 cells spiked in blood. FIG. 4B shows a non-specific interaction with an Anti-Her2 functionalized device with 1000 MCF10A cells spiked in blood. FIG. 4C shows another Non-Specific Interaction with Anti-Her2 functionalized device with plain blood adsorption. FIG. 4D shows the zone classification scheme of the electrical signals.

FIG. 6A presents a heat map, a summary of the relationship between electrical signatures and the cellular-proteomic features, namely overexpression of Her2.

FIG. 6B presents the Her2 clustering data, suggesting all SKBR3 cells in blood overexpressing Her2 are clustered/partitioned together.

FIG. 7A, FIG. 7B, and FIG. 7C demonstrate cell capture.

Figure 9B:
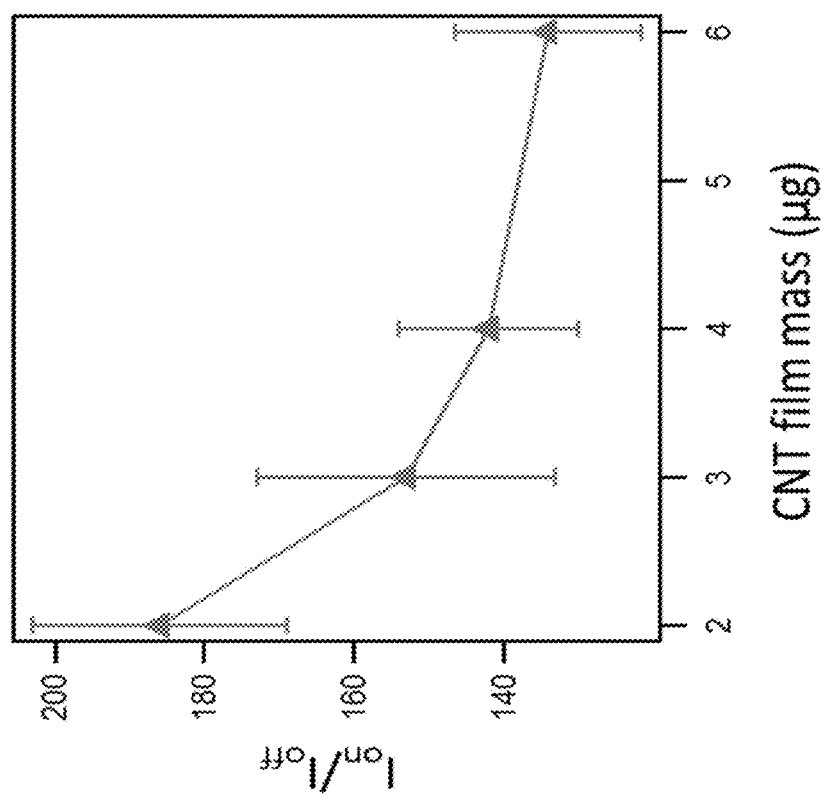
Figure 9A:
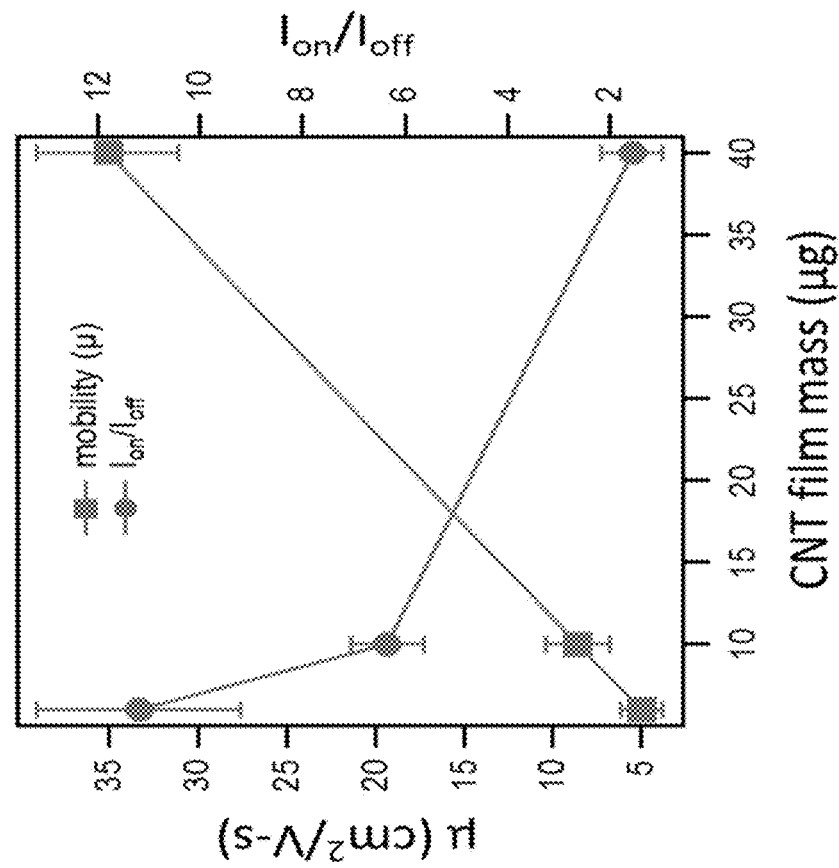

FIG. 9A and FIG. 9B present transistor properties versus film mass. FIG. 9A shows mobility and on-off ratio of a back-gated CNT device in one plot. As CNT film mass increases on-off ratio decreases and mobility increases FIG. 9B shows the on-off ratio for a top-liquid-gated CNT device, gate is applied by Ag/AgCl reference electrode through electrolyte solution (1×PBS).

FIG. 10A-FIG. 10J present the device array data for 1000 cells/5 µL variation.

FIG. 11A-FIG. 11J present the device array data for 100 cells/5 µL variation.

Figure 12A:
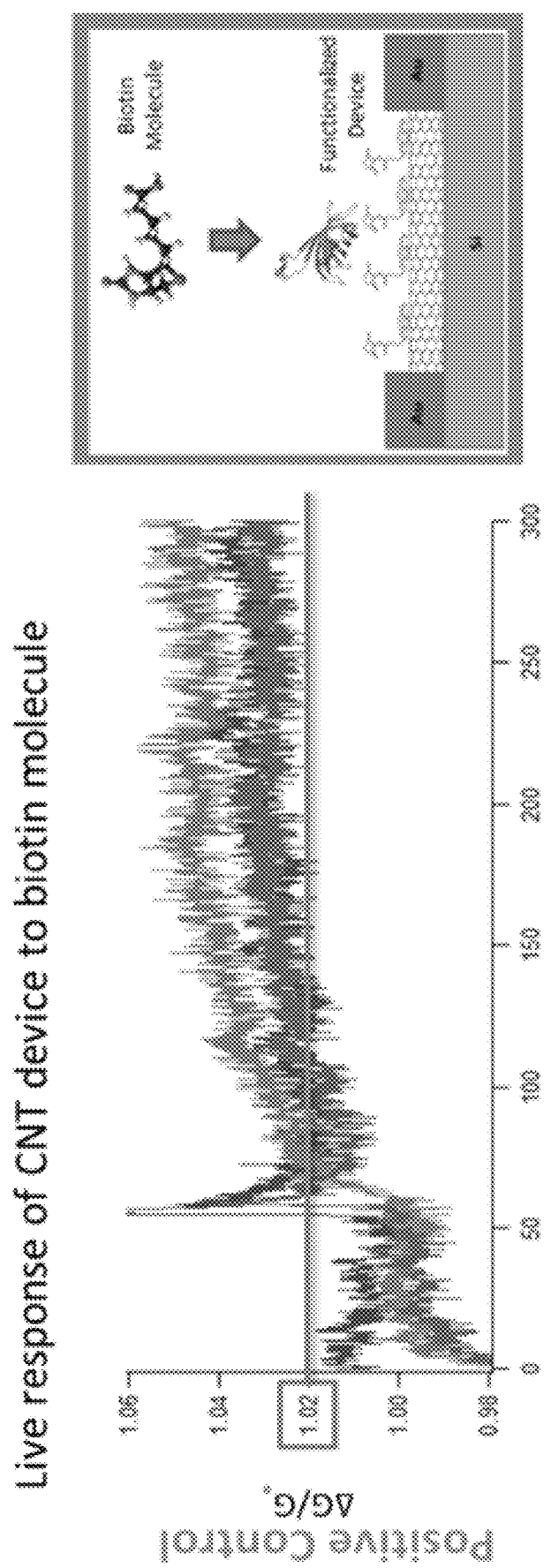
Figure 12B:
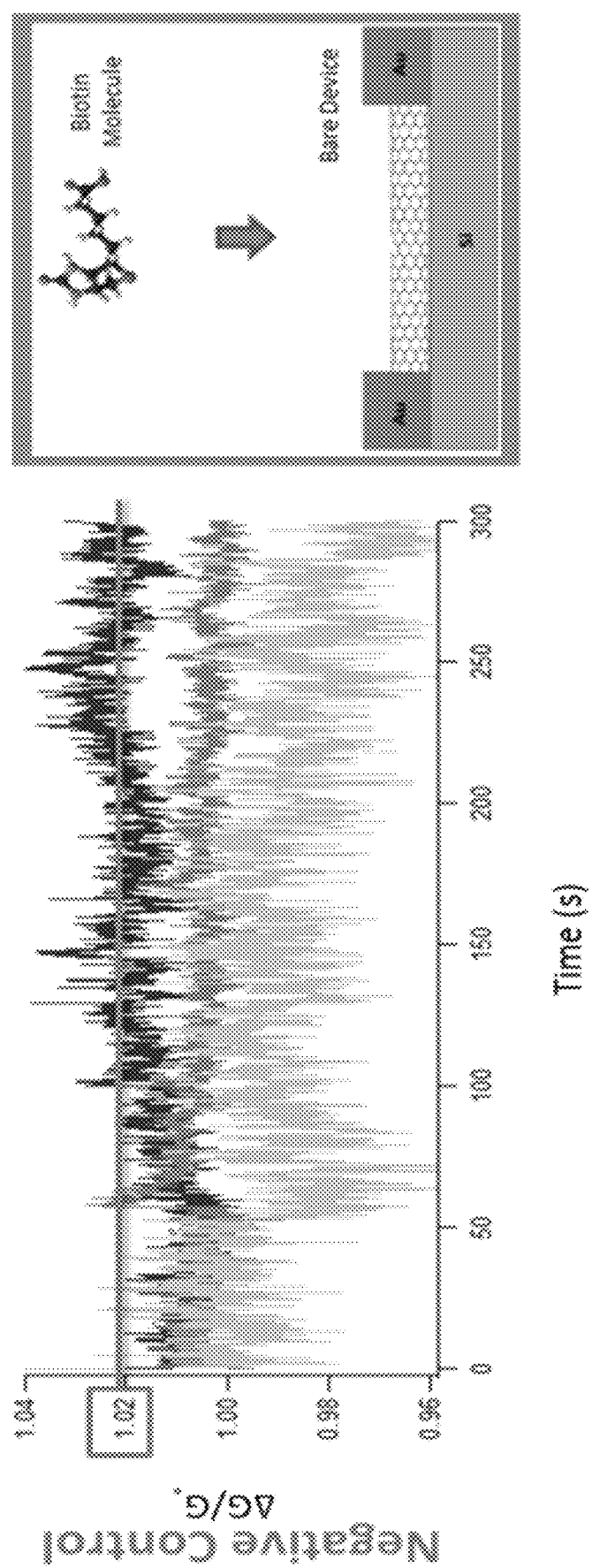

FIG. 12A and FIG. 12B show a normalized live response of six CNT devices, three functionalized with streptavidin (FIG. 12A) and three not functionalized bare CNT devices (FIG. 12B).

Figure 13B:
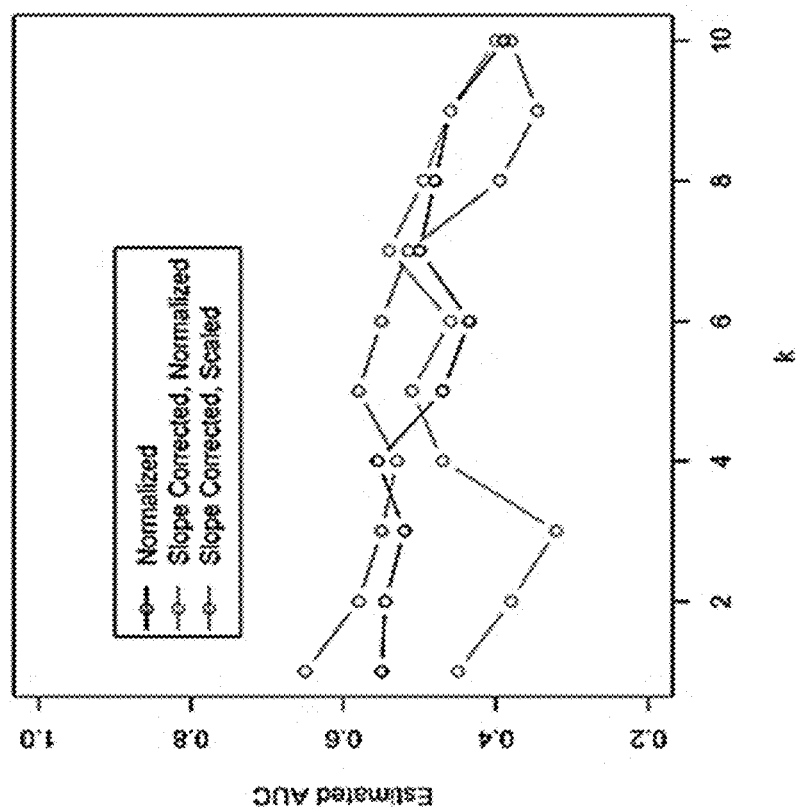
Figure 13A:
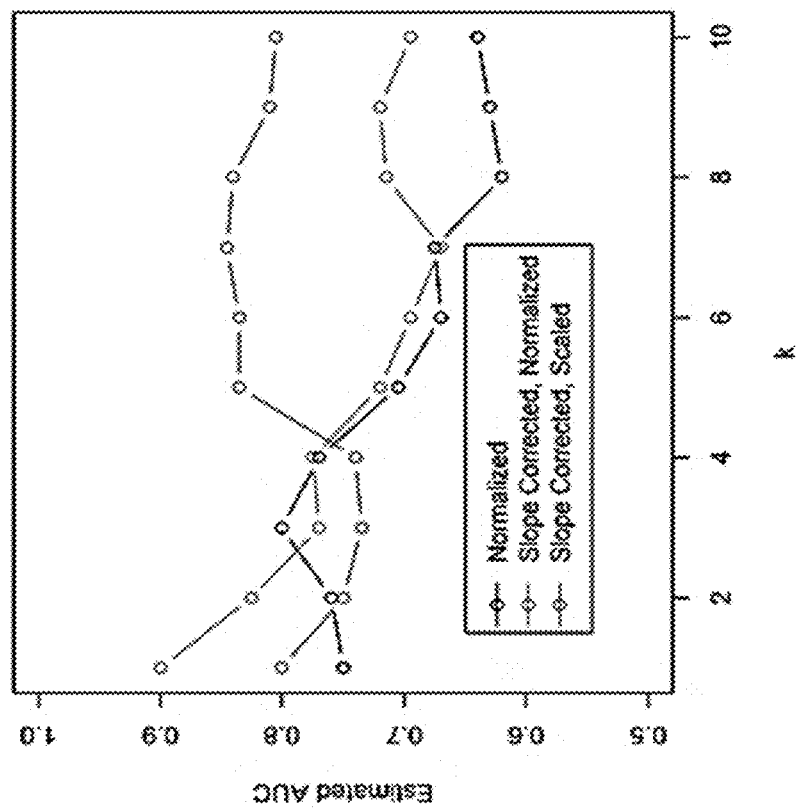
Figure 13C:
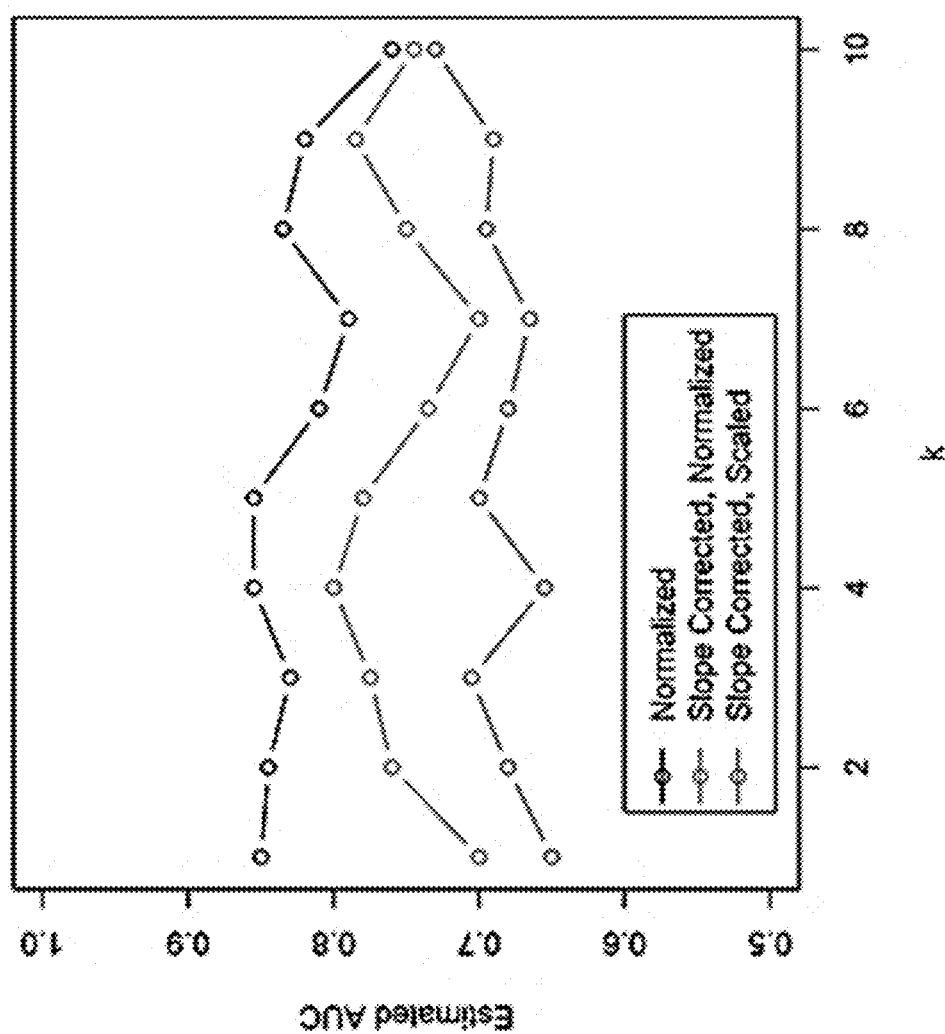

FIG. 13A, FIG. 13B, and FIG. 13C present DTW-based classification. FIG. 13A shows the cross-validation estimated AUC for discriminating a high concentration of SKBR-3 cells given anti-HER-2 antibody. FIG. 13B presents the cross-validation estimated AUC for discriminating a low concentration of SKBR-3 cells given anti-HER-2 antibody. FIG. 13C presents the cross-validation estimated AUC for discriminating antibodies, anti-HER-2 and IgG functionalized devices, in 1000 SKBR-3 cell concentration.

FIG. 14A-FIG. 14I present cell capture and enumeration.

Figure 15A:
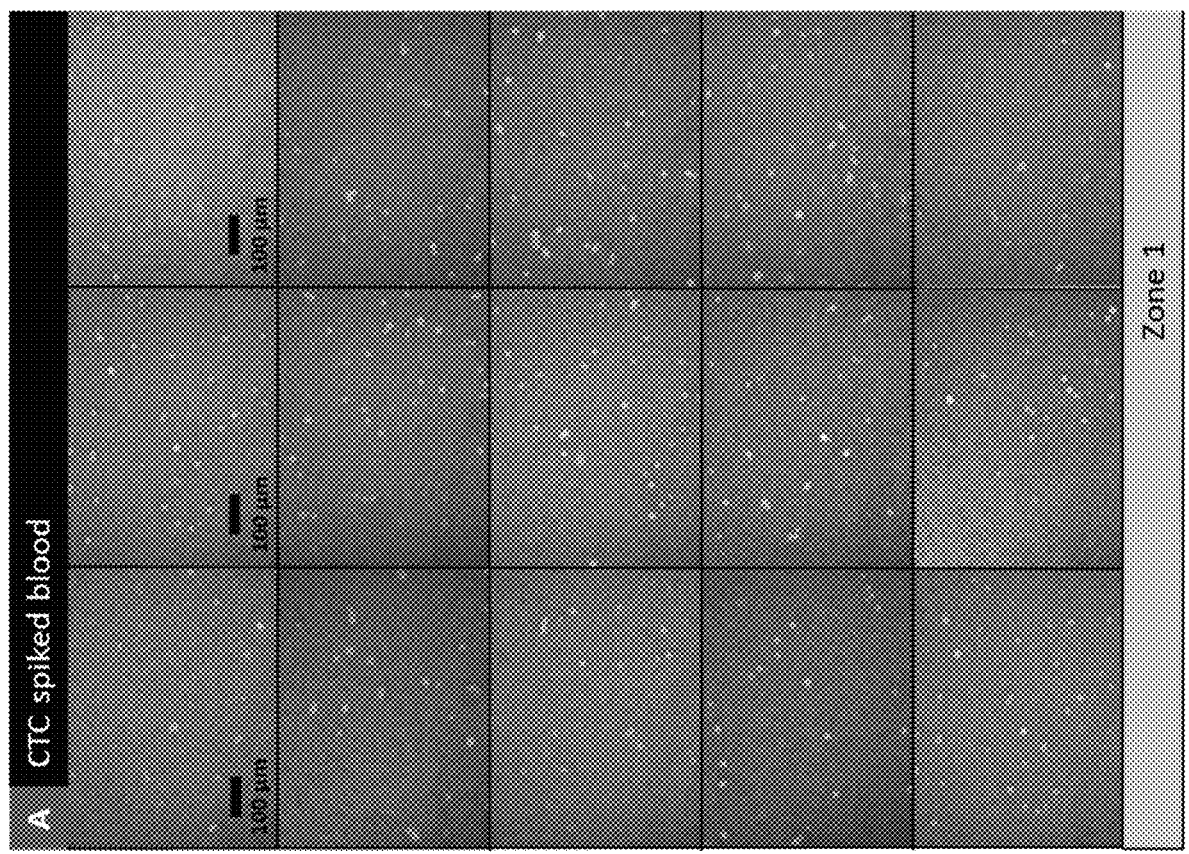
Figure 15B:
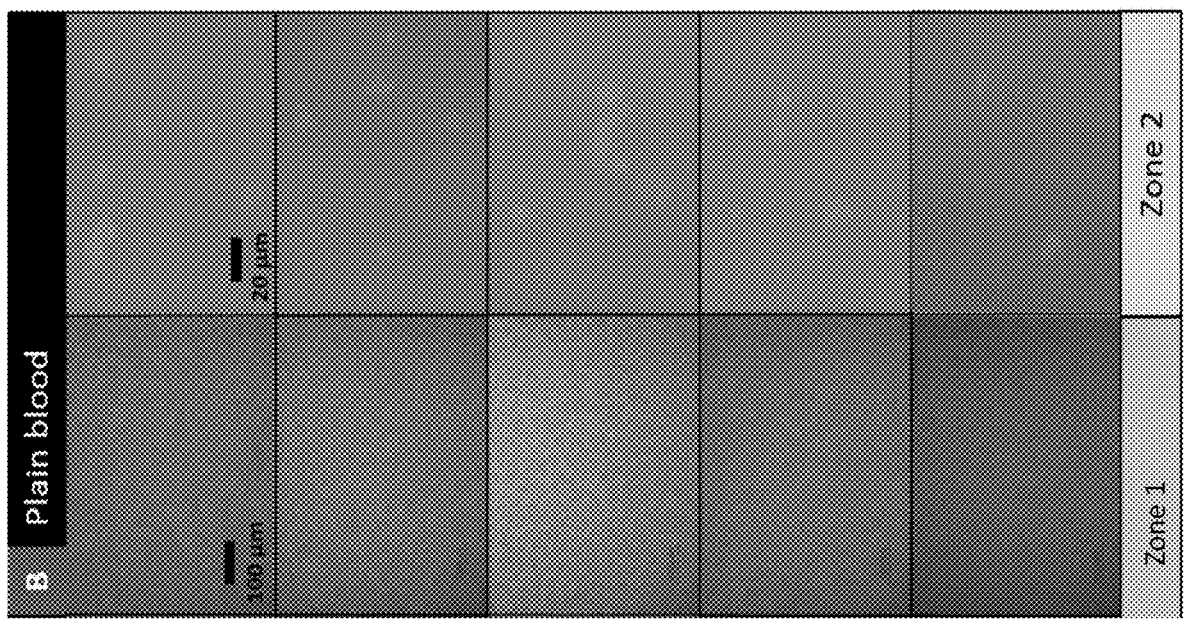

FIG. 15A and FIG. 15B present cancer cell capture and enumeration with optical microscopic images of 1000 SKBR3 spiked blood sample droplets on top of the device.

Figure 16A:
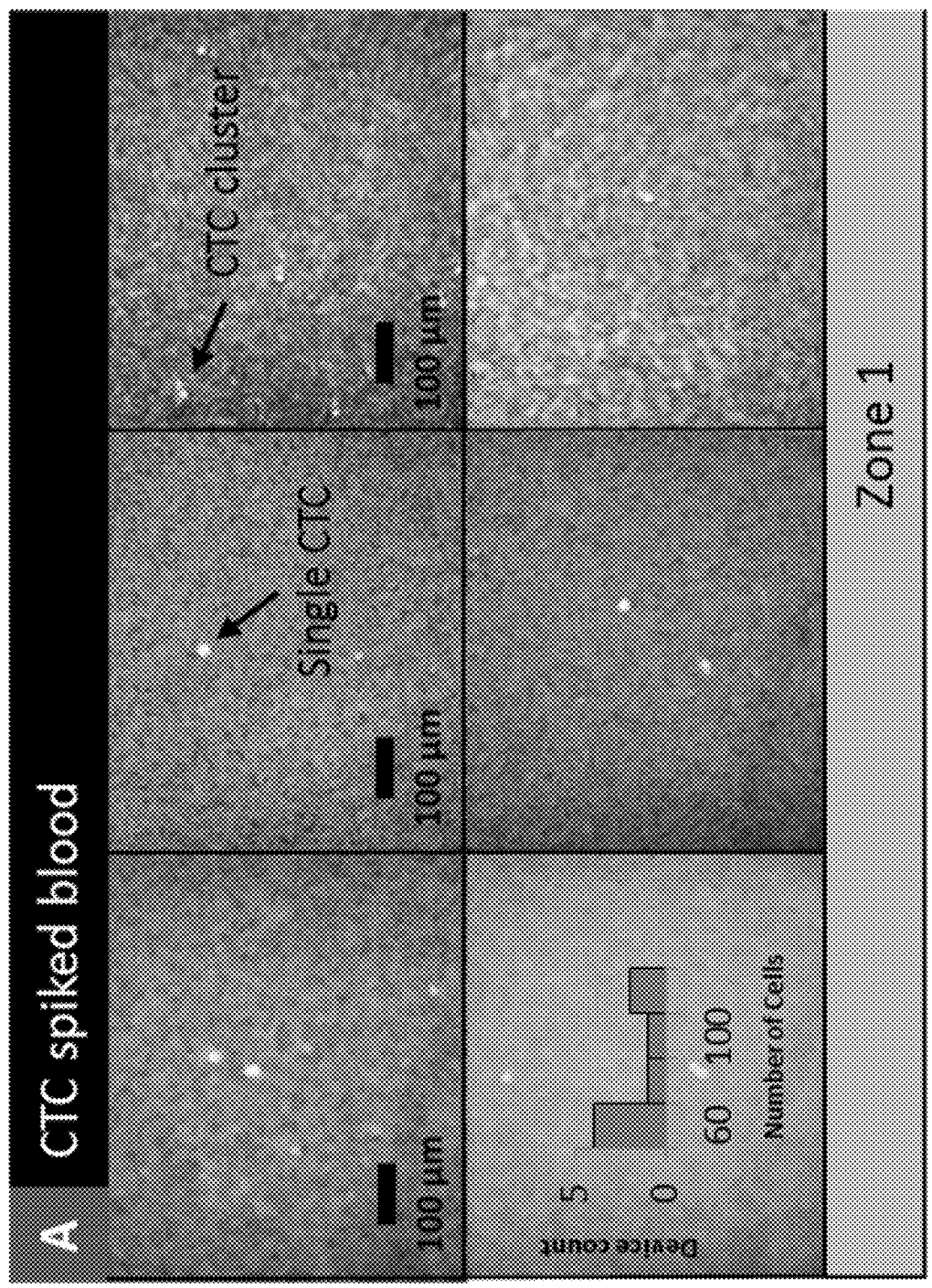
Figure 16B:
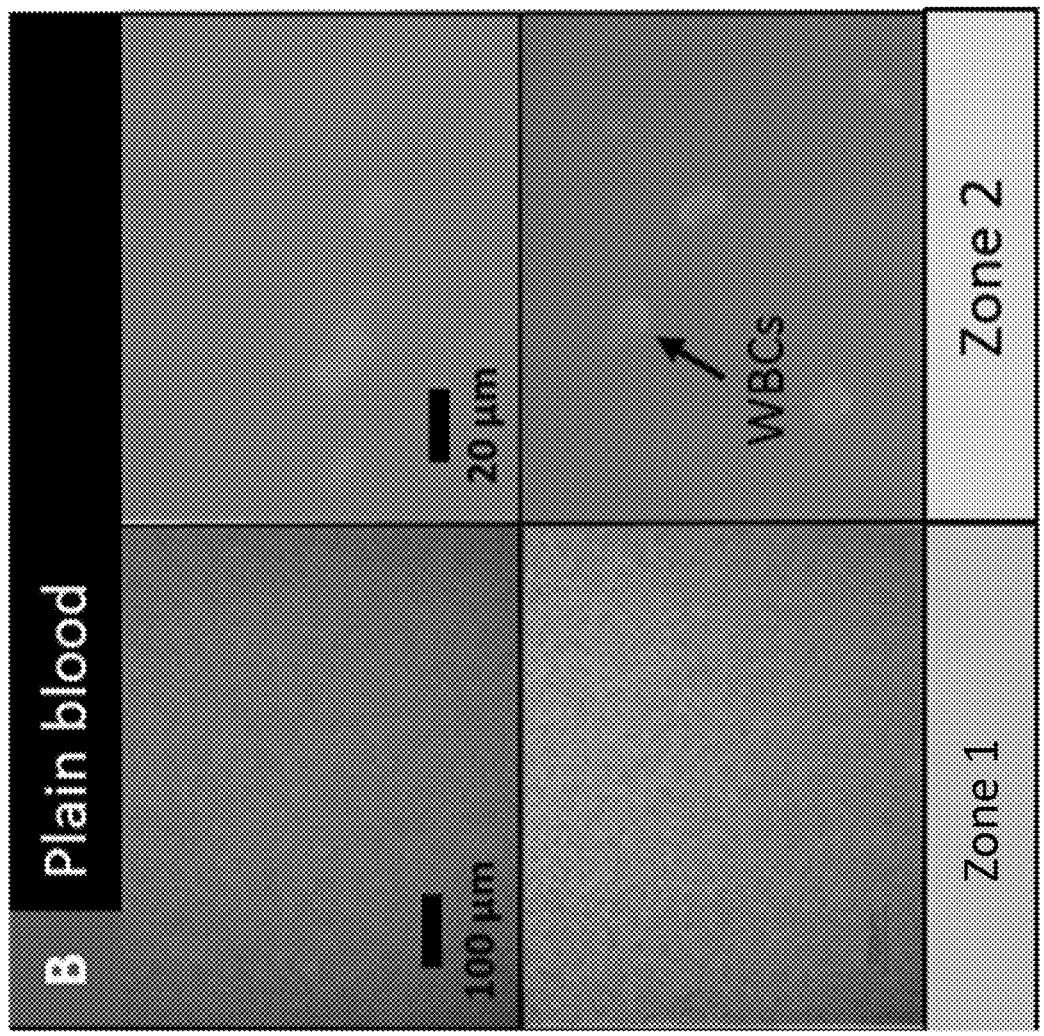

FIG. 16A and FIG. 16B present cancer cell capture with the optical images of part of the devices imaged that were adsorbed with 100 SKBR3 cells spiked blood sample at 20× magnification.

Figure 17D:
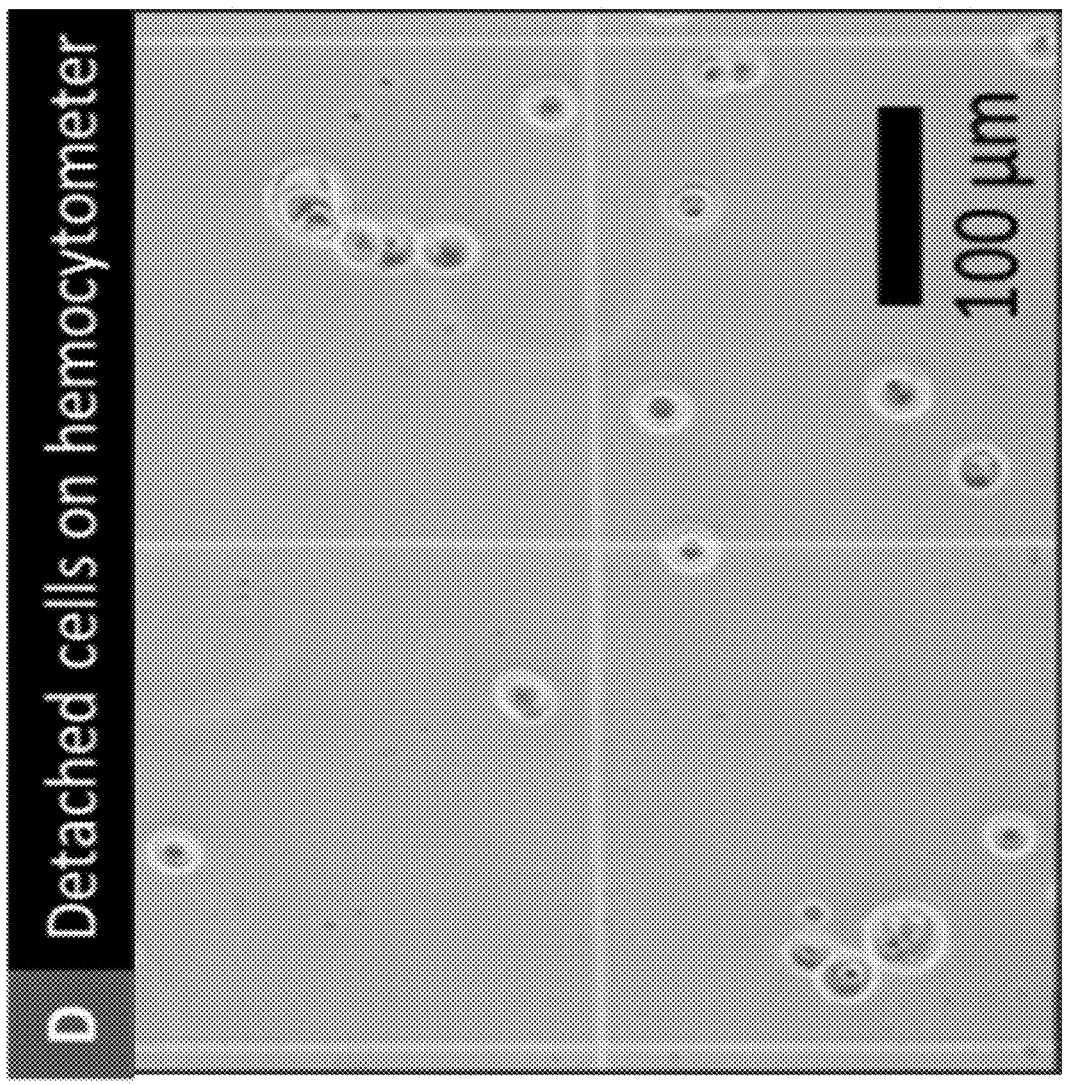

FIG. 17A, FIG. 17B, and FIG. 17C present optical microscope images showing the cells cultured at ~80% confluency. FIG. 17D shows an optical microscope image of the detached SKBR-3 cells.

Figure 18:
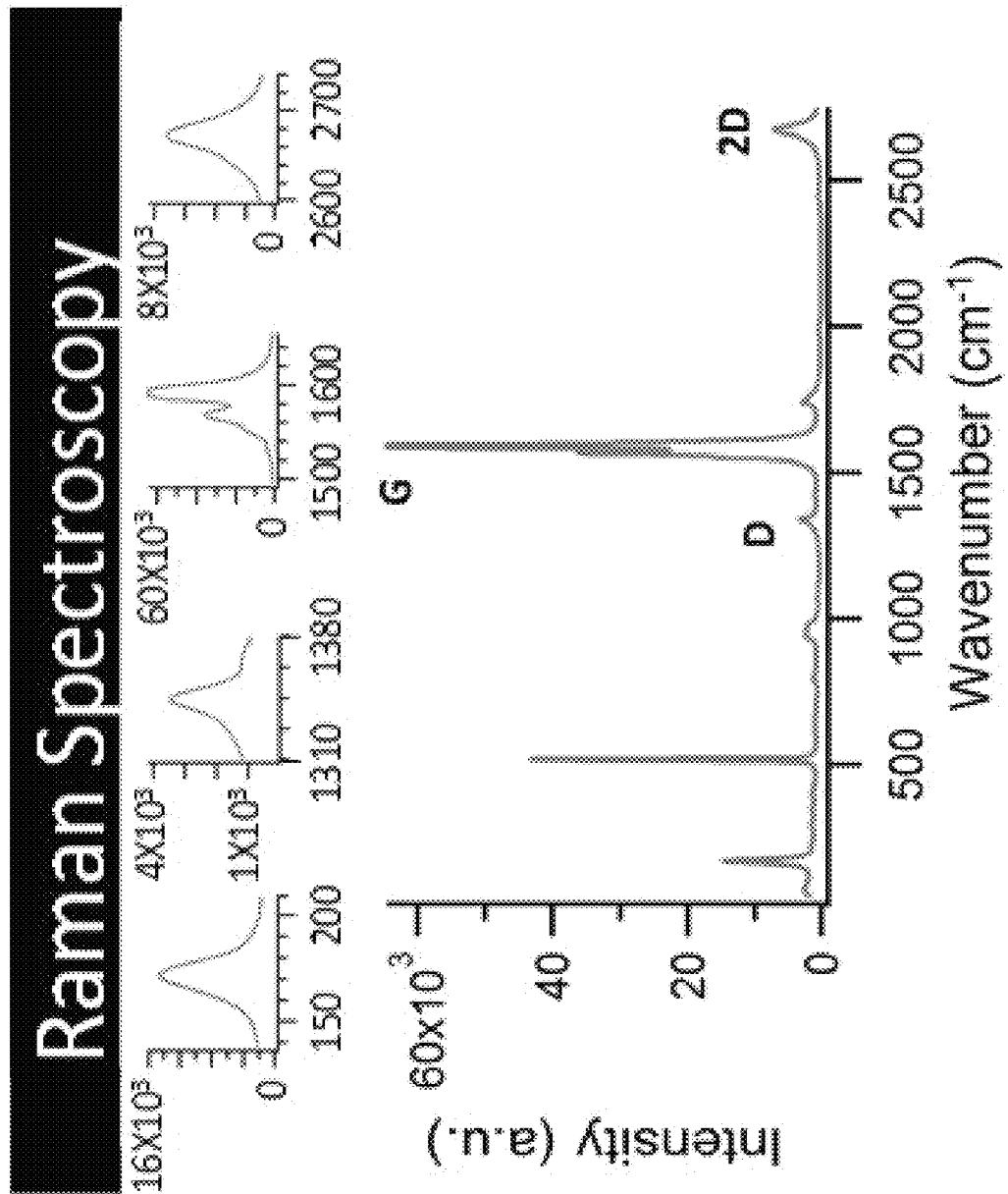

FIG. 18 shows the Raman spectrum of semiconducting carbon nanotubes showing a large G band, small D band and 2D band. The IG/ID~30 was observed in these nanotubes.

Figure 19A:
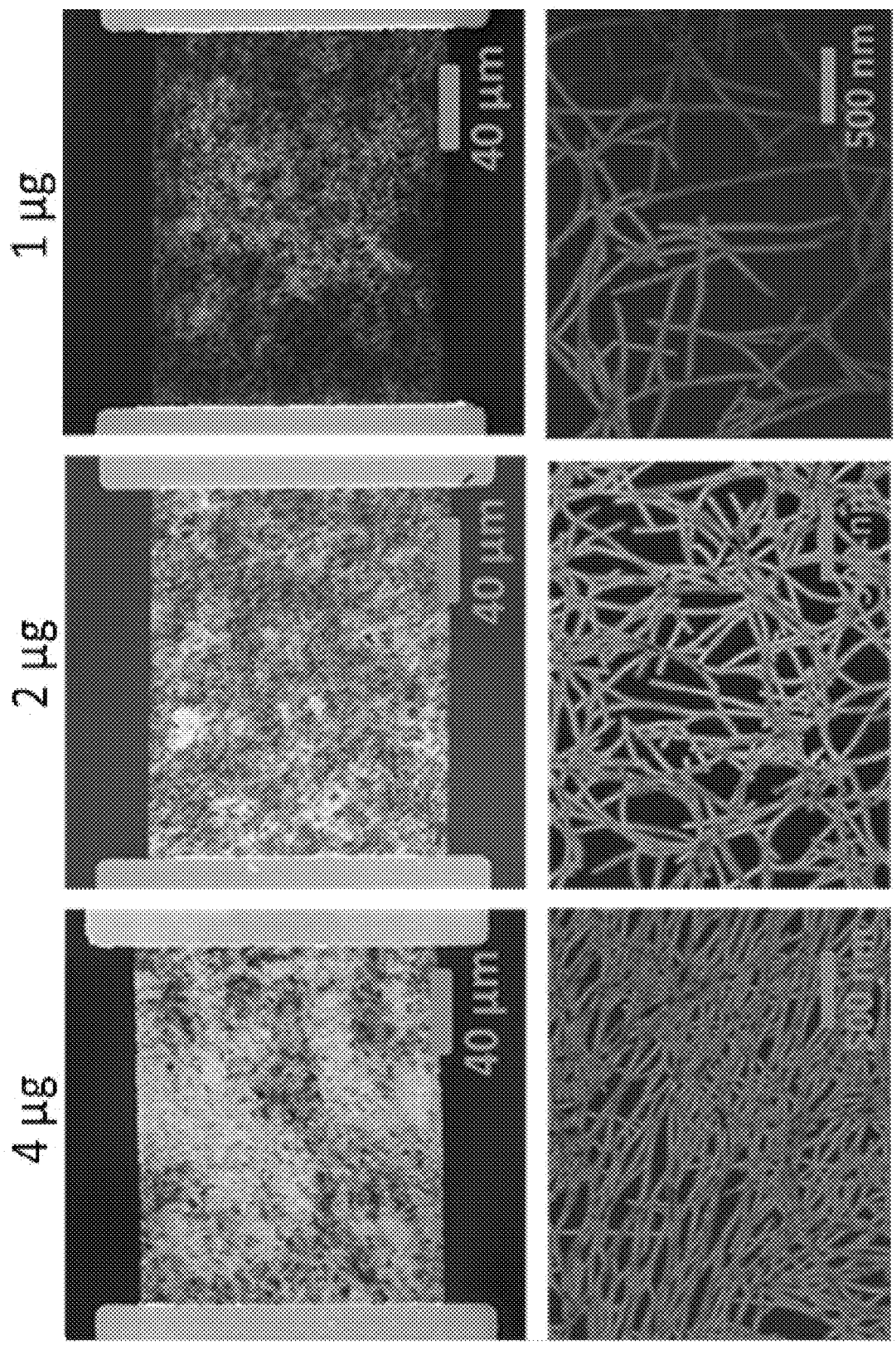
Figures 19B, 19C:
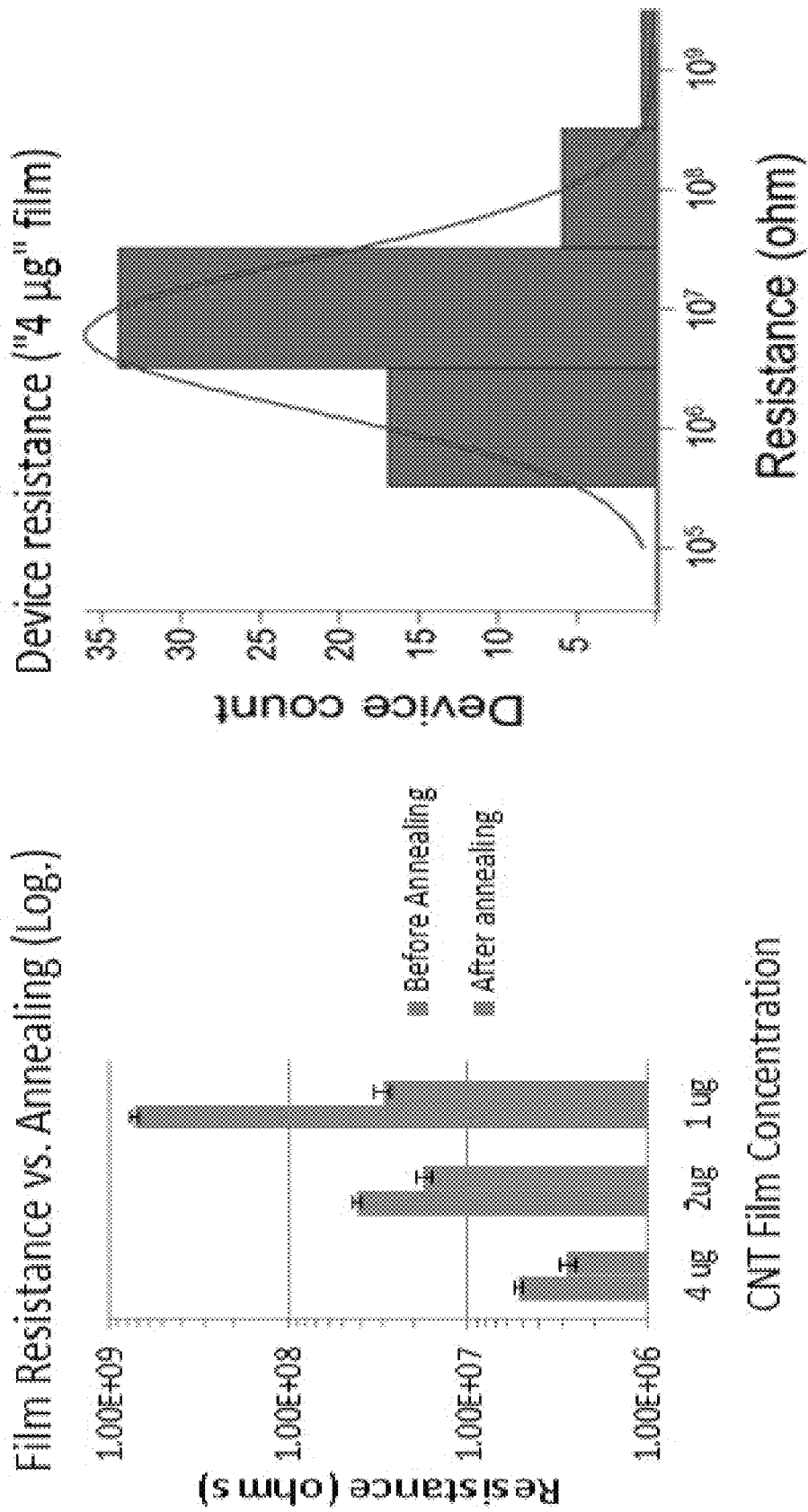

FIG. 19A, FIG. 19B, and FIG. 19C present the electrical characteristics of nanotube devices. FIG. 19A shows a SEM image of the actual device fabricated from 4 µg, 2 µg, and 1 µg of carbon nanotube film and their corresponding high magnification; FIG. 19B shows the film resistance before and after annealing at 250 C; FIG. 19C presents a histogram suggesting a high degree of control in device resistance over 58 devices.

Figure 20A:
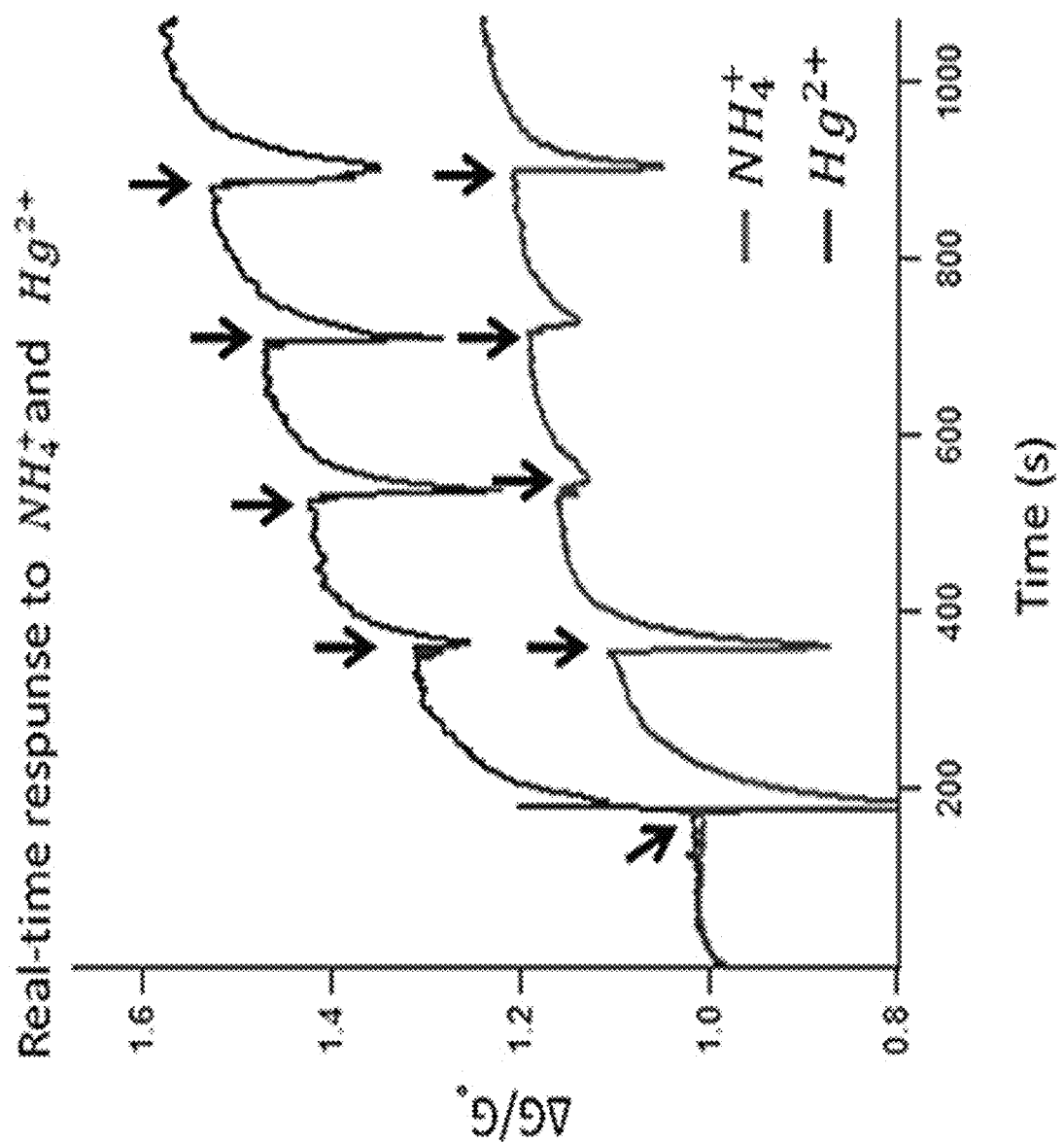
Figure 20B:
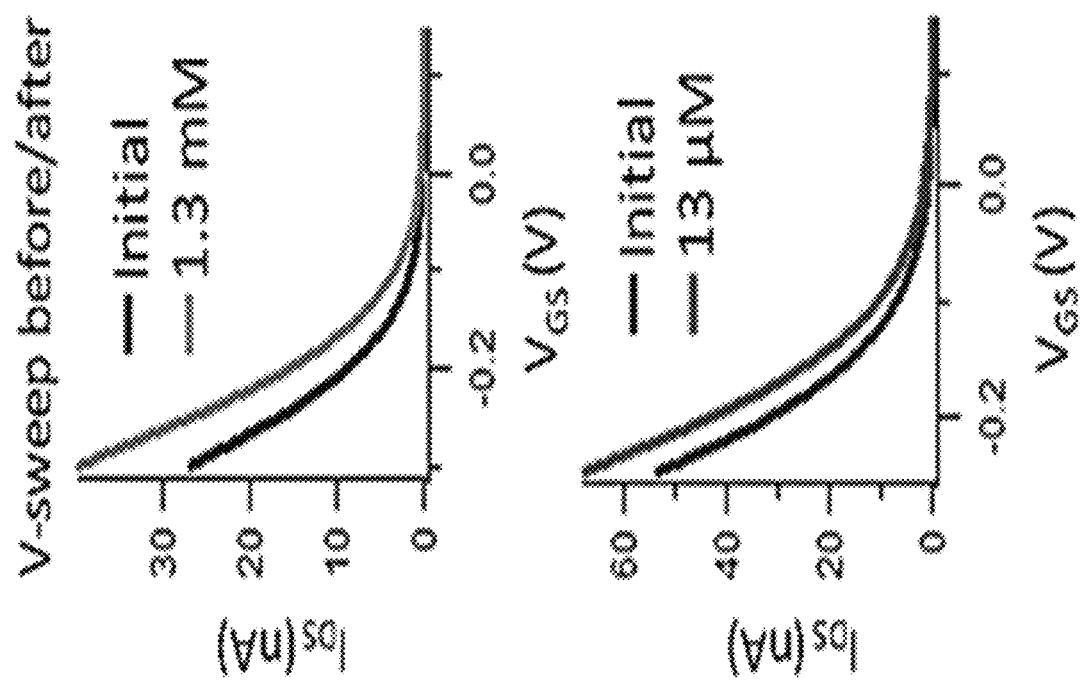
Figure 20C:
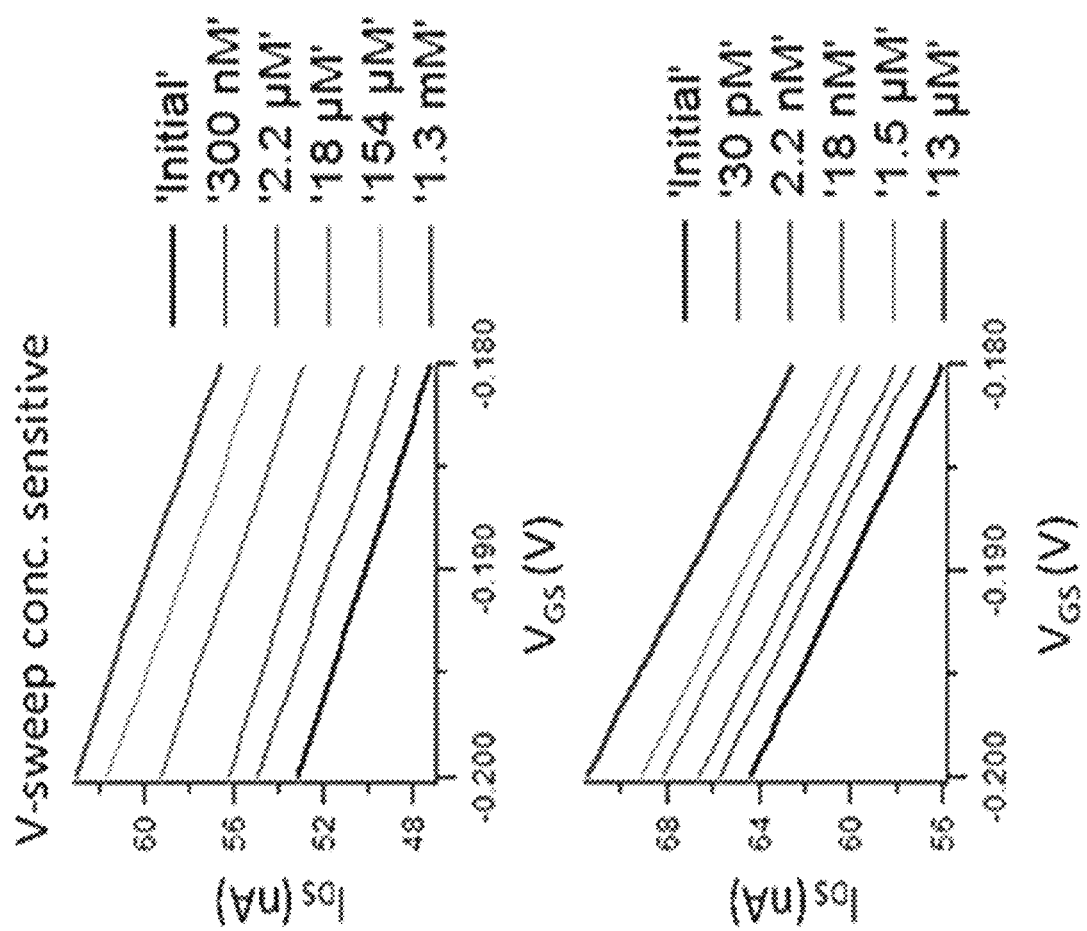
Figure 20D:
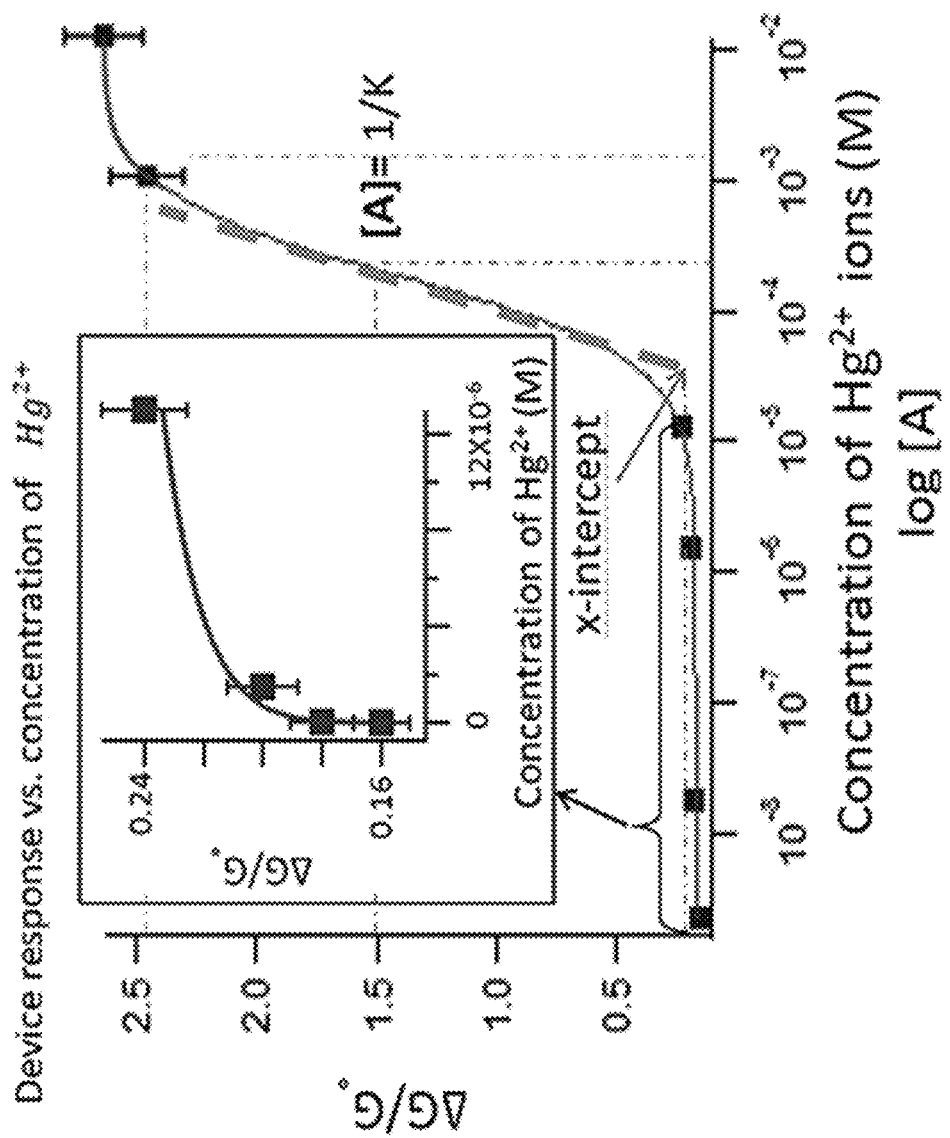

FIG. 20A, FIG. 20B, FIG. 20C, and FIG. 20D present an understanding of a semiconducting nanotube network. FIG. 20A presents a real time response of device to concentrations of $NH_4^+$, 300 nM to 1.3 mM, and $Hg^{2+}$, 30 pM to 13 µM, ions; FIG. 20B shows a voltage sweep before and after exposure to $NH_4^+$ and $Hg^{2+}$ ions; FIG. 20C shows the concentration sensitivity of the voltage sweep for $NH_4^+$ and $Hg^{2+}$ ions; FIG. 20D presents a normalized signal conductance versus a concentration of $Hg^{2+}$ ions, suggesting Langmuir-adsorption isotherm. The inset shows the percentage sensitivity versus concentration for $Hg^{2+}$. Similar results were seen for $NH_4^+$ ions suggesting same sensing mechanism.

Figure 21A:
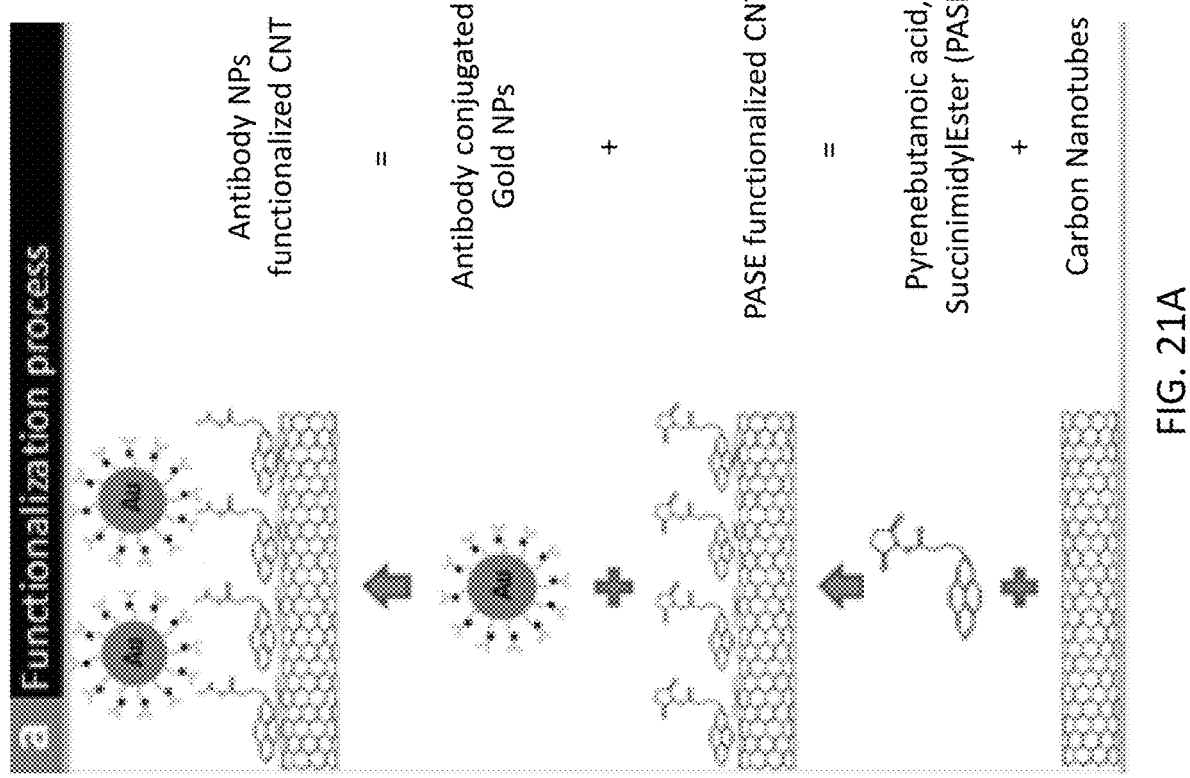
Figure 21C:
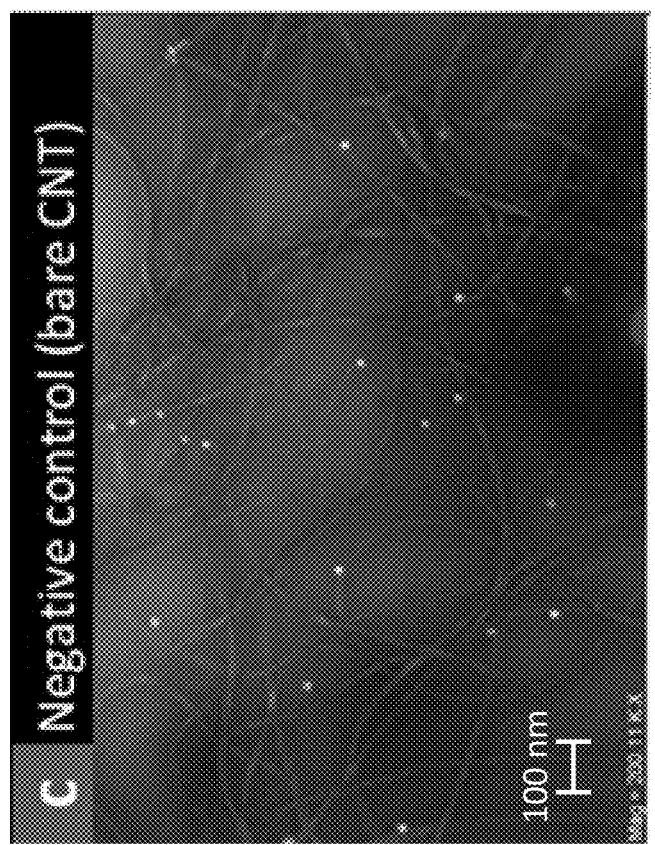
Figure 21B:
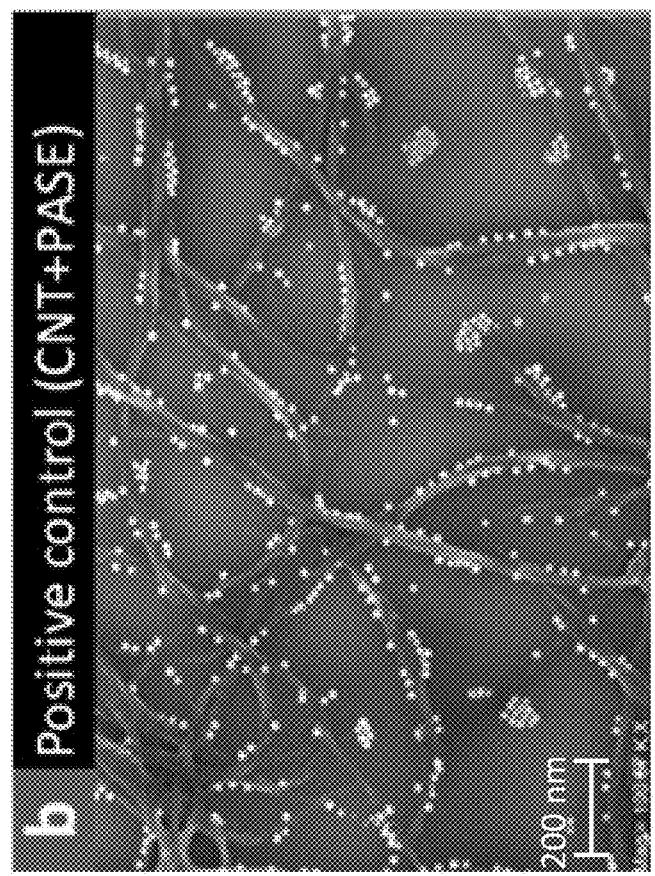
Figure 21D:
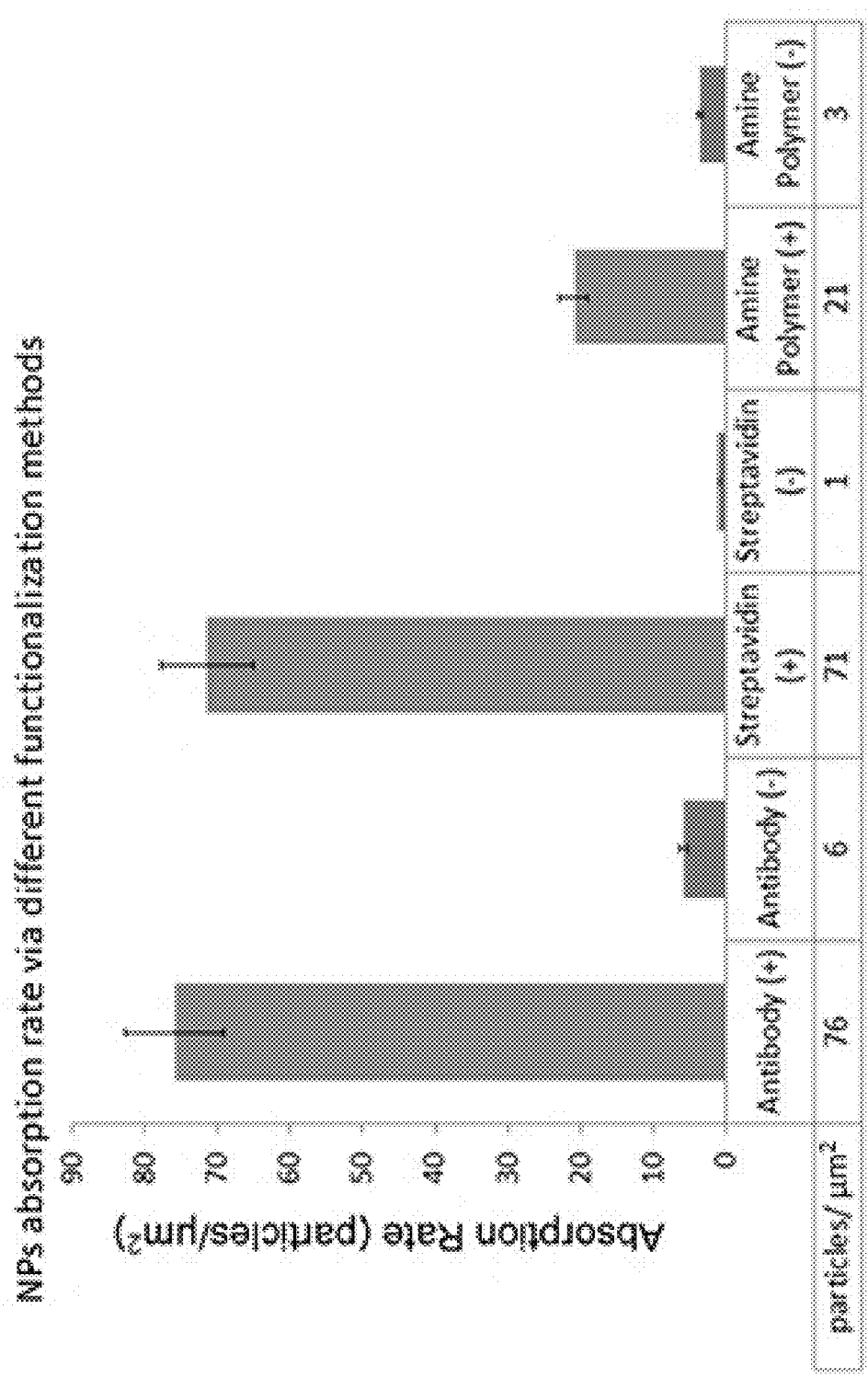

FIG. 21A, FIG. 21B, FIG. 21C, and FIG. 21D present the functionalization of antibodies. FIG. 21A presents a schematic of the PASE functionalization protocol; FIG. 21B shows a SEM image of positive control suggesting a high degree of antibody functionalization; FIG. 21C shows a SEM image of negative control suggesting no functionalization; FIG. 21D presents a comparison of different functionalization protocols including PASE-antibody, streptavidin-biotin and amine-polymer-NP conjugation.

Figure 22B:
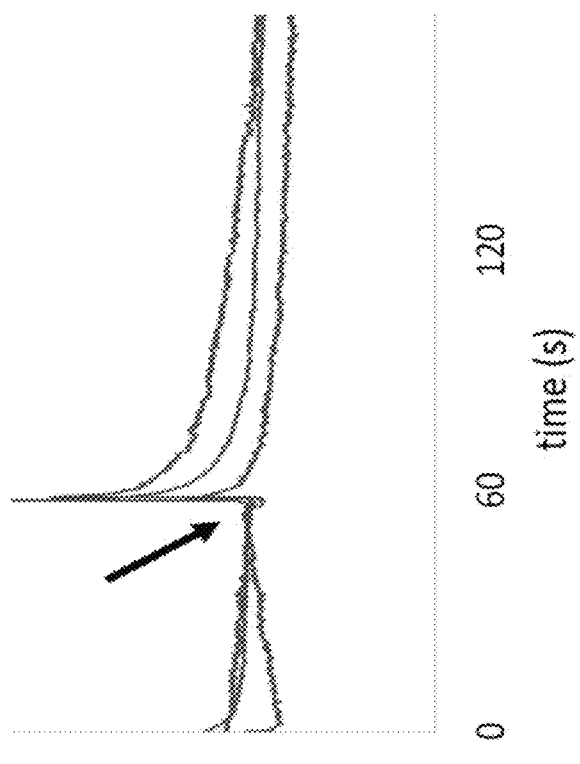
Figure 22A:
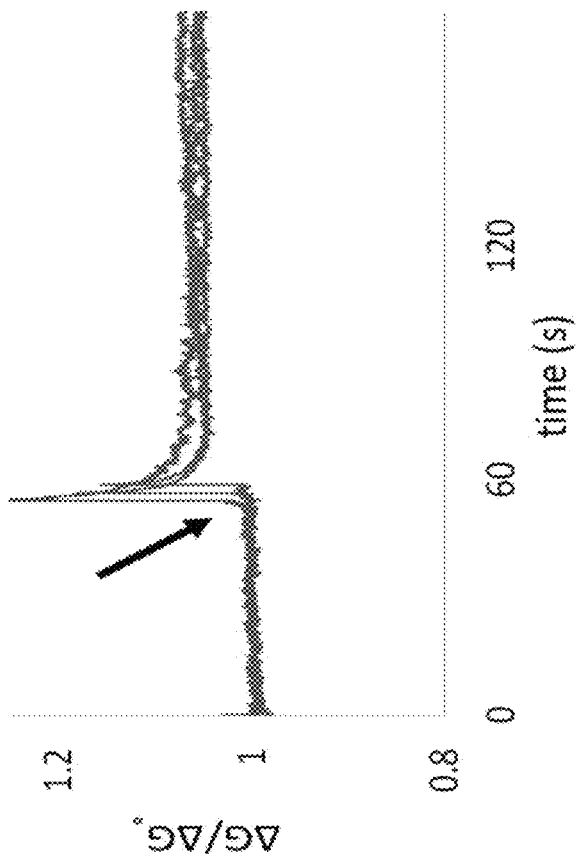
Figures 23A, 23B:
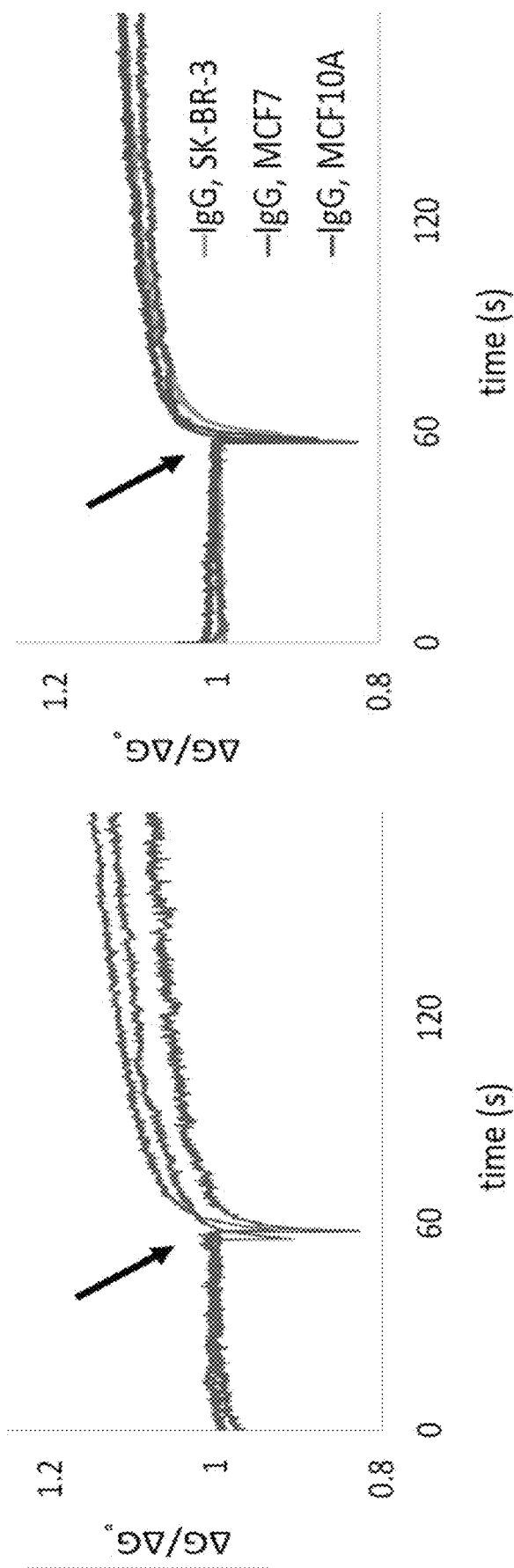

FIG. 22A, FIG. 22B, FIG. 23A, and FIG. 23B present testing in cell cultures. FIG. 22A shows a normalized device conductance of an anti-EpCAM functionalized device with SKBR3 cancer cells; FIG. 22B shows a normalized device conductance of anti-EpCAM functionalized device with MCF7 cancer cells; FIG. 23A shows a normalized device conductance of anti-EpCAM functionalized device with MCF10 A normal cells; FIG. 23B shows a representative graph of normalized device conductance of anti-IgG functionalized device with SKBR3, MCF7 and MCF10A cells.

Figure 24A:
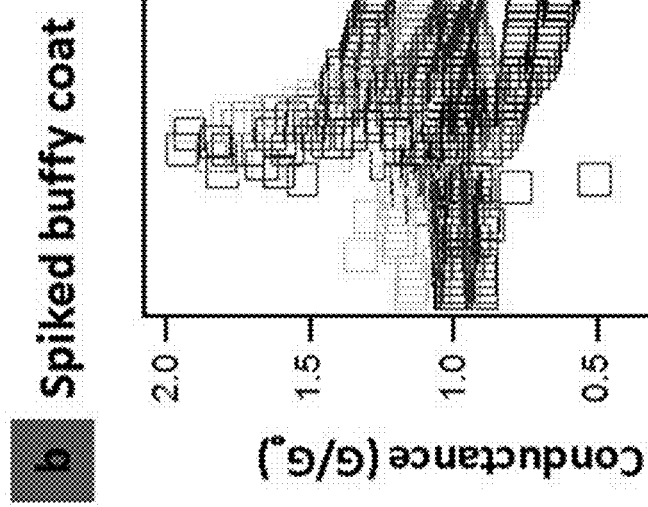
Figure 24B:
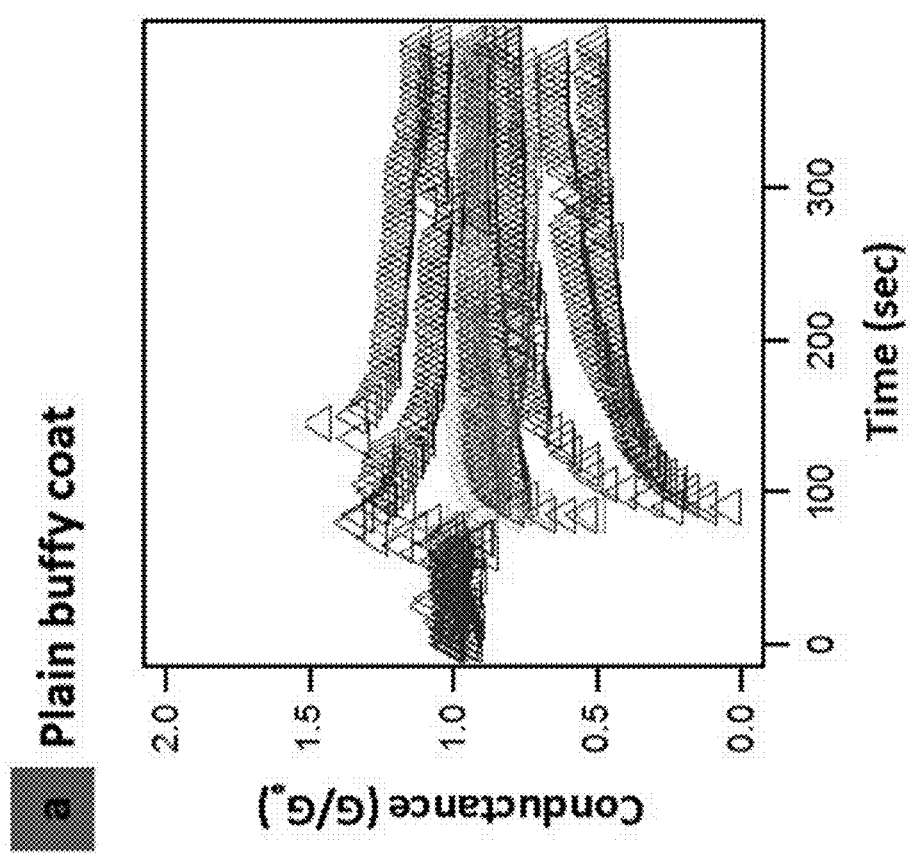

FIG. 24A-24B present a merge of sensor arrays with statistical classifiers in a training set, showing conductance versus time from arrays of sensors.

FIG. 25 presents a heat map showing a summary of the relationship between electrical signatures and the cellular-proteomic features namely overexpression of EpCAM in spiked buffy coats versus buffy coats.

Figure 26A:
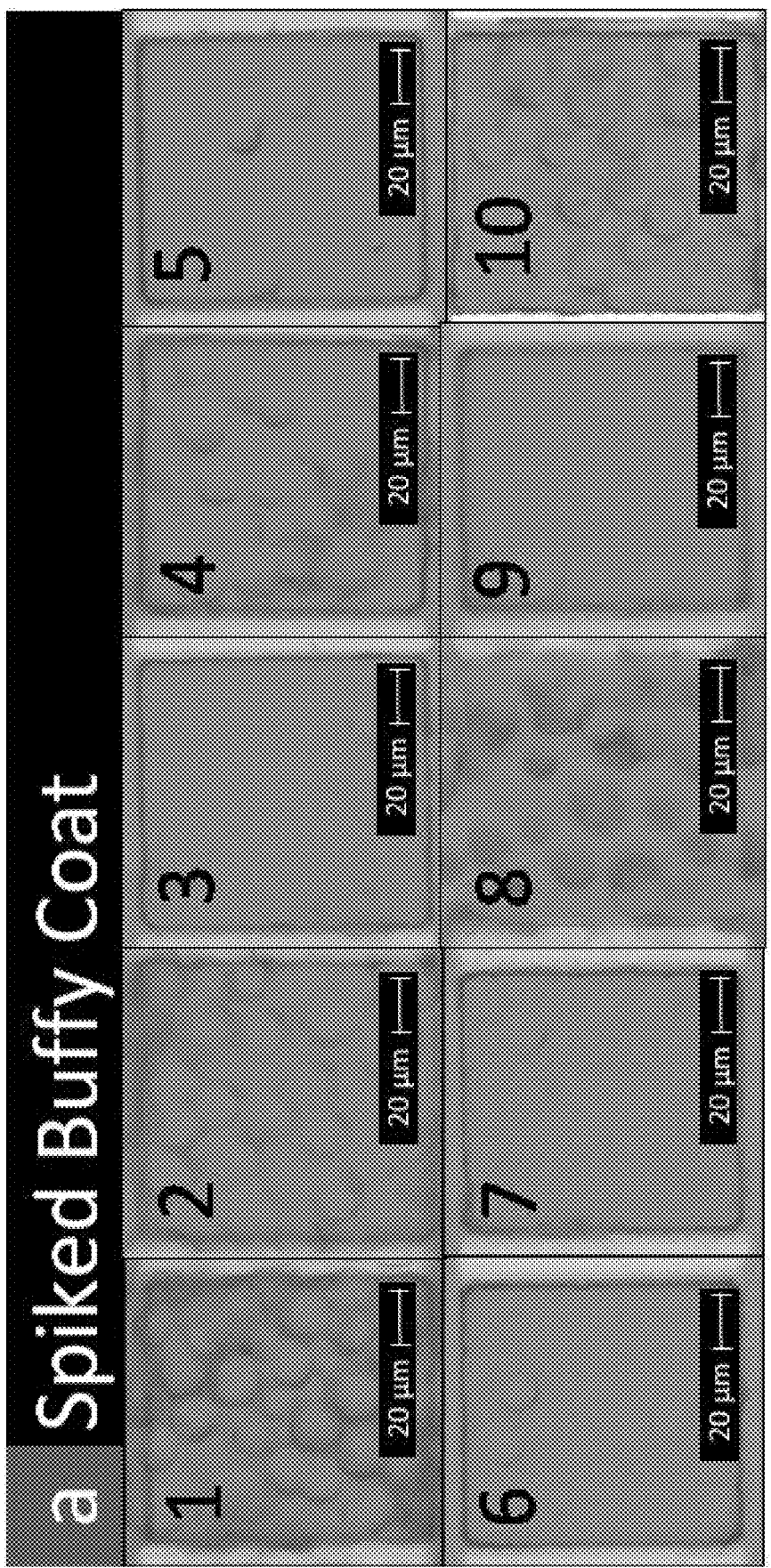
Figure 26B:
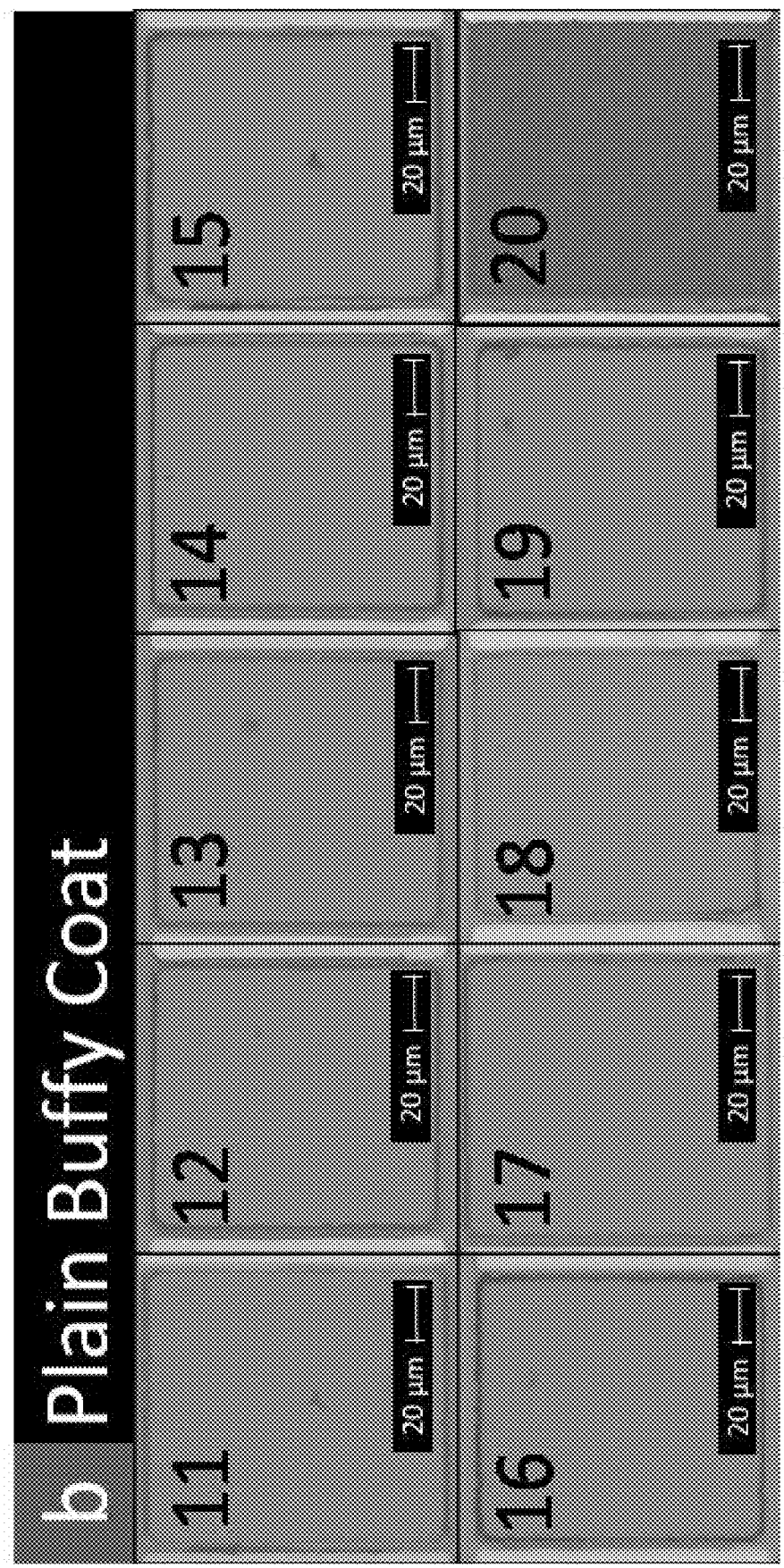

FIG. 26A and FIG. 26B present cell capture using nanotube devices based on optical microscopy. FIG. 26A presents the optical microscopy of spiked cells in buffy coats using nanotube devices; FIG. 26B presents optical microscopy of plain buffy coats.

Figure 27:
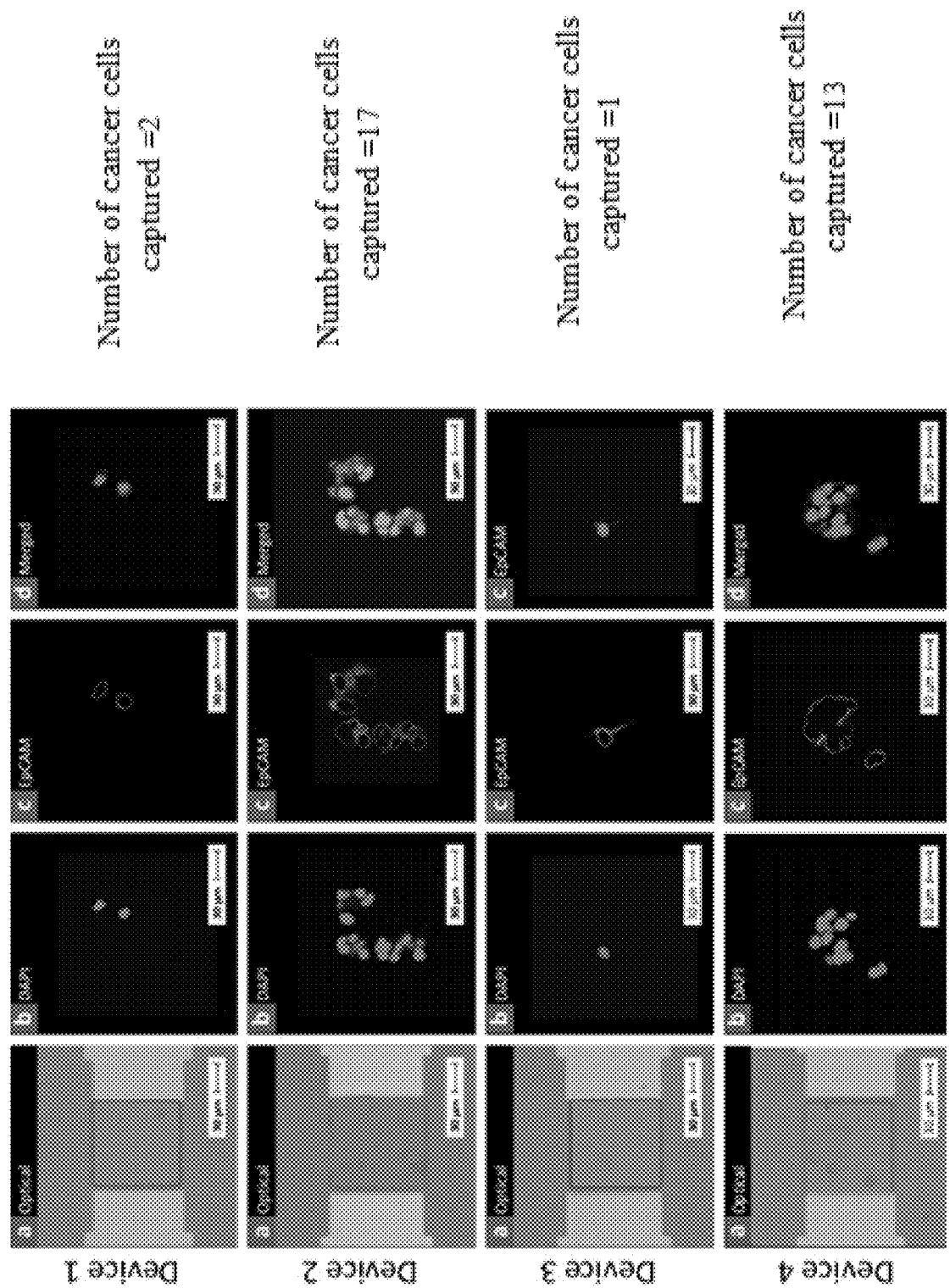

FIG. 27 presents cell capture using nanotube devices using a confocal microscope, showing representative confocal images from 6 devices imaged (4 shown) of captured cells in spiked buffy coats ranging from 1-17 cells per 5 µl sample.

Figure 28A:
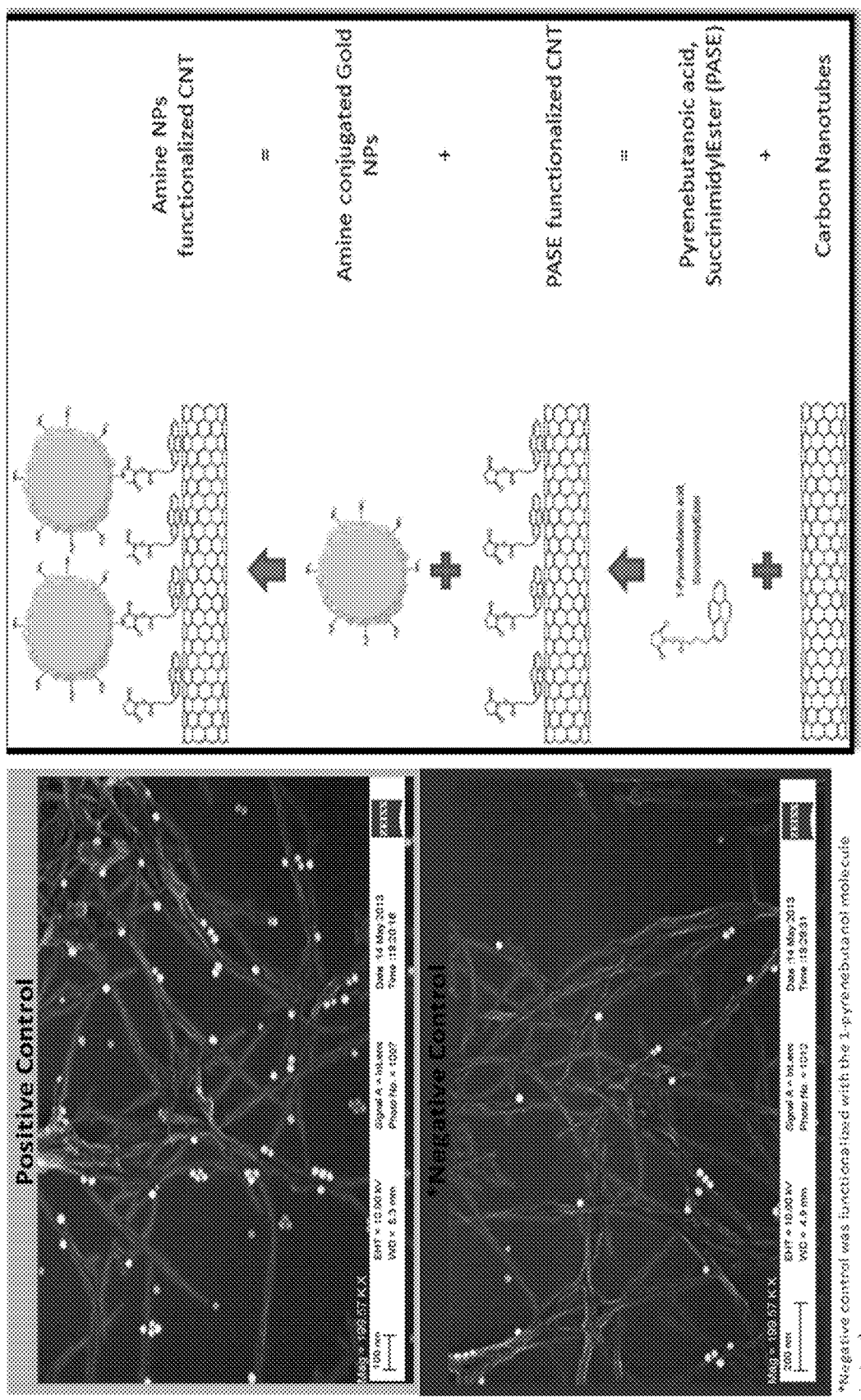

FIG. 28A presents the Amine-Au nanoparticle functionalization results.

Figure 28B:
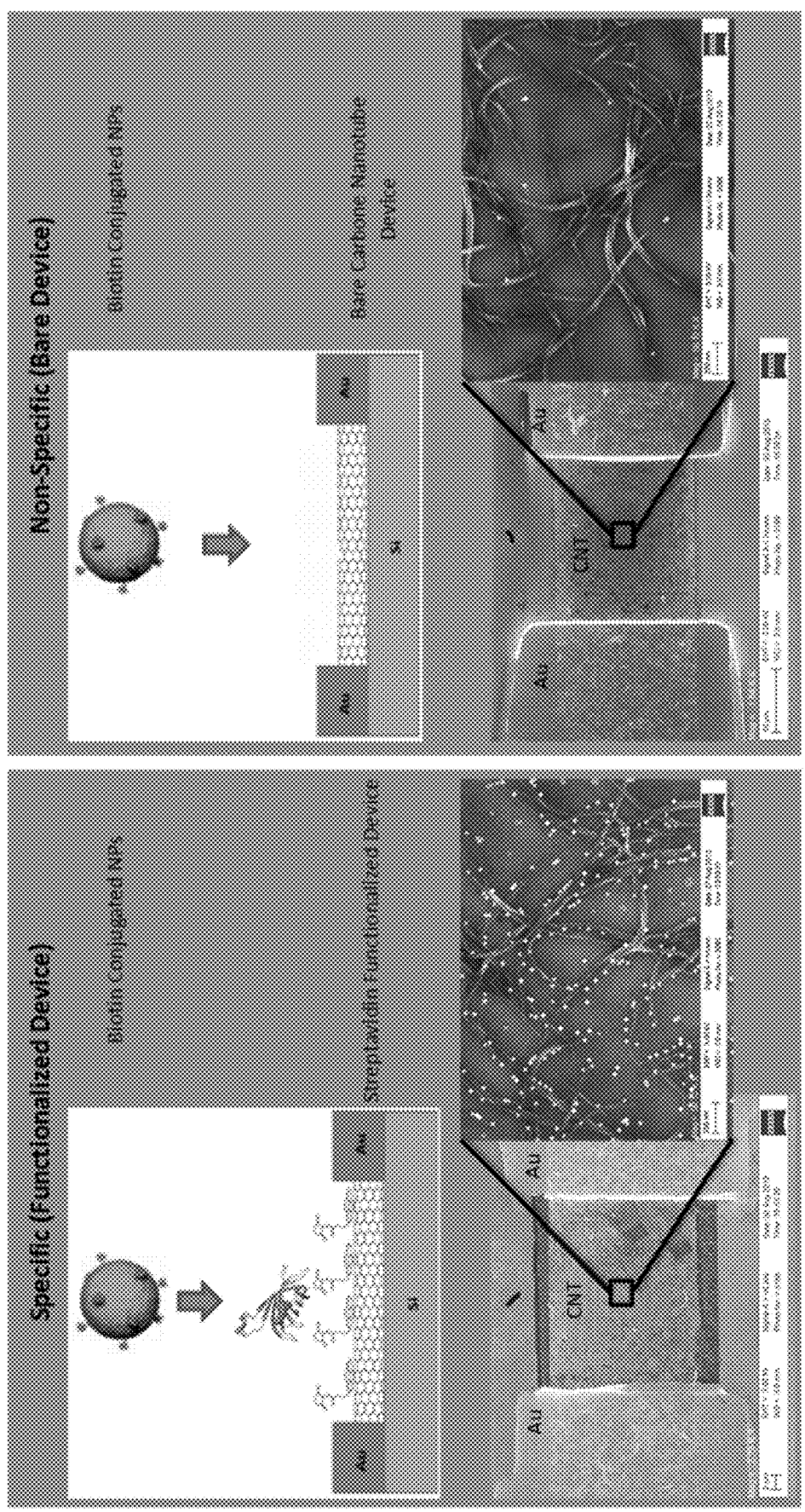

FIG. 28B presents Streptavidin-Biotin conjugation results on carbon nanotube devices.

Figure 29:
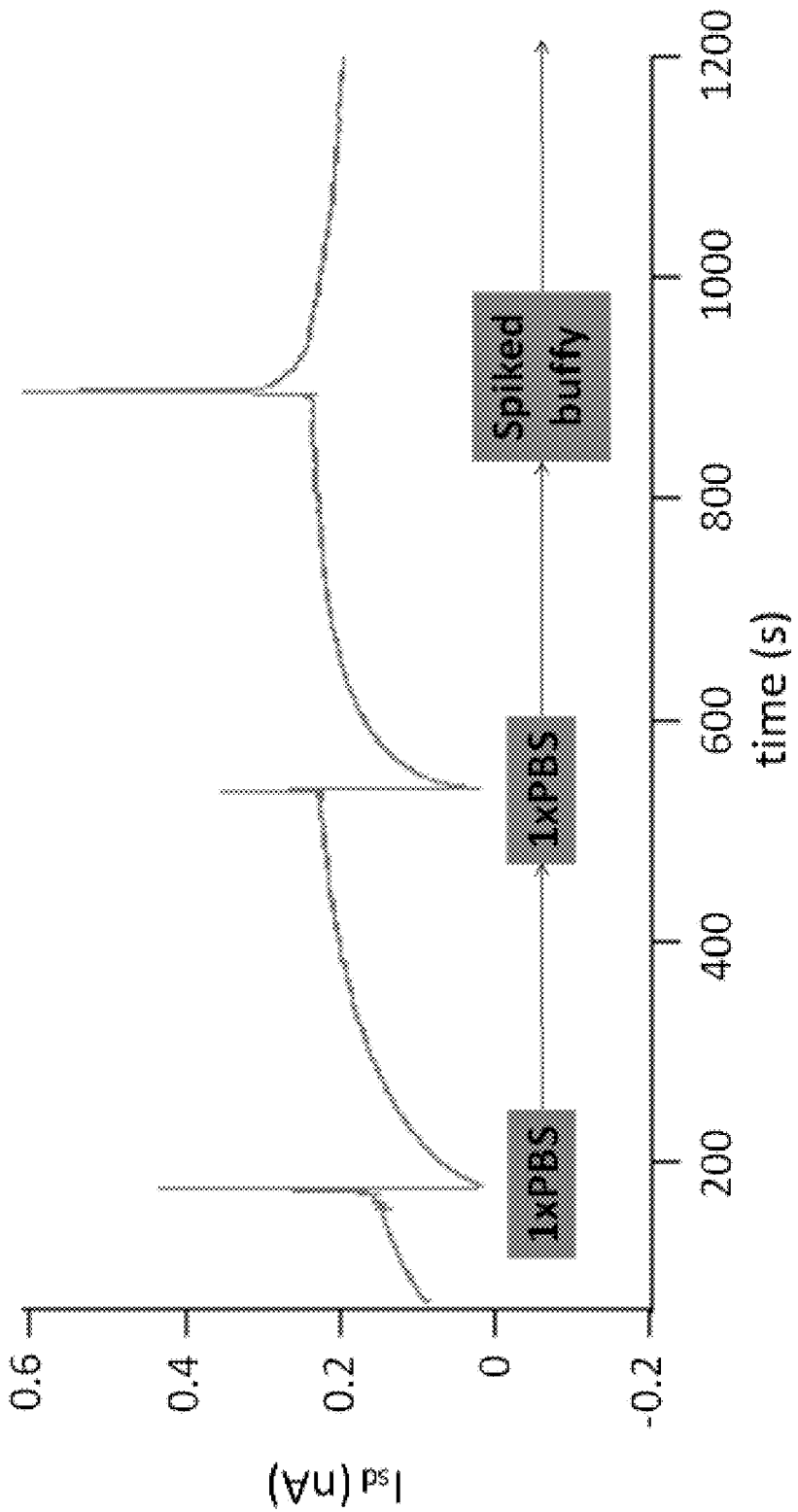
Figure 30A:
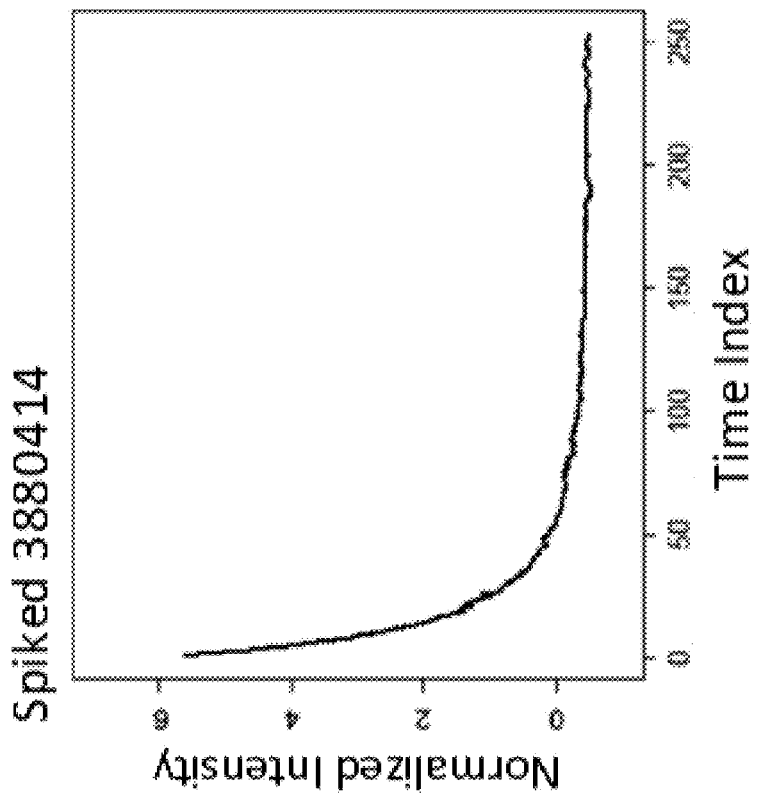
Figure 30B:
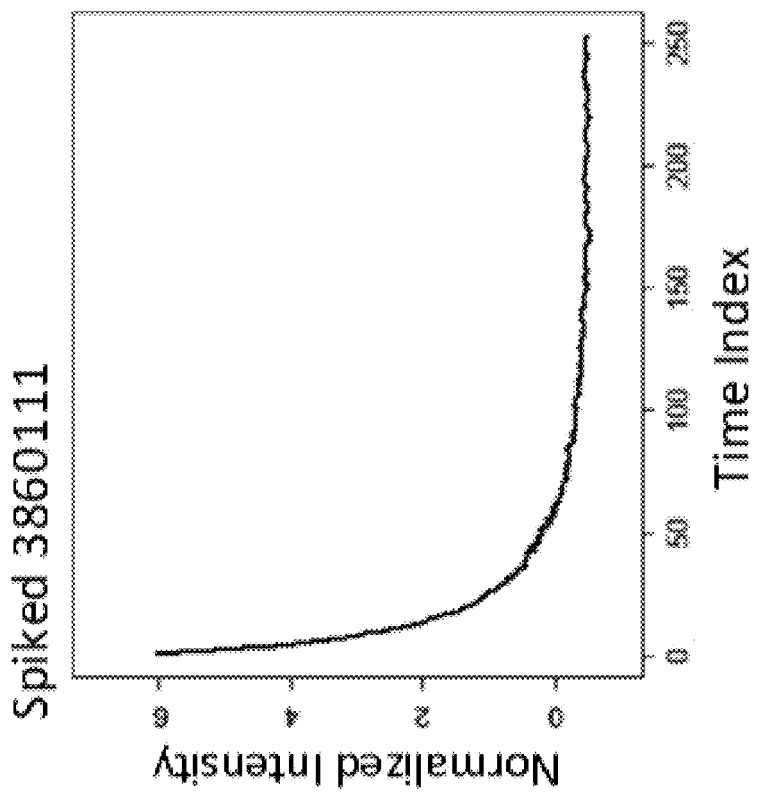
Figure 30D:
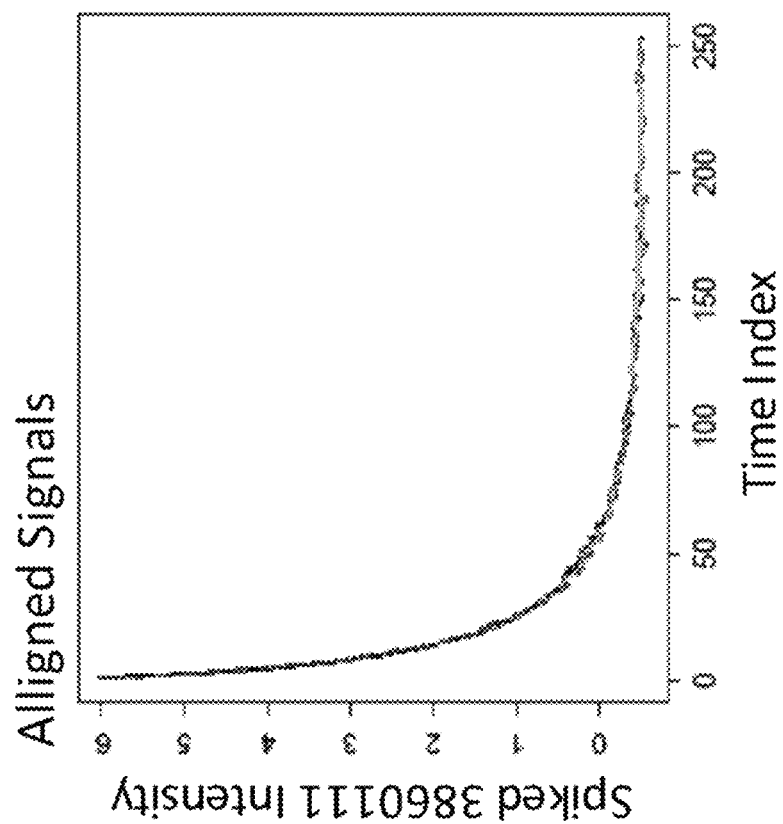
Figure 30C:
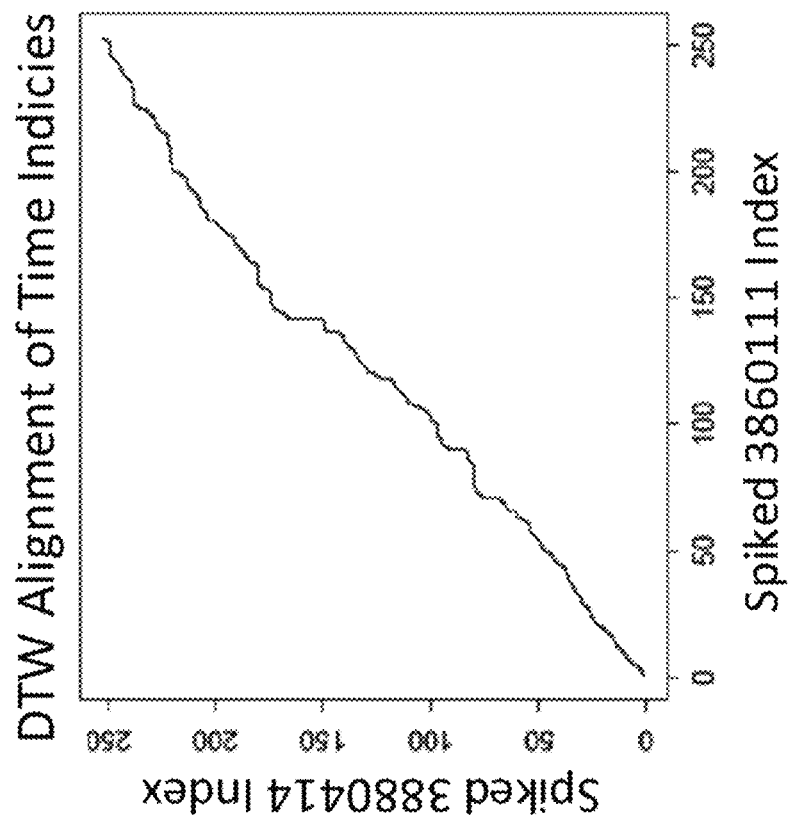
Figure 31B:
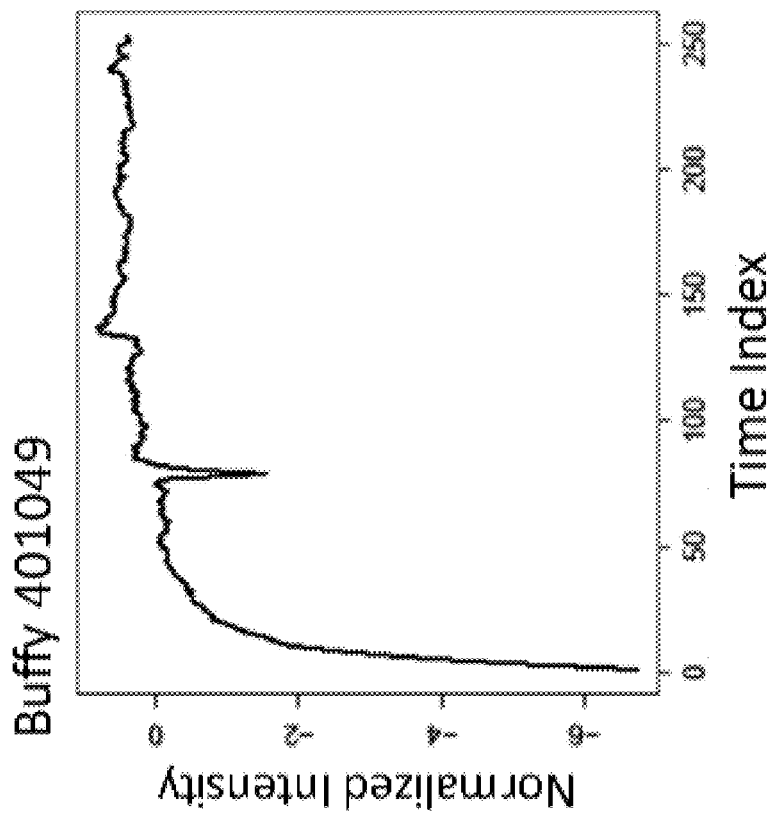
Figure 31A:
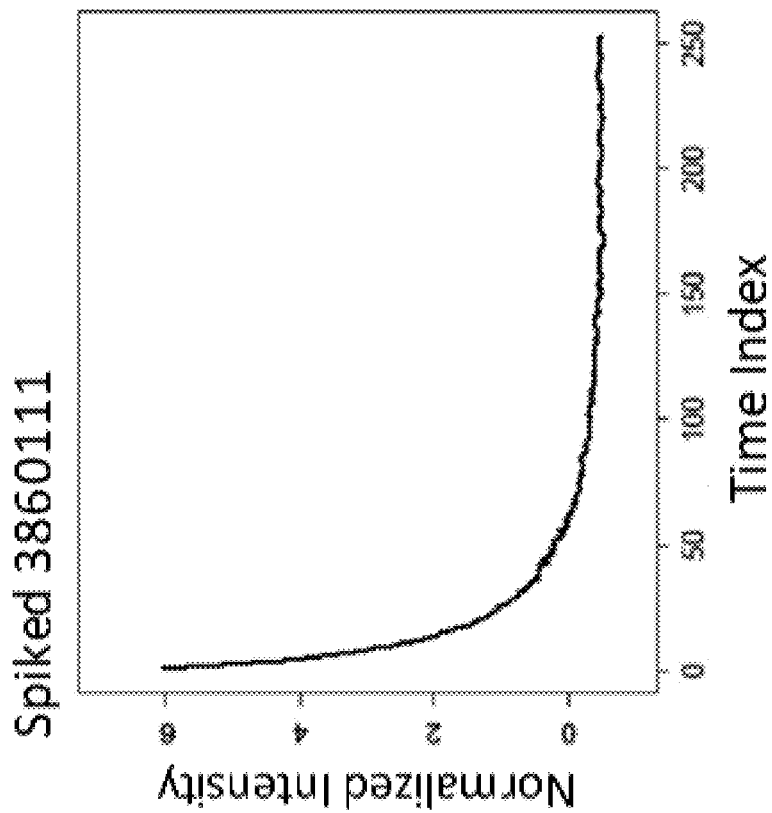
Figures 31C, 31D:
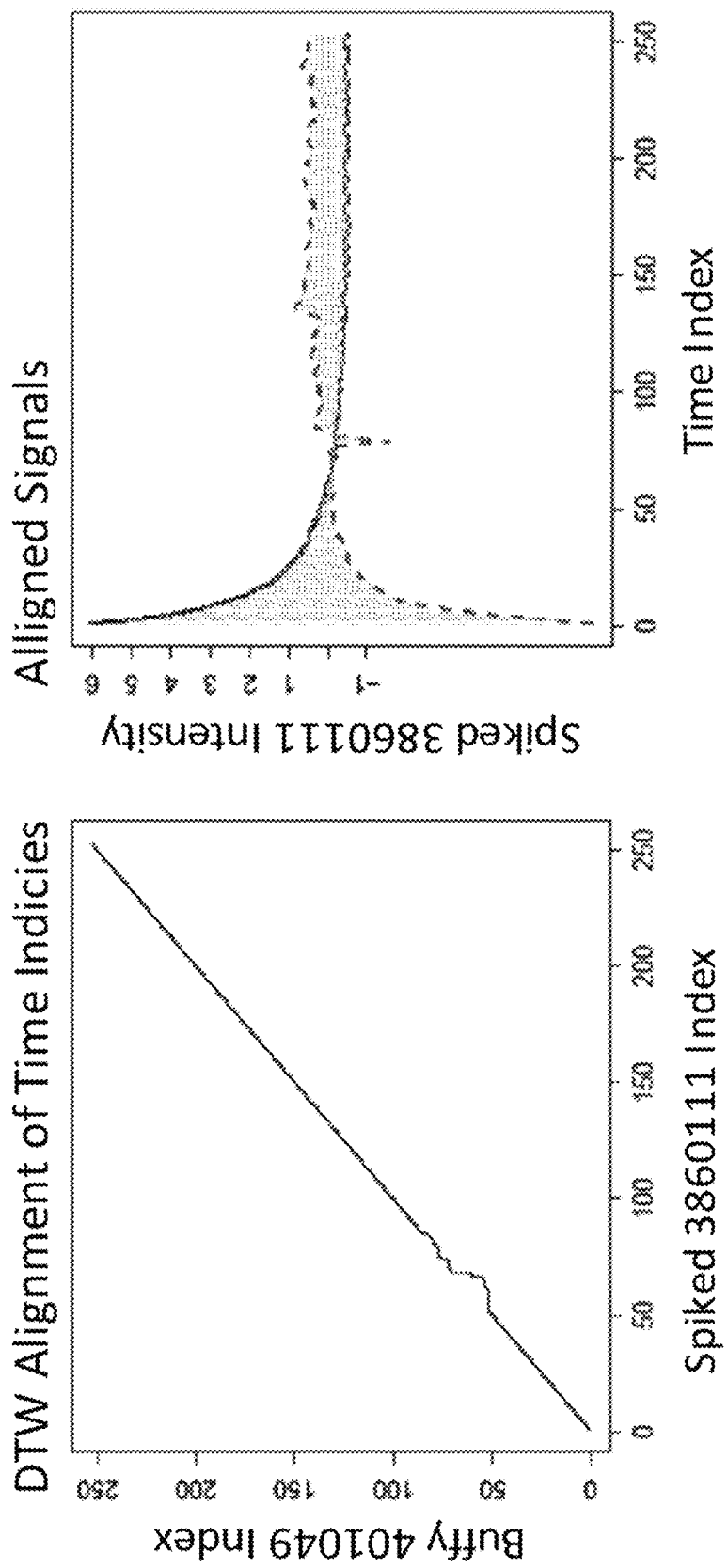

FIG. 29 presents a representative graph of the testing protocol.

FIG. 30A-FIG. 30D present two qualitatively similar spiked signals.

FIG. 31A-FIG. 31D present two qualitatively different signals from different groups of samples.

Figure 32:
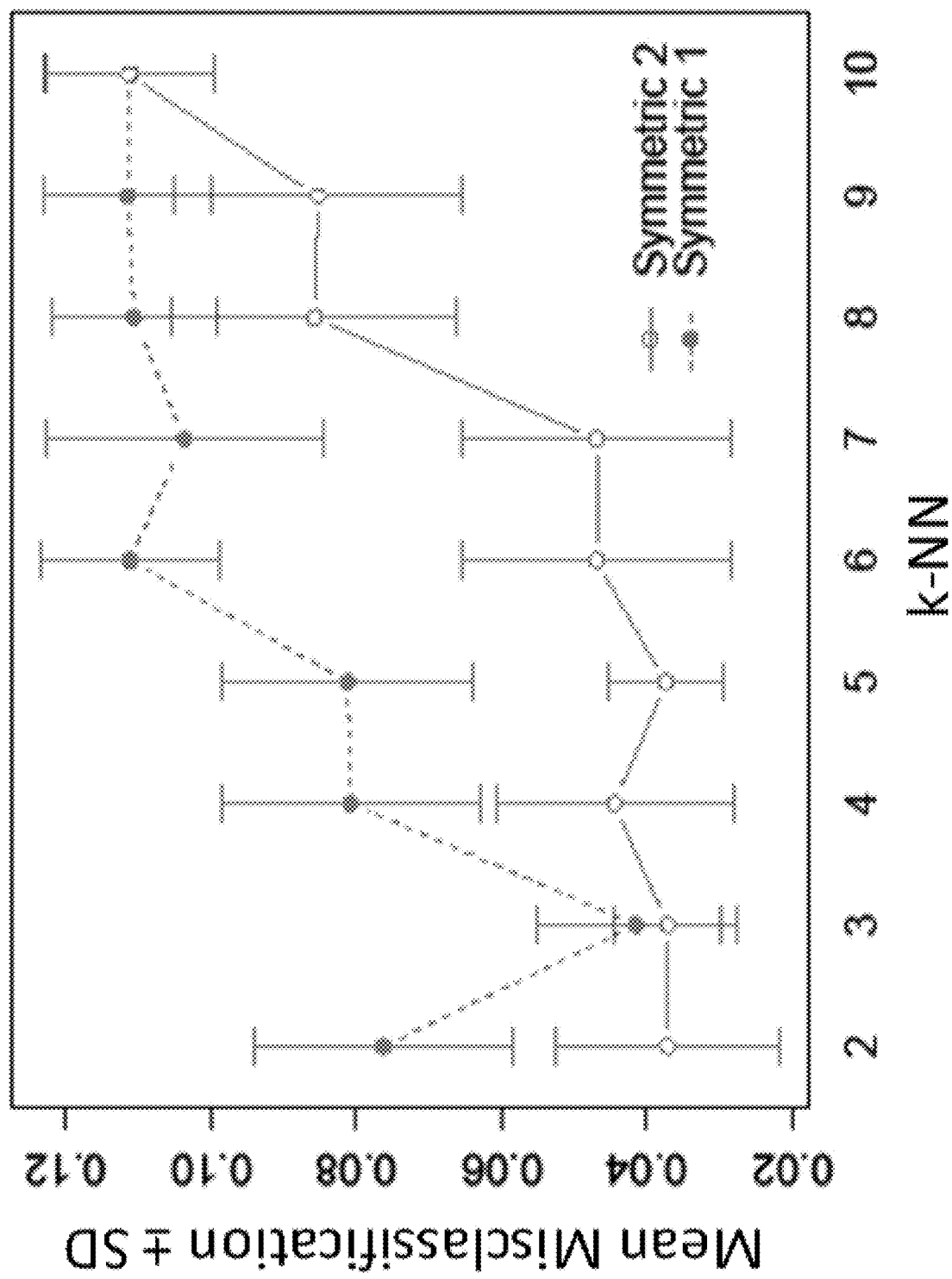

FIG. 32 presents the cross-validation results where, for each choice of k, 10,000 bootstrapped datasets were used to measure the misclassification rate.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

In some embodiments, the present disclosure provides devices and methods for static capturing, detection, isolation and counting of cellular targets from blood. In some embodiments, this can be achieved through fractionation of blood into small droplets in a micro-array format. In some embodiments, such cellular targets can comprise Circulating tumor cells (CTCs), such as breast cancer cells. In particular, the present disclosure provides devices and methods for rapid and label-free capture of breast cancer cells spiked in blood using nanotube-antibody micro-arrays. It should be noted, however, that while this disclosure describes the present devices and methods in connection with CTCs and breast cancer cells, the present devices and methods can be adapted to capture other types of cells from blood or other bodily or exogenous fluids.

In some embodiments, 76-element single wall carbon nanotube arrays may be manufactured using photo-lithography, metal deposition, and etching techniques. Anti-epithelial cell adhesion molecule (anti-EpCAM), Anti-human epithelial growth factor receptor 2 (anti-Her2) and non-specific IgG antibodies can be functionalized to the surface of the nanotube devices, for example, using 1-pyrenebutanoic acid succinimidyl ester. Following device functionalization, blood spiked with SKBR3, MCF7 and MCF10A cells (100/1000 cells per 5 μl per device, 170 elements totaling 0.85 ml of whole blood) can be adsorbed on to the nanotube device arrays, and electrical signatures may be recorded from each device to screen the samples for differences in interaction (specific or non-specific) between samples and devices. A zone classification scheme can be used to enable the classification of all 170 elements in a single map.

The present disclosure further provides a kernel-based statistical classifier for the 'liquid biopsy' to create a predictive model based on dynamic time warping series (DTW) to classify device electrical signals that correspond to plain blood (control) or SKBR3 spiked blood (case) on anti-Her2 functionalized devices with ~90% sensitivity, and 90% specificity in capture of 1000 SKBR3 breast cancer cells in blood using anti-Her2 functionalized devices. Screened devices that gave positive electrical signatures can be confirmed using optical/confocal microscopy to hold spiked cancer cells. Confocal microscopic analysis of devices that are classified to hold spiked blood based on their electrical signatures can confirm the presence of cancer cells through staining for DAPI (nuclei), cytokeratin (cancer cells) and CD45 (hematologic cells) with single cell sensitivity. The devices of the present disclosure may enable a 55-100% cancer cell capture yield. In some embodiments, such yield may depend on the active device area for blood adsorption with mean of 62% (~12,500 captured off 20,000 spiked cells in 0.1 ml blood).

The present disclosure provides the static isolation and enumeration methods that may offer one or more of the following advantages: 1) micro-array format enabling a large volume of blood to be fractionated into smaller portions that may enable better capture sensitivity and enable verifiable and reproducible results as well as the ability to scale the number of sensors; 2) the nanotube-micro-arrays include both detection and capture technology unlike microfluidics which only captures; 3) a wide variety of antibodies can be functionalized on the same nanotube micro-array that can capture CTCs overexpressing different receptors; 4) classification of the detected electrical signals using kernel-based DTW classifiers with high sensitivity and specificity; 5) transfer of cells is not required to do further microscopic analysis thereby minimizing loss of CTCs; 6) the design is tunable to capturing 1 to 80,000 individual cells/22,500 cell clusters per device by changing the ratio of the area of the active region of the pad to the droplet area; 7) the entire assembly can be automated into a compact handheld device or a laboratory based instrument similar to the immunomagnetic methods of enrichment and capture; 8) the captured cells are viable, enabling downstream molecular analysis such as qPCR.

In some embodiments, the spiked cancer cells in blood can be captured using carbon nanotube micro-arrays.

FIG. 1A presents a diagnostic chip 10 of one or more carbon nanotube (CNT) devices 12 for detection and capturing cancer cells. In some embodiments, the chip 10 can include a 76-element array of carbon nanotube devices. In this manner, the device is able to capture a large number of cells. In some embodiments, the number of elements may be increased or decreased depending on the volume of blood to be processed by the chip 10. The blood can be applied using a pipette. In some embodiments, a saline solution may be applied to the device and then the blood may be applied into the saline solution.

Figure 2A:
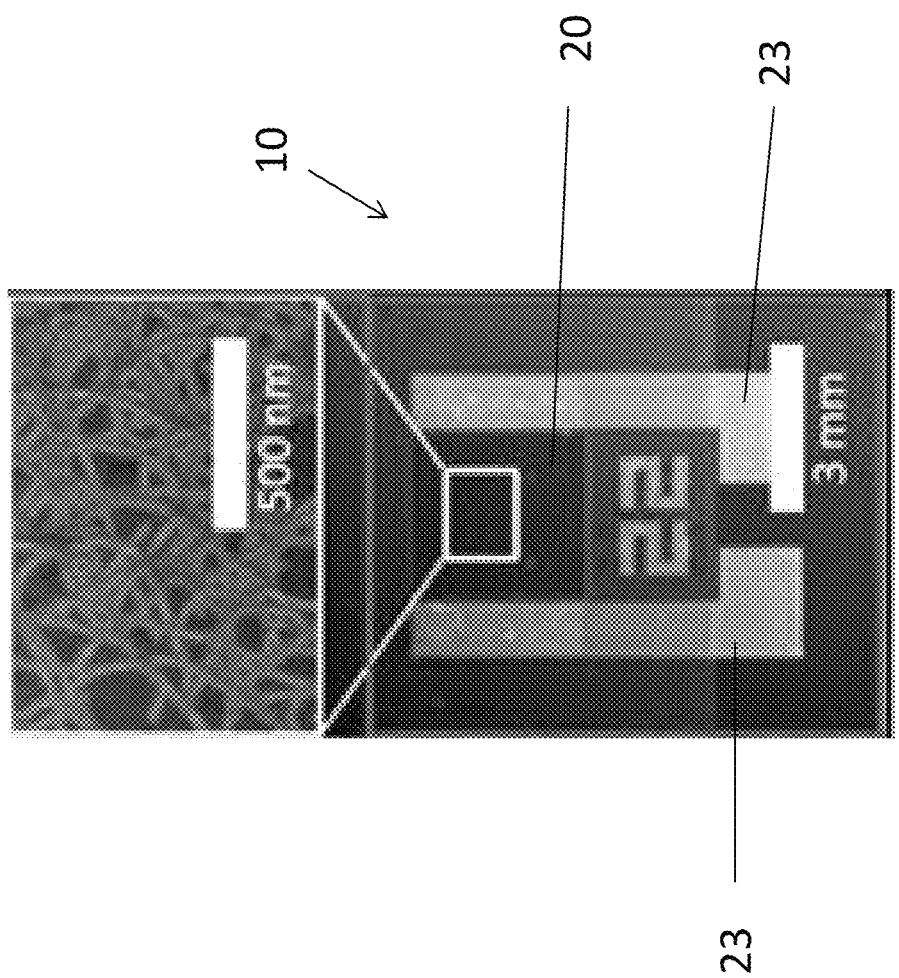
FIG. 2A presents a top view of a carbon nanotube device according to some embodiments of the present disclosure.

FIG. 2A presents a top view of a CNT device 12 of the present disclosure, showing carbon nanotube film 20 and a plurality of conductive contacts or electrodes 23.

Figure 2B:
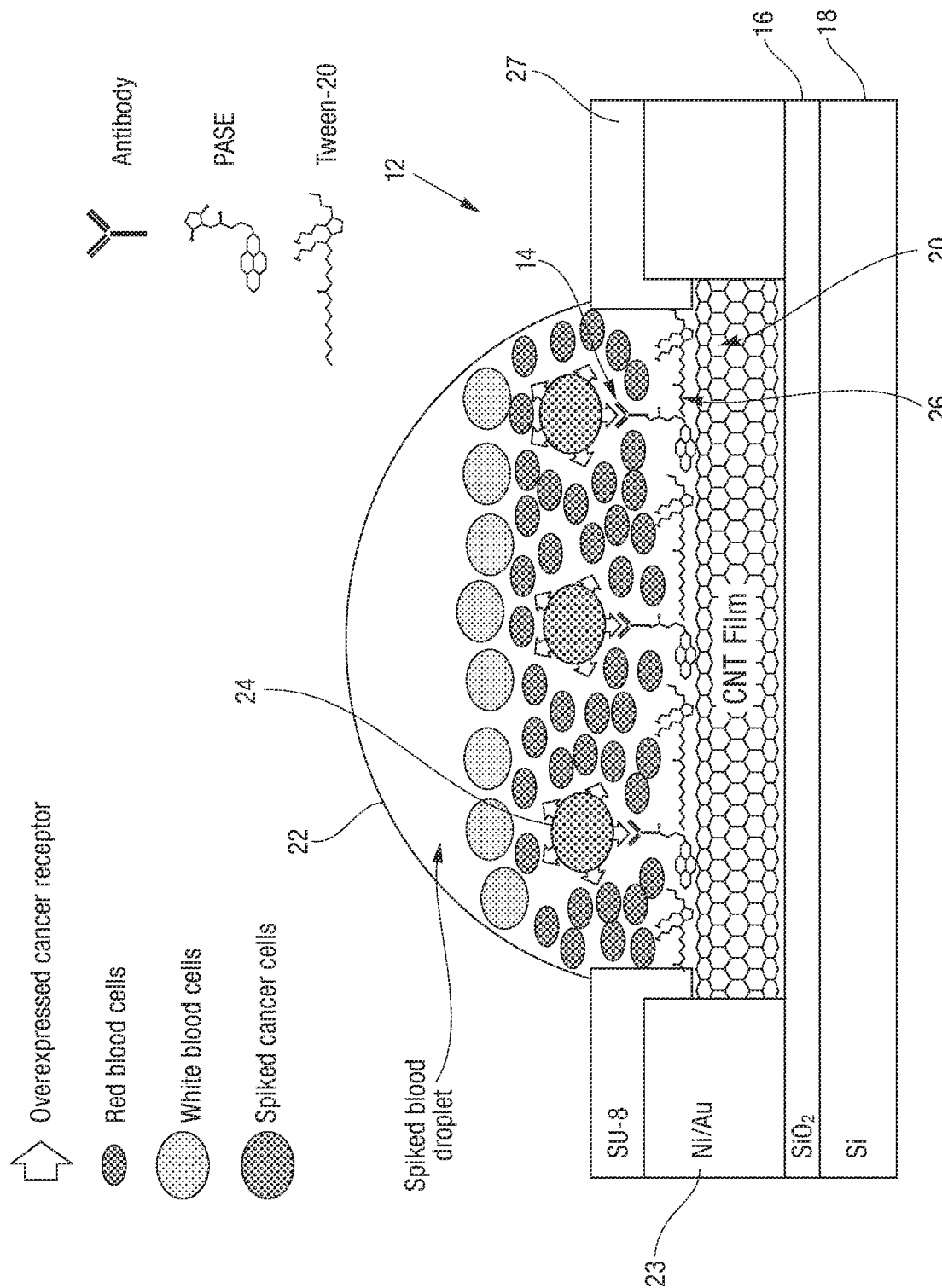
FIG. 2B and FIG. 2C present a side view of a carbon nanotube device according to some embodiments of the present disclosure.
Figure 2C:
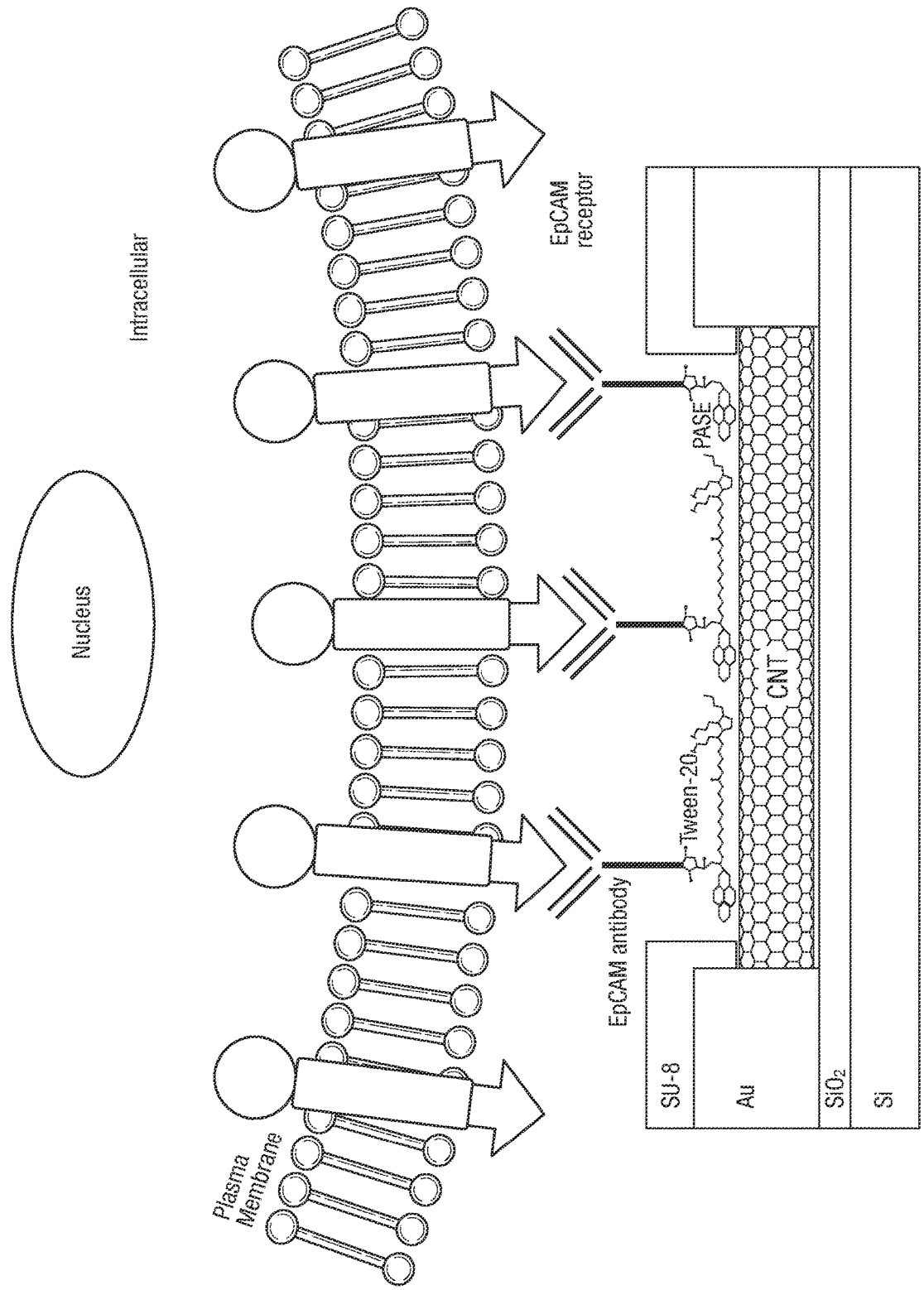

FIG. 2B and FIG. 2C present a side view of a CNT device 12 of the present disclosure. The CNT device 12 includes a carbon nanotubes (CNT) film 20 disposed on a substrate 18 with a layer of a dielectric material 16 disposed between the nanotubes film and the substrate. The CNT devices 12 of the present disclosure may be used to both detect and capture cancer cells in blood.

The CNT film 20 can act as a surface for detecting surface receptors or markers in cellular targets in bodily sources, e.g., cancer cells in blood. The CNT film 20 can be functionalized with one or more agents 14 selected for capturing the desired target. In some embodiments, the nanotubes may be functionalized with anti-epithelial-cell-adhesion-molecule (EpCAM), anti-human epithelial growth factor receptor 2 (anti-Her2) and nonspecific immunoglobin (IgG) antibodies, PSMA, EGFR, her2-neu, her1, her3, G-protein coupled receptors and combinations thereof. In some embodiments, the surface of the CNT film 12 may be functionalized with EpCAM and anti-Her2, by themselves or in combination with other capture agents. In some embodiments, a surfactant may be deposited on non-functionalized nanotubes to eliminate or at least reduce non-specific absorption of cancer cells onto the CNT film. In some embodiments, Tween-20 or sodium dodecyl benzene sulfonate may be used.

The CNT device 12 further includes the plurality of conductive contacts 23 disposed on the substrate and electrically coupled to the CNT film. When blood 22 mixed with cancer cells 24 is brought into contact with the CNT film 12 that has been functionalized with monoclonal antibodies, the conductivity of the thin film changes, and typically does so in a manner that is directly related to the number of cancer cells in blood. For example, FIG. 2C shows a cooperative binding of anti-EPCAM antibodies to their corresponding receptors in cells on top of nanotube biosensors creating increase in electrical conductance. By applying a known voltage across the CNT film through conductive contacts 23, the presence of cancer cells can be determined from the current sensed through the CNT film, with the current decreasing a function of the number of cells in the blood. Various embodiments of carbon nanotube devices useful in the currently disclosed methods are described, for example, U.S. Ser. No. 13/045,135, which is incorporated herein by reference in its entirety. In some embodiments, the CNT devices may include a passivation layer 27 (such as SU-8) to expose only the active nanotube elements. In some embodiments, the contacts may be formed from an alloy of Nickel (Ni) and Gold (Au).

In some embodiments, the CNT film 20 is formed from a single layer of semiconducting nanotubes. In some embodiments, single wall carbon nanotubes may be employed. In some embodiments, the nanotubes are highly purified having a purity of higher than 90%, or, in some embodiments, higher than 95% or higher than 99.5%. In some embodiments, the density of the nanotubes may be between 1 and 5 nanotubes per micrometer. In some embodiments, the density may be between 3 and 5 nanotubes per micrometer. In some embodiments, the density may be 5 nanotubes per micrometer. The density may be controlled through a filtration process using a known concentration of nanotubes in the starting material. In some embodiments, the nanotubes are deposited in a single layer.

In some embodiments, the nanotube-CTC-chip can use static isolation technique for the capture of CTCs. As noted above, the CNT film 20 may be functionalized with one or more antibodies to capture the cancer cells in blood. In some embodiments, the film is functionalized with 1-Pyrenebutanoic Acid Succinimidyl Ester (PASE) to conjugate one or more antibodies to the film. In some embodiments, the CNT film 20 may be chemically functionalized using sidewall PASE functionalization. The side wall functionalization enables access to the π orbitals of the carbon nanotubes. The strong π-π interactions between the pyrene fragment of the PASE molecule and the nanotube surface can creates a method for stable functionalization of carbon nanotubes. The pyrene rings of the PASE adsorb on to the sidewalls of the single wall carbon nanotube (SWNT) through π stacking and produce a stable nanotube-PASE composite. The succinimidyl ester on the other end of the PASE provides the attachment site for the antibodies. In some embodiments, the antibodies may be selected from one or more of anti-EpCAM, anti-Her2 and IgG. In some embodiments, the antibodies may include one or more of the following: EGFR, EPCAM, Her2, PSMA, and Vimentin.

In some embodiments, the CNT film may also be functionalize with metal nanoparticles, such as gold nanoparticles.

In operation, a blood sample including cancer cells can be introduced onto the diagnostic chip 10. Spiked breast cancer cells can be captured by the CNT film without pre-labeling, pre-fixation, or any other processing steps. Blood can simply be adsorbed and electrical sensing and DTW classification can enable detection and stratification. Classified devices can then be analyzed using optical/confocal microscopy on chip. The devices that give a rise in electrical signal can be classified to hold cancer cells. This is the detection. Once several devices are classified, these can then be taken for optical/confocal microscopy to see the presence of cancer cells. For confocal microscopy, the cells can be stained for DAPI, cytokeratin Ck-19 and CD45 to show they are indeed cancer cells.

In some embodiments, the present disclosure provides a method for rapid and label-free capturing of breast cancer cells in a blood sample comprising applying a blood sample onto a CNT device 12, allowing breast cancer cells in the blood sample to adsorb onto the CNT device 12, and identifying and counting breast cancer cells absorbed onto the CNT device.

In some embodiments, the present disclosure provides a method for specific detection of cancer cells in the blood sample. In some embodiments, such method may comprise applying a blood sample onto a CNT device 12, receiving an electrical signal from the CNT device, the signal being indicative of interactions between the blood sample and the CNT device, and applying a statistical method to distinguish between specific interactions and non-specific interactions. In some embodiments, a predictive model based on statistical methods, such as for example, dynamic time warping series, is provided to classify device electrical signals that correspond to specific interactions versus non-specific interactions. In some embodiments, a rise in electrical signal from the buffer level may indicate specific interactions. Non-specific interaction may be indicated by no change or decrease in electrical signal.

In the CNT devices of the present disclosure three different electrical signals can be identified: 1) the characteristic signals are classified as specific interactions that give rise to an increase in signal conductance followed by saturation at higher level of conductance; 2) non-specific interactions are characterized by a decrease in electrical signal or 3) no change in conductance, or at the same level as buffer. A statistical technique, such as a kernel-based classifier employing dynamic time warping (DTW), can be used to distinguish between specific and non-specific interaction of cancer cells which is probably better than traditional Euclidean distance metric.

Biomolecular reactions are driven thermodynamically by the reduction in free energy (G) of the system. For specific interactions, the reduction in free energy is higher than non-specific interactions. A spectrum of energy domains can be used to transduce the change in the free energy of the specific interactions into mechanics, electricity, thermal or magnetism. The measurement of specific versus non-specific binding events in cells as electrical spikes in a fast manner and the ability to stratify them rapidly in blood using dynamic time warping (DTW) enables both detection and capture on chip.

In general, $\Delta G$specific<<<$\Delta G$non-specific, with negative $\Delta G$ is favorable. Since the reduction in free energy is universal for specific and non-specific pairs, this can be used for detection of specific versus non-specific interactions in cells. In some embodiments, extracellular overexpressed receptors, namely EpCAM and Her2, in breast cancer cells can interact with the anti-EpCAM and anti-Her2 antibodies on the surface the CNT film. The cooperative specific interaction of thousands of extracellular receptors with specific antibodies on nanotube surface creates spikes in the normalized electrical conductance versus time. Capturing cells based on both EpCAM and Her2 can optimize CTC capture efficiency for breast cancer, as EpCAM expression in CTCs may be transient and dependent upon the local micro-environment, whereas the use of anti-EpCAM antibodies to target the EpCAM receptor for cell capture is an example of a specific interaction.

Non-specific samples, such as plain blood, can also create such spikes in the electrical conductance versus time data, with much lower slopes. Such spikes in the signals can carry meaningful information about the sample condition/interaction that could then be analyzed using microscopy of captured CTCs.

In some embodiments, a statistical technique can be used to classify the signatures that represented specific versus non-specific interactions. In some embodiments, a kernel-based classifier employing dynamic time warping (DTW) can be employed. In some embodiments, these can be classified with ~90% sensitivity and ~90% specificity in classifying devices specifically based on Her2 signatures for spiked SKBR3 (breast adenocarcinoma) cells in blood. In some embodiments, because an electrical signal due to specific interaction can be distinguished from an electrical signal due non-specific interactions, cancer cells can be identified in the blood sample based on their effect on CNT electrical properties. In some embodiments, the capture of cells can be based on static isolation in a micro-array format followed by microscopy on chip.

In some embodiments, the present disclosure provides a method for distinguishing between specific and non-specific interactions by creating a zone classification scheme for electrical signals due to the interactions of the blood sample with the CNT devices. For example, specific interaction can indicate an increase in the CNT device conductance whereas non-specific interaction can result in a decrease or no change in CNT device conductance. Specific interactions, such as, for example, interactions between cancer cells and the CNT film, and non-specific interactions, such as interactions between blood cells and the CNT film, can be visually classified into these three groups: 1) "Zone 1" or an increase in the device electrical signal; 2) "Zone 2" or no change and 3) "Zone 3", decrease in device electrical signal. Using the zone classification, all data can be viewed in a single map. In some embodiments, when 10 devices are tested using 1 antibody and if 3 devices give rise to increase in signal, then microscopy can be conducted on all 10 samples to count the presence of cancer cells. However, the number of positive results may be more than 3 or fewer than 3.

In some embodiments, the testing platform can be set up on Signatone probe station. An Agilent 4156C semiconductor parameter analyzer equipped with a custom LabVIEW interface can be used for monitoring the sensors and data collection. A 100 mV DC bias can be applied to source electrodes and 0 V VG can be applied using a Ag/AgCl reference electrode via the sample droplet. The source-drain current, ISD, can be recorded for the duration of the test. The accuracy of the semiconductor parameter analyzer can be set to 1 fA. The entire probe station assembly can be placed on an optical table that is vibration isolated using air on all four legs. A metal box can cover the entire assembly to avoid electromagnetic interference. The probes can be connected to the parameter analyzer using a triaxial cable that is EM shielded. Throughout the testing the devices can be maintained inside a humidified chamber to prevent evaporation of the sample droplet. The testing protocol can start with a hydrated device topped by a 20 µl droplet of 1×PBS, which can be placed immediately after functionalization. The bias can be applied, and the sensor can be monitored for the initial 4 min, then 5 µl droplets of the sample solution, plain or spiked blood, can be pipetted directly into the standing 20 µl 1×PBS droplets. Devices can be monitored for 360 seconds after addition of the sample solution. The total duration of one test can be 10 minutes long. To compare results among devices, ISD data can be normalized to obtain the G/G0 values for conductance. The sensor element can also be imaged on an optical microscope to confirm the presence of cancer cells. The spiked donor blood samples can consist of 100 or 1000 MCF7/SKBR3/MCF10A cells per 5 µl per device for these experiments. The surface of the CNT device can interact with over 20 000 cells at one time, therefore fully capable of capturing 1000 or 100 spiked cells. Using electrical station with parameter analyzers may increase precision of the tests. It should be noted that other test methods and set up protocols may be used.

In some embodiments, the present disclosure provides a method for collecting and counting cells in a blood sample comprising applying a blood sample onto a CNT device 12, allowing the blood sample to settle, and identifying and counting cells of preselected type in the blood sample.

As shown in FIG. 2B, when a blood sample is applied onto the CNT device 12, various blood cell types in the sample settle differentially due to the forces of gravity and surface texture and charge, resulting in cells coming in contact and interacting with the carbon nanotube surface. Due to the hydrophobicity of nanotube film, the blood droplet may be localized on the device creating a layer of plasma and white blood cells on the top layer and red blood cells and cancer cells in the bottom. Once the various cells in the blood sample differentially settled, they can be identified and counted using, for example, microscopy. As necessary, the top level of plasma and white blood cells can be removed to count the cancer cells. In some embodiments, the size of the droplet and the size of the active area of the device and the hydrophobicity of the CNT film can be varied to determine the cell capture efficiency. In some embodiments, the size of droplet may range between 3 mm to 5 mm. In some embodiments, the contact angle of the nanotubes is between 105-140 degrees. The ratio between the areas can enable tunable design of devices to capture a specific number of cells both in large and small volumes. For example, by changing the ratio of the pad area to droplet area, the capture of cells can be tuned. It is the droplet area to the device area which matters. In some embodiments, the ratio may be between 0.5 to 1.0, which may result in between 50% to 100% capture. In some embodiments, capture yield can be controlled by changing the area of the pad to the area of the droplet. In some embodiments, the hydrophobicity of the film may be further enhanced by including one or more fluoro carbon polymers with the film. In some embodiments, one or more carboxylic acids can be applied on the film to change hydrophobicity of the film.

Figure 3E:
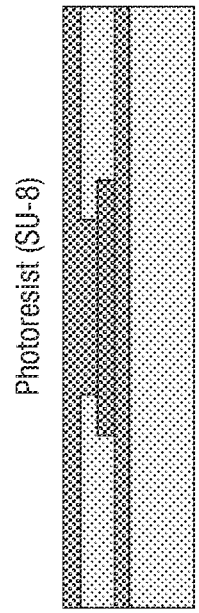
Figure 3G:
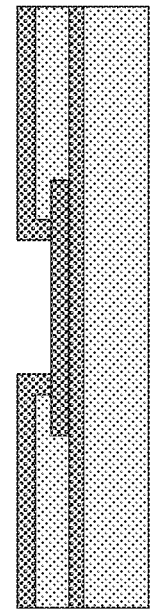
Figure 3F:
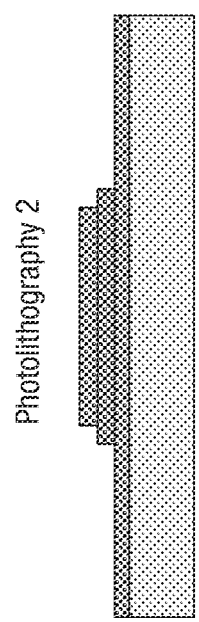
Figure 3H:
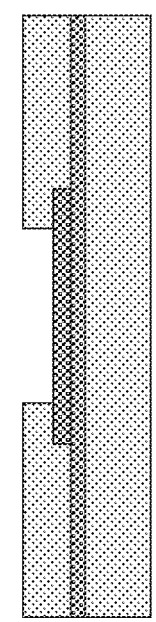

CNTs device 12 of the present disclosure can be prepared by a variety of manufacturing methods. FIG. 3A-FIG. 3H presents a non-limiting example of one such fabrication process, but other processes known in the art can also be used. FIG. 3A shows a 4" silicon wafer. FIG. 3B shows dry-thermal oxidation. FIG. 3C shows the CNT film transfer. FIG. 3D presents the first photolithography step followed by patterning CNT film, and Reactive-ion etching. FIG. 3E shows the second photolithography for patterning electrodes. FIG. 3F shows the sputtering Ni/Au and lift-off. FIG. 3G shows how the SU-8 photoresist is spun on top of wafer. FIG. 3H shows how the third photolithography step is performed to open window through SU-8 layer and expose the sensor surface. In some embodiments, 76 element array of 3 mm×3 mm devices is provided, where one can capture 1000 cells per device. Different number of arrays and devices of different size can be provided. In some embodiments, a highly specific PASE functionalization protocol is used that enables antibodies to attach specifically to the nanotubes. In some embodiments, Tween-20 is used after antibody functionalization to cover the uncoated nanotubes to avoid non-specific adsorption, so the present devices are highly specific. In some embodiments, 5-20 micro-litters of blood can be used per device. The total volume tested can be 0.85 ml. In some embodiment, all nanotubes are semiconducting nanotubes. In some embodiments, only a single layer of nanotubes is created on the surface. In some embodiments, the nanotubes are highly purified semiconducting nanotubes. This is suitable for PASE-antibody functionalization as PASE interacts with semiconducting nanotubes better than metallic nanotubes, making the devices highly specific. In some embodiments, optical microscopy can be used to identify cancer cells settle to the bottom and white blood cells settle at the top. The device architecture and hydrophobic nature of nanotubes enables differential settling there by resulting in cancer cells going to the bottom versus white blood cells settling on top, which can facilitate the capture of cells. In some embodiments, the electrical signals can be classified using a zone classification scheme where the electrical signals increase, stay at the buffer level or decrease. Using the zone classification, all data can be viewed in a single map. This will be useful in clinic. When 10 devices are tested using 1 antibody and if 3 devices give rise to increase in signal, then microscopy can be conducted on all 10 samples to count the presence of cancer cells. In some embodiments, in some methods, the present devices due to the large area of the device can enable capture of up to 80,000 cancer cells from blood. In some embodiments, DTW classification can be used to cluster electrical signals from samples overexpressing Her2 in cells in blood. In some embodiments, the present devices and methods enable identification of cancer cells from leukocytes in the blood using confocal microscopy. In some embodiments, the devices were completely shielded electromagnetically while testing. In some embodiments, cell capture yield per device and also over 20 devices can be identified. The yield is 55-100% per device, with mean of 62% over 20 devices. In some embodiments, cells separation can be achieved based on her2, which signals aggressive breast cancer can be removed from the array. In some embodiment, the methods include use of DTW and designed heatmaps that show the signals and sample condition.

The devices and methods of the present disclosure are described in the following Examples, which are set forth to aid in the understanding of the disclosure, and should not be construed to limit in any way the scope of the disclosure as defined in the claims which follow thereafter. The following examples are put forth so as to provide those of ordinary skill in the art with a complete disclosure and description of how to make and use the embodiments of the present disclosure, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for.

EXAMPLES

Example 1: Capture of Spiked Breast Cancer Cells

CNT-Network Formation

Iso-semiconducting single wall carbon nanotubes were purchased from Nanointegris LLC. The manufacturer specified diameter was in the range of 1.2 nm to 1.7 nm and length was in the range of 100 nm to 4 am. Nanotubes were suspended in surfactant solution at 1 mg/100 ml as received. 600 µL of the stock solution was then mixed with 85 ml of DI water and 15 ml of 1% w/v sodium dodecyl sulfate (Sigma-Aldrich, Cat. No. 436143), for a final concentration of 6 µg/100 ml.

Vacuum Filtration

The 100 ml solution was vacuum filtered over a cellulose membrane, 0.05 µm pore size (Millipore, No. VMWP09025). The vacuum filtration method self-regulates the deposition rate of nanotubes on the membrane to produce an evenly distributed conductive network. The CNT film network was then pressed onto a dry oxidized (300 nm thickness) 4" silicon wafer for 30 min. Next the wafer was transferred to an acetone vapor bath that dissolved the overlaying filter membrane.

Clean Room Processing

Patterning of the nanotube film and electrode and insulating layer fabrication were done by photolithography in the cleanroom. The S1813 photoresist was used to mask the nanotube film areas needed for the sensor elements. Exposed nanotubes were etched away in a March reactive ion etcher for 90 s at 200 W power and 10% $O_2$. The S1813 photoresist was also used to mask the electrode pattern. Electrodes, 15 nm Ni and a 90 nm Au layers, were deposited by sputtering in a Leskar PVD 75 system, 300 W DC power. The lift-off process was conducted in an acetone bath to remove the excess Ni/Au layers. Lastly, the sensors were covered with SU8-2005, a 5 µm thick photopolymer layer. A window over each of the nanotube sensor elements was developed, but the electrodes remained insulated beneath the SU8.

Device Functionalization

Finished carbon nanotube sensors were functionalized with anti-EpCAM, anti-Her2 and IgG by a pyrene linker molecule. The pyrene rings of 1-pyrenebutanoic acid, succinimidyl ester adsorb onto carbon nanotube sidewalls by it-stacking. The ester on the other end of the molecule provided an attachment point for antibodies. PASE (AnaSpec, Cat. No. 81238) was dissolved in methanol at 1 mM. Devices were incubated in the PASE solution for 2 h at room temperature, and then rinsed with methanol and dried using a nitrogen air gun. Devices were then incubated in Anti-EpCAM (EMD Bioscience, Cat. No. OP187), anti-HER-2 (Cell Signaling tech., Cat. No 2242S), or IgG (EMD Millipore, Cat. No. 411550), 20 µg ml$^{-1}$ in 1×PBS, for 2 h at room temperature. After incubation, devices were rinsed in 1×PBS three times. Tween20 was used to block unfunctionalized nanotube sidewalls to minimize non-specific interactions. Devices were incubated with 0.5% Tween20 for 2 h at room temperature. After incubation, devices were rinsed with 1×PBS, then incubated in 20 µl droplets of 1×PBS overnight in a humid chamber at 4° C. before testing.

Cell Culture and Preparation

The breast adenocarcinoma cell lines MCF7 and SKBR3 (ATCC, Cat. No. HTB-22; HTB-30), were cultured under conditions as recommended by ATCC. MCF10A (ATCC, Cat. No. CRL-10317) is a non-tumorigenic cell line that is EpCAM negative, while MCF7 and SKBR3 are EpCAM positive cell lines. SKBR3 is a Her2 positive cell line. Cells were grown for 3-4 days to reach ~80% confluence (FIG. 15A and FIG. 15B). Cells were then detached from the culture flask using Accutase enzyme solution (Sigma, Cat. No. A6964), centrifuged and suspended in 1×PBS buffer solution and taken for counting using a hemocytometer as presented in FIG. 17A-FIG. 17D. Finally cells for each cell line were prepared at fixed concentrations of 800,000 cells/mL and 80,000 cells/mL in 1×PBS solution. Next the cell samples were diluted 1:3 in blood for a final spiked cell concentration of 1000 cells/5 µL and 100 cells/5 µL. At this stage spiked blood samples were stored at 4° C. for same day testing. As test samples were injected onto the device at fixed volumes of 5 µL, the total number of the spiked cells injected to each device was fixed at 1000 or 100 accordingly.

FIG. 17A, FIG. 17B, and FIG. 17C present optical microscope images showing the cells cultured at ~80% confluency. FIG. 17D shows an optical microscope image of the detached SKBR-3 cells. Cells are detached at this point to be counted and prepared for testing.

Blood Sample Preparation

Blood was donated by a single donor and was the subject of all blood draws. Blood samples used are all traced back to the same donor as the only source and sole blood donor. This allowed for a control and identified blood source with the least degree of variation in each batch of blood samples. The following protocol was developed to collect and handle blood samples for the purposes of the experiments presented here. As the blood sample volume defined for each set of testing are set at 5 µL, the total blood volume needed for each day of testing did not exceed 100 µL. Therefore, the blood draw protocol was generated around the volumes needed to minimize biohazardous waste generation and to maintain the health of the blood donor as the blood draws had to be executed frequently throughout the 21 days of testing. As a result, capillary sampling protocol provided by World Health Organization (WHO), "WHO guidelines on drawing blood: best practices in phlebotomy", was adopted to generate a protocol to collect blood samples from a finger tip of the subject. PBS or CTC spiked PBS were diluted 1:3 into collected blood, as described above. This dilution protocol prevented the blood from clotting without the addition of any additional chemicals and allowed for determining an exact concentration of spiked CTCs levels in each sample.

Confocal Microscopy

After experimental data had been collected, the devices were saved and taken for staining and confocal imaging. The devices were first rinsed with PBS to remove excess cells and fragments and then incubated with 4% paraformaldehyde (Santa Cruz Biotechnology Inc., Cat. No. sc-281692). After initial preparation devices were stained with DAPI (Molecular Probes, Cat. No. D1306), anti-cytokeratin (CK19) (Santa Cruz Biotechnology Inc., Cat. No. sc-33119) and anti-CD45 (Santa Cruz Biotechnology Inc., Cat. No. sc-1187) according to the standard confocal staining protocol. A coverslip was placed on top of each device and sealed before imaging. Confocal laser scanning microscopy images were obtained on a Nikon Eclipse T. with coverslip corrected objective focused at 600×.

Device Testing

The testing platform was set up on Signatone probe station. An Agilent 4156C Semiconductor Parameter Analyzer equipped with a custom LabVIEW interface was used for monitoring the sensors and data collection. A 100 mV bias was applied to source electrodes and 0 V $V_G$ was applied using a Ag/AgCl reference electrode via the sample droplet, The source-drain current, $I_{SD}$, was recorded for the duration of the test. The accuracy of the semiconductor parameter analyzer is 1 fA. The entire probe station assembly was placed on an optical table that was vibration isolated using air on all four legs. A metal box covered the entire assembly to avoid electromagnetic interference. The probes were connected to the parameter analyzer using a triaxial cable that is EM shielded. Throughout the testing the devices were maintained inside a humidified chamber to prevent evaporation of the sample droplet. The testing protocol started with a hydrated device topped by a 20 µl droplet of 1×PBS, which was placed immediately after functionalization. The bias was applied, and the sensor was monitored for the initial 4 min, then µL droplets of the sample solution, plain or spiked blood, were pipetted directly into the standing 20 µL 1×PBS droplets. Devices were monitored for 360 seconds after addition of the sample solution. The total duration of one test was 10 minutes long. To compare results among devices, $I_{SD}$ data were normalized to obtain the $G/G_0$ values for conductance. The sensor element was also imaged on an optical microscope to confirm the presence of cancer cells. The spiked donor blood samples consisted of 100 or 1000 MCF7/SKBR3/MCF10A cells per 5 µl per device for these experiments. The surface of the CNT device is capable of interacting with over 20,000 cells at one time, therefore fully capable of capturing 1,000 or 100 spiked cells.

Statistical Classifier

Statistical classification was done using DTW package in R. The sensitivity, specificity, and misclassification rate were then computed, considering spiked blood to be a positive test and normal blood to be a negative test. Sensitivity is defined as $TP/P_c$ where TP denotes the number of positive test outcomes, and P denotes the number of true positives. Specificity is defined as $TN/N_s$ where TN denotes the number of negative test outcomes, and N denotes the number of true negatives.

Arrays

The arrays can be fabricated using lithography, reactive ion etching and post-processing. With a 3 mm×3 mm device size and at the rate of 5-20 µl per device, the 76-element arrays can process anywhere from ~0.3 ml to 4.8 ml of blood, large enough to get meaningful information about the sample condition. A total of ~0.85 ml of blood and 170 elements, each analyzing 5 µl per device, was used in order to get a variety of information from this array using different antibodies. A drop of 5-30 µl was expected to contain 1-9,000 epithelial cells. It has also been reported that 1 g of tumor tissue (109 cells) sheds about 3-4×106 tumor cells into the blood stream per day and thus presents clinical value in their enumeration. The spike concentration of cells was chosen to be relevant to the upper limit of clinical samples, and as a proof of concept of this static isolation approach. The surface of the CNT device is capable of capturing over 80,000 individual cells/22,500 cell clusters at one time, therefore fully capable of capturing 100-1,000 spiked cells. Similarly, arrays can be automated to handle more than 100 elements at the same time to enable results within minutes.

The chip consisting of the 76-element array of CNT micro devices was specifically designed for the need to process large volumes of blood. Each device in the 76-element array was 3 mm×3 mm and can hold about 20 µl of blood. The 76-element device included a simple two-terminal design at their core with a CNT ultra-thin film network connecting the source and drain electrodes. In this design, the sensing channel consists of a CNT network connecting the two electrodes, 3000 µm in length and 3000 µm in width. As a result, the sensing area of each device is $9×10^6$ µm2, allowing for ~80,000 cells, assuming an average 10-12 µm diameter, to be captured on the device.

The 76-element array of nanotube devices used for the testing in blood were fabricated using a 6 µg CNT film. Past devices on 60-element arrays were fabricated using 4 µg film with an active area of 100 m×80 µm which gave a uniform distribution of the CNT network. A higher relative film concentration was selected for the 76-element array devices with respect to the device size, 3 mm×3 mm, to maintain a uniform, continuous, and conductive CNT network. The nanotube elements were highly purified semiconducting CNT (Iso-semiconducting nanotubes, NanoIntegris LLC). The CNT devices had an average resistance of 0.2 MΩ after annealing, and average mobility was calculated for these thin film devices as ~4.95 cm$^2$/V-s, with a bandgap of 0.26-0.5 eV. The on-off ratio was determined for these devices using both back-gating configuration, $I_{on}/I_{off}$=11.2 (FIG. 9A and FIG. 9B), and also with electrolyte liquid-gating configuration $I_{on}/I_{off}$=134 (FIG. 9A and FIG. 9B). The on-off ratio decreases with increasing CNT mass and the mobility increases. The results show that there is an inherent trade-off between the on-off ratio and mobilities with increasing CNT mass, which suggest high quality of nanotubes and thin film transistor characteristics, in line with previous reports.

Chemical Functionalization

Carbon nanotubes that are highly compatible with functionalization chemistry are used to manufacture these devices. The nanotube device elements are chemically functionalized using sidewall PASE functionalization. The side wall functionalization enables access to the π orbitals of the carbon nanotubes. The strong π-π interactions between the pyrene fragment of the PASE molecule and the nanotube surface creates a method for stable functionalization of carbon nanotubes. The pyrene rings of the PASE adsorb on to the sidewalls of the single wall carbon nanotube (SWNT) through π stacking and produce a stable nanotube-PASE composite. The succinimidyl ester on the other end of the PASE provides the attachment site for the antibodies. Pyrene interacts strongly with the surface of carbon nanotubes of different chiralities, but the interaction with zigzag nanotubes (semiconducting) is stronger than with armchair (metallic) ones of the same diameter. The same functionalization method for antibody functionalization and testing in blood is used. Overall, the PASE enables sidewall functionalization, the ester provides attachment to the antibodies and enables stability over many weeks. Functionalized devices can be kept at 4° C. for 1-2 weeks and still maintain the integrity of the functionalization process.

Design of Experiments

There are two main variables within the design of experiment in the array, sample type (plain blood and blood spiked with MCF7 (mammary gland adenocarcinoma), MCF10A (normal human mammary cells), or SKBR3 (mammary gland adenocarcinoma) cells and device type (IgG, anti-HER-2, or anti-EpCAM antibody functionalized device). In addition, two cell concentrations were defined for each cell spiked sample type, 100 or 1000 cells per 5 μl.

MCF-7 spiked blood vs. EpCAM functionalized CNT device, both at 100 and 1000 cell concentrations), with 40 overall replicates, shown in Table 1. Thirteen other combinations were designed as negative controls (not spiked) or positive controls with non-specific interactions expected (SKBR-3 spiked blood vs IgG).

Electrical Detection and Zone Classification Scheme

Figures 4A, 4B:
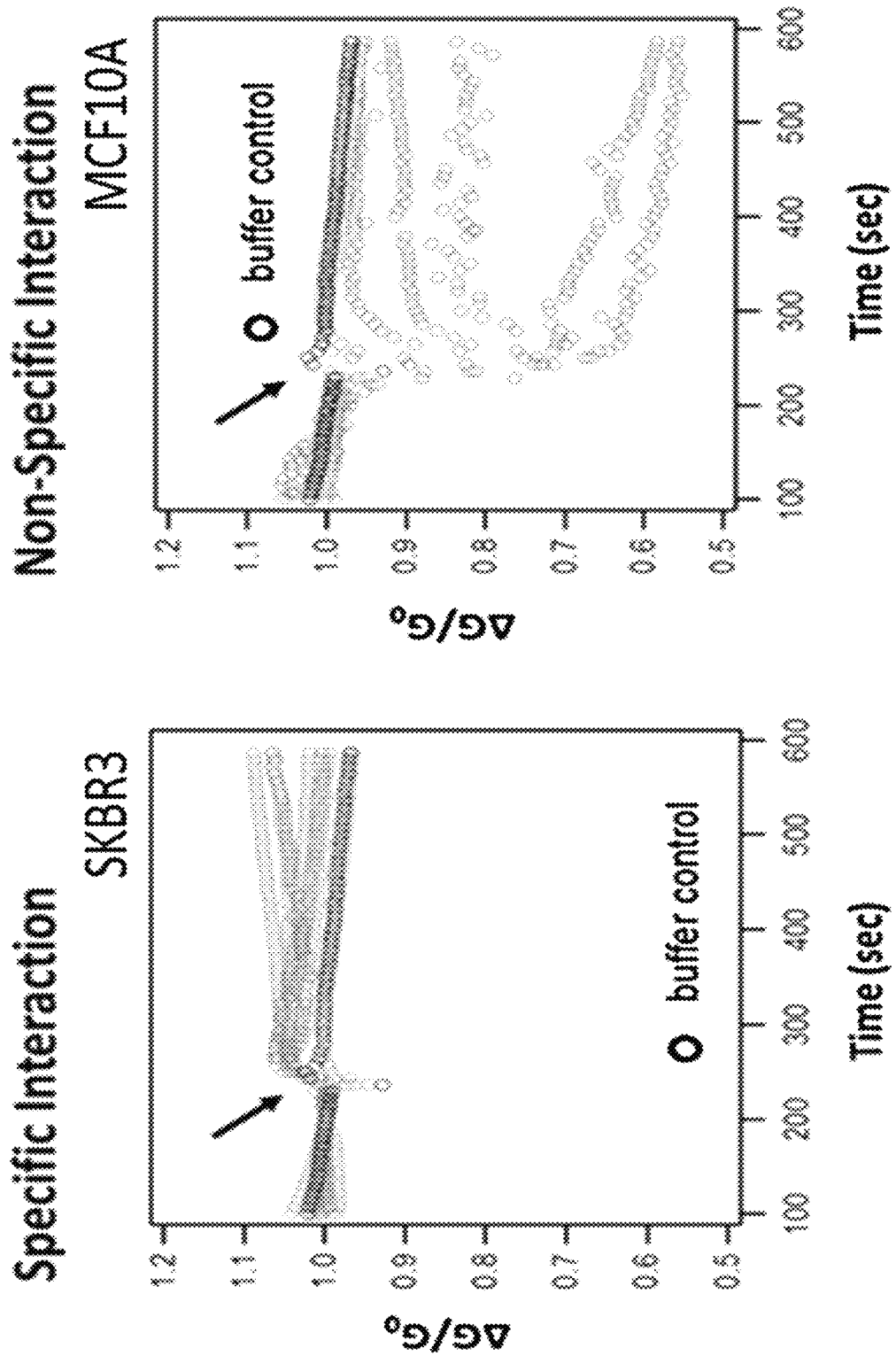
FIG. 4A-FIG. 4D present data showing interactions between antibodies and cells in a blood sample.
Figure 4D:
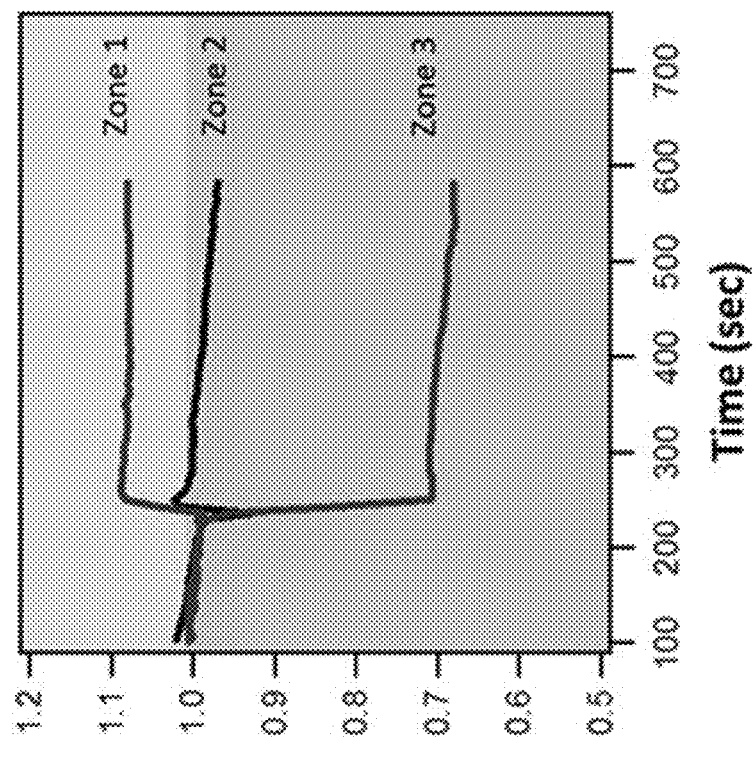
Figure 4C:
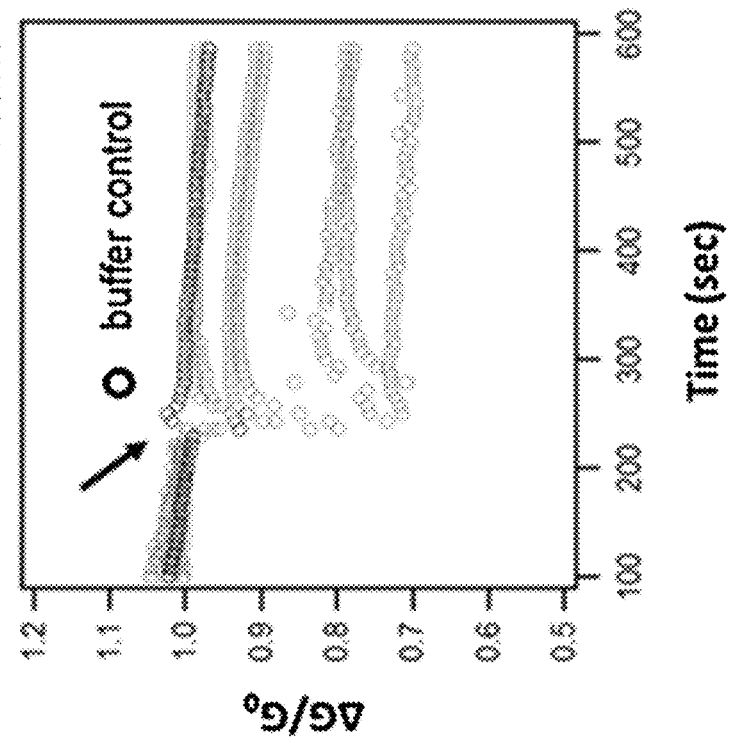

FIG. 4A and FIG. 4B present the electrical sensing from specific and non-specific interactions in blood. Three types of signals were identified. SKBR3 spiked blood that was adsorbed on anti-Her2 antibody device produced a characteristic device signature with increase in signal conductance (FIG. 4A). Similarly, MCF7 cells spiked in blood and adsorbed on anti-EpCAM nanotube surface produced a rise in signal conductance (shown in FIG. 5A and FIG. 5B). Similarly, MCF10A cells spiked in blood produced a characteristic device signature that was either no change or led to a decrease in electrical signal (FIG. 4B). Finally, plain blood adsorption on the anti-Her2 functionalized device produced a decrease in the device electrical signal or stayed at the buffer level suggesting no change (FIG. 4C). The specific and non-specific signals were visually classified into these three groups: 1) "Zone 1" or an increase in the device electrical signal; 2) "Zone 2" or no change and 3) "Zone 3",

TABLE 1

Design of Experiments

|  |  | Sample Type | | | |
| --- | --- | --- | --- | --- | --- |
|  |  | Plain Blood | SKBR-3 Spiked Blood | MCF-7 Spiked Blood | MCF-10A Spiked Blood |
| CNT Device Functionalization | IgG | 10 (negative control) | 20 (negative control) | 20 (negative control) | 20 (negative control) |
|  | HER-2 | 10 (negative control) | 20 (positive control) |  | 20 (negative control) |
|  | EpCAM | 10 (negative control) |  | 20 (positive control) | 20 (negative control) |

Table 1 presents the design of experiments and the number of replicates. Over all there were 10 replicates for each combination, 10 replicates for 100 cells and 10 replicates for 1000 cells for each type of cancer cell spiking. Three cell lines of SKBR-3, positive control (over expressing HER-2), MCF-7, positive control (overexpressing EpCAM), and MCF-10A, negative control normal epithelial cell line (not overexpressing HER-2 or EpCAM), were cultured and prepared for these experiments. In addition to these three spiked cell types, plain non-spiked blood was also tested as the fourth sample type, a negative control, with each device type.

CNT devices were divided into three groups; the first batch was functionalized with anti-HER-2 antibody, the second batch was functionalized with anti-EpCAM antibody, and the third batch was functionalized with non-specific IgG antibody via PASE linker molecule. Tween-20 nonionic detergent was adsorbed after functionalization to minimize non-specific adsorption to the non-functionalized CNT surface. In these experiments, there are 17 unique combinations within sample types, device functionalization, and cell concentration, with 170 technical array replicates, each holding 5 μl drops, resulting in 0.85 ml of blood processed in the array. Four combinations were designed as positive cases with specific interactions expected (SKBR-3 spiked blood vs. HER-2 functionalized CNT device and decrease in device electrical signal. FIG. 4D shows the zone classification scheme of the electrical signals.

Figure 5A:
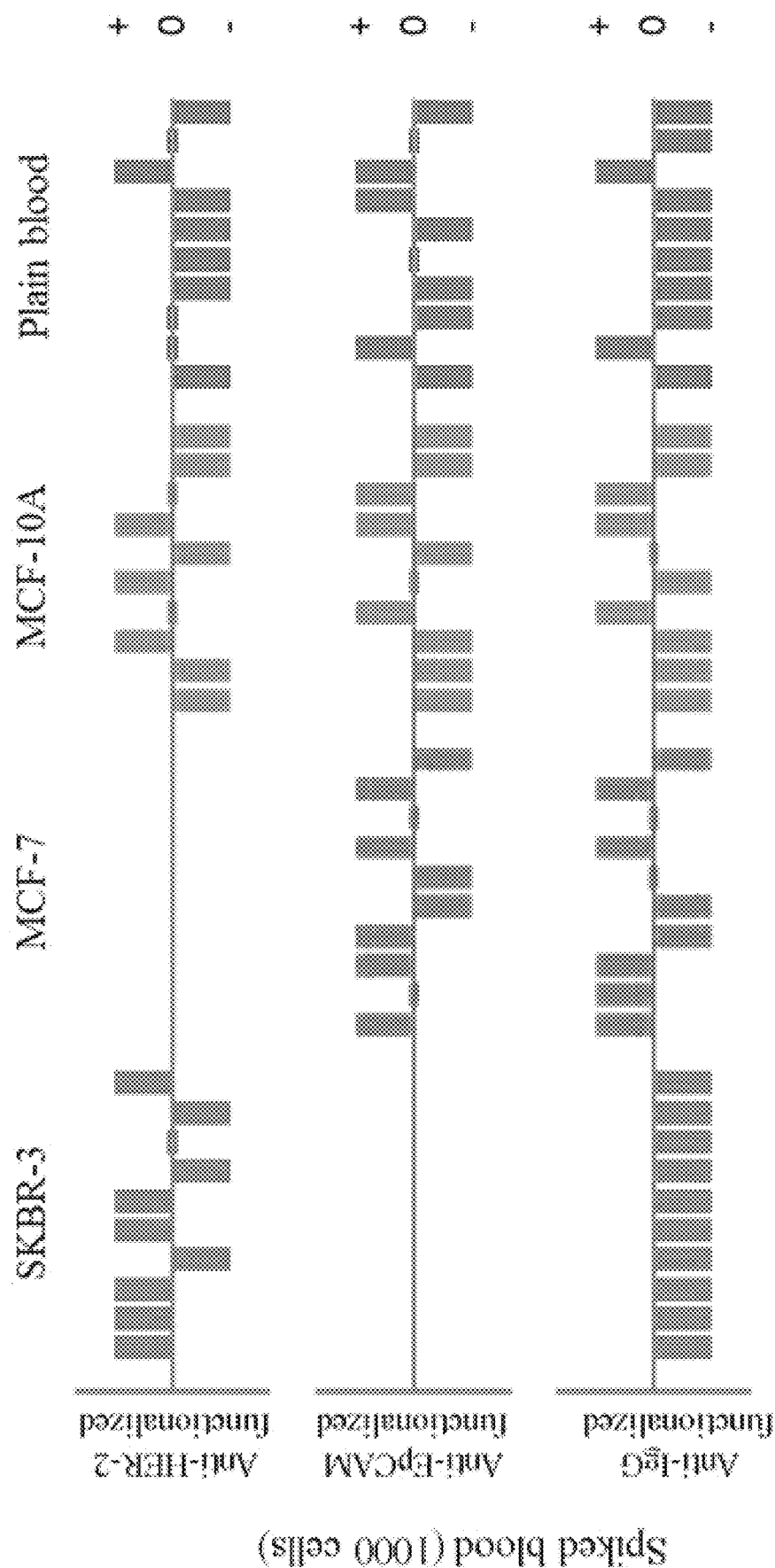
FIG. 5A and FIG. 5B present a merger of device array data for 1000 cells/5 μL and 100 cells/5 μl variation using the zone classification scheme.
Figure 5B:
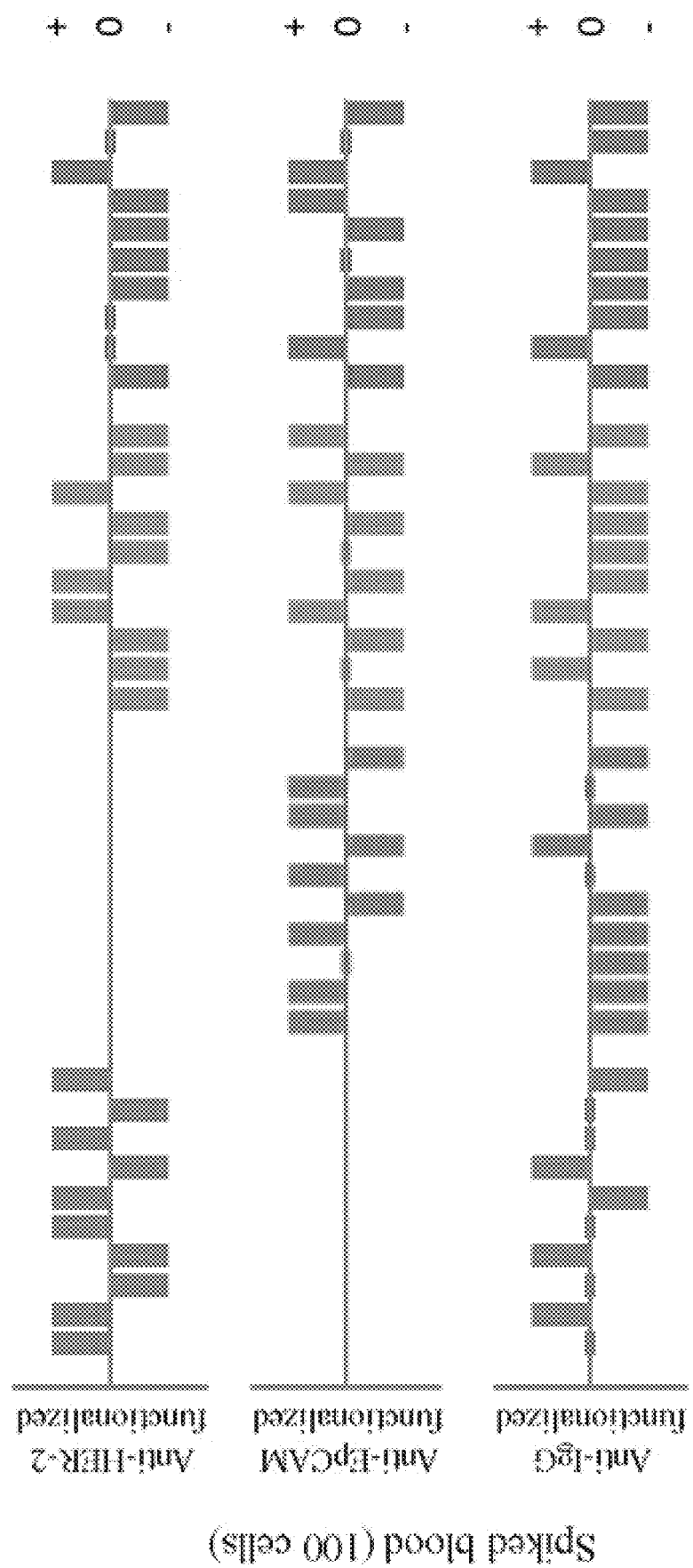

FIG. 5A and FIG. 5B present electrical signatures of 1000 cells/5 μL cell and 100 cells/5 μL cell concentration variation (all 170 elements classified by device type and sample type), collected during spiked blood experiments and classified according to the proposed scheme presented in FIG. 4C. The entire data with all 170 data sets, 17 combinations, 4 positive controls and 13 negative controls, were defined in these experiments as they are presented in FIG. 5A and FIG. 5B and can be represented in one map that can enable fast analysis by a technician. For example, the signal rise is indicated by blocks that are in the increasing direction. For no change the blocks are at the X-axis level and for decrease, the blocks go in the negative direction. The data visualized in this manner presents an easy way to analyze the sample condition and is suitable for the clinic.

The entire data can be divided into different experiments with both specific and non-specific interactions. FIG. 5A is a data series based on 1000 cells spiked in blood; FIG. 5B is a data series based on 100 cells spiked in blood. In both FIG. 5A and FIG. 5B, each panel correlates with one combination of sample type and device type with respect to design of experiment, 10 replicates each. Each row correlates to one type of device functionalization such as anti-HER-2, anti-EpCAM, and IgG. The top row represents the type of cells spiked namely SkBr3, MCF7, MCF10A. From left to right, the panels show: SKBR-3, MCF-7, MCF-1-A, and plain blood samples. The control buffer signal is shown as the x-axis. The symbol (+) represents signal increase, (0) represents no change and (−) represents signal decrease.

The actual data is presented in FIG. 10A-FIG. 10J and FIG. 11A-FIG. 11J for the 170 datasets.

Figures 10A, 10B, 10C:
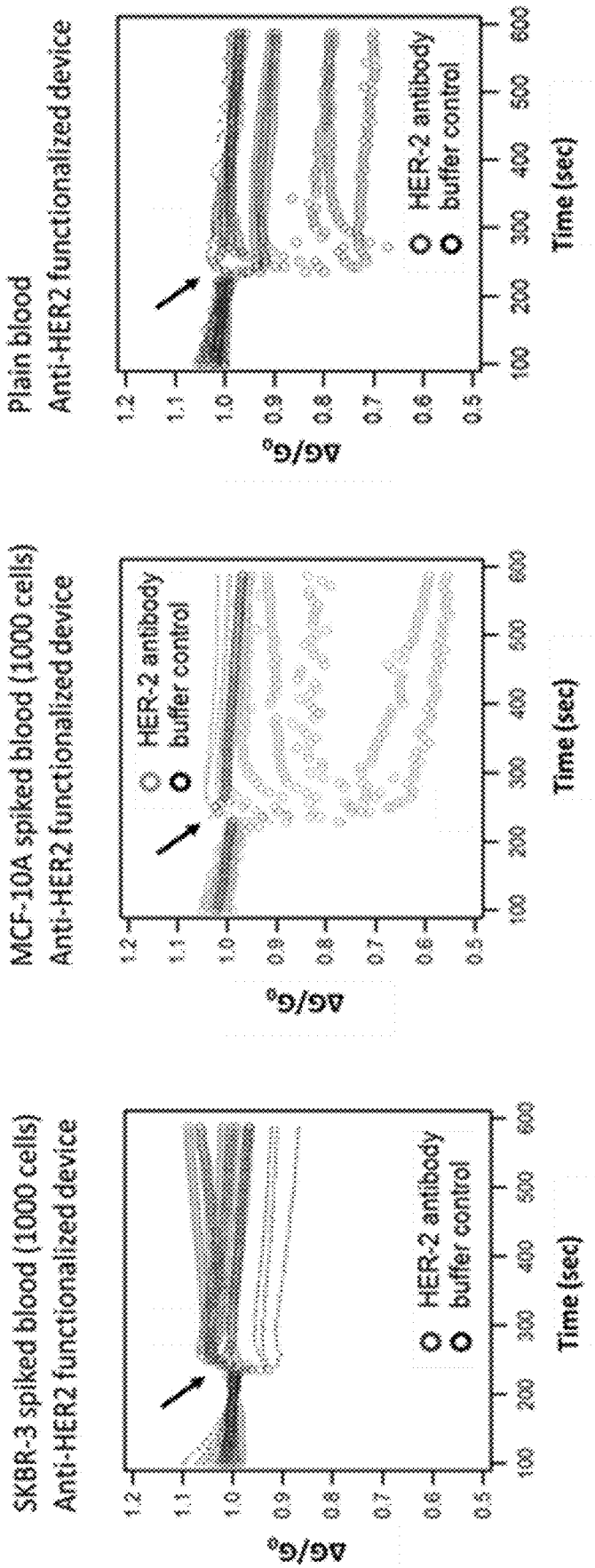
Figure 10F:
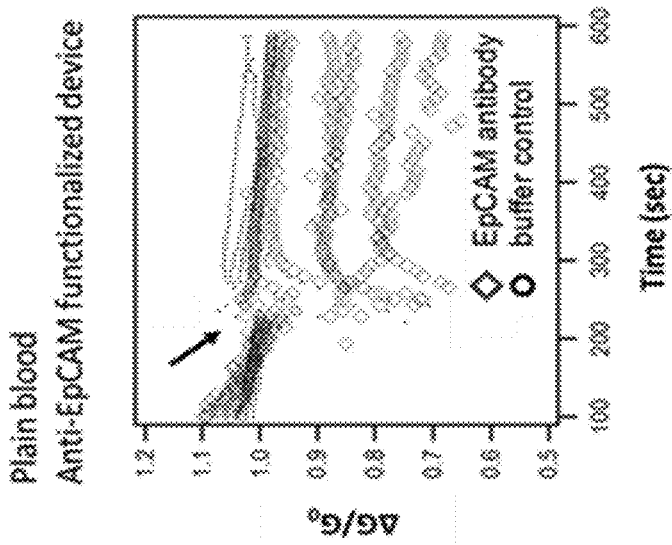
Figure 10E:
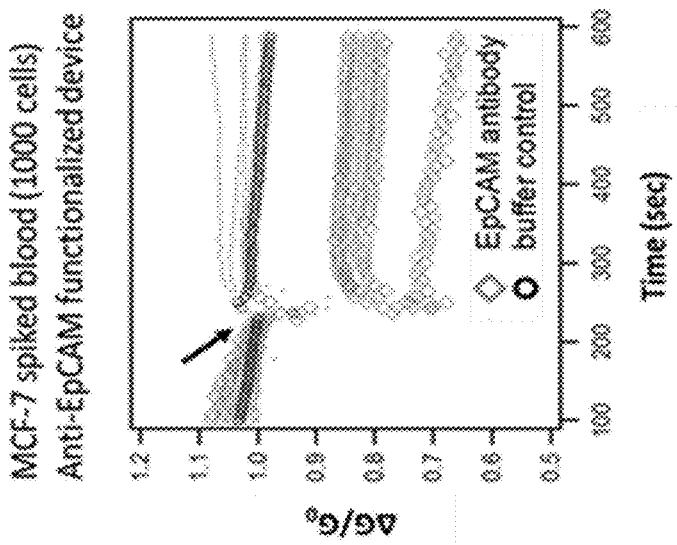
Figure 10D:
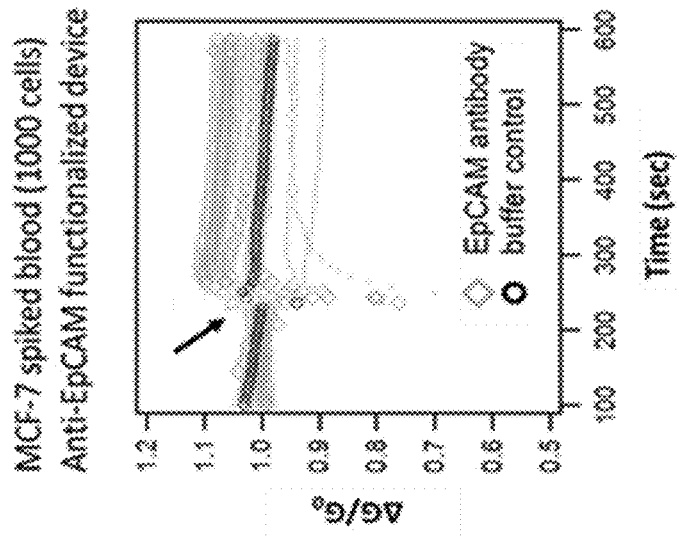
Figure 10H:
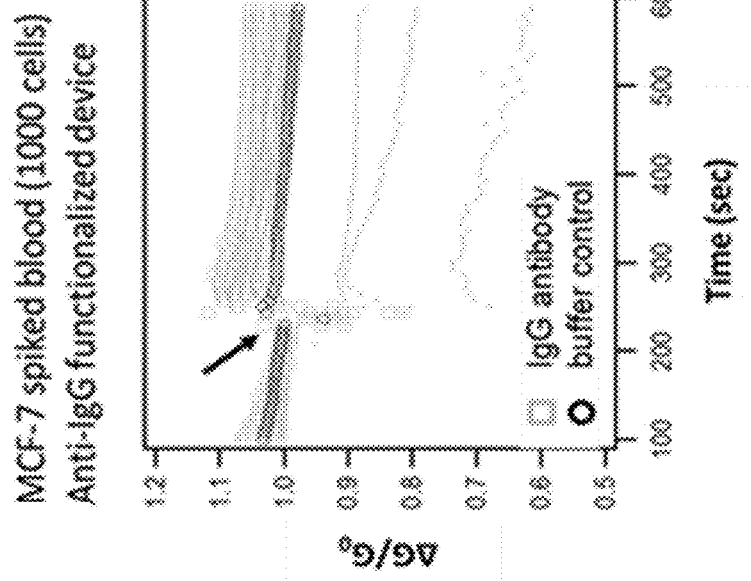
Figure 10G:
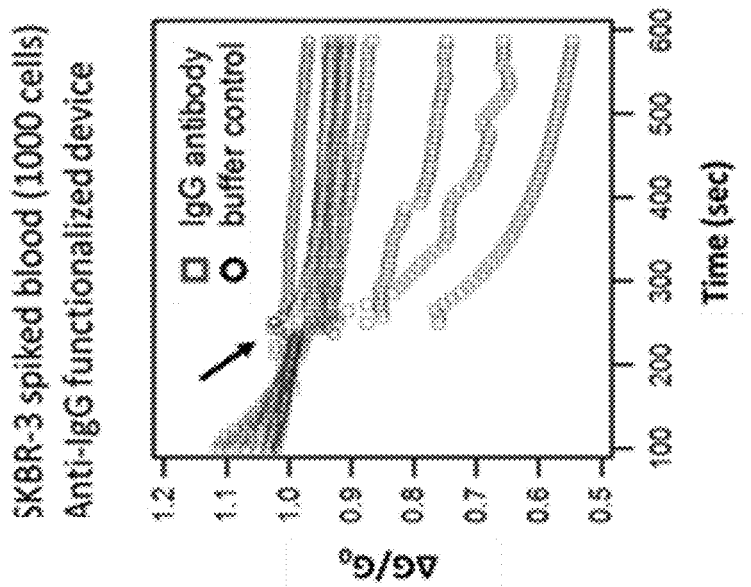
Figures 10I, 10J:
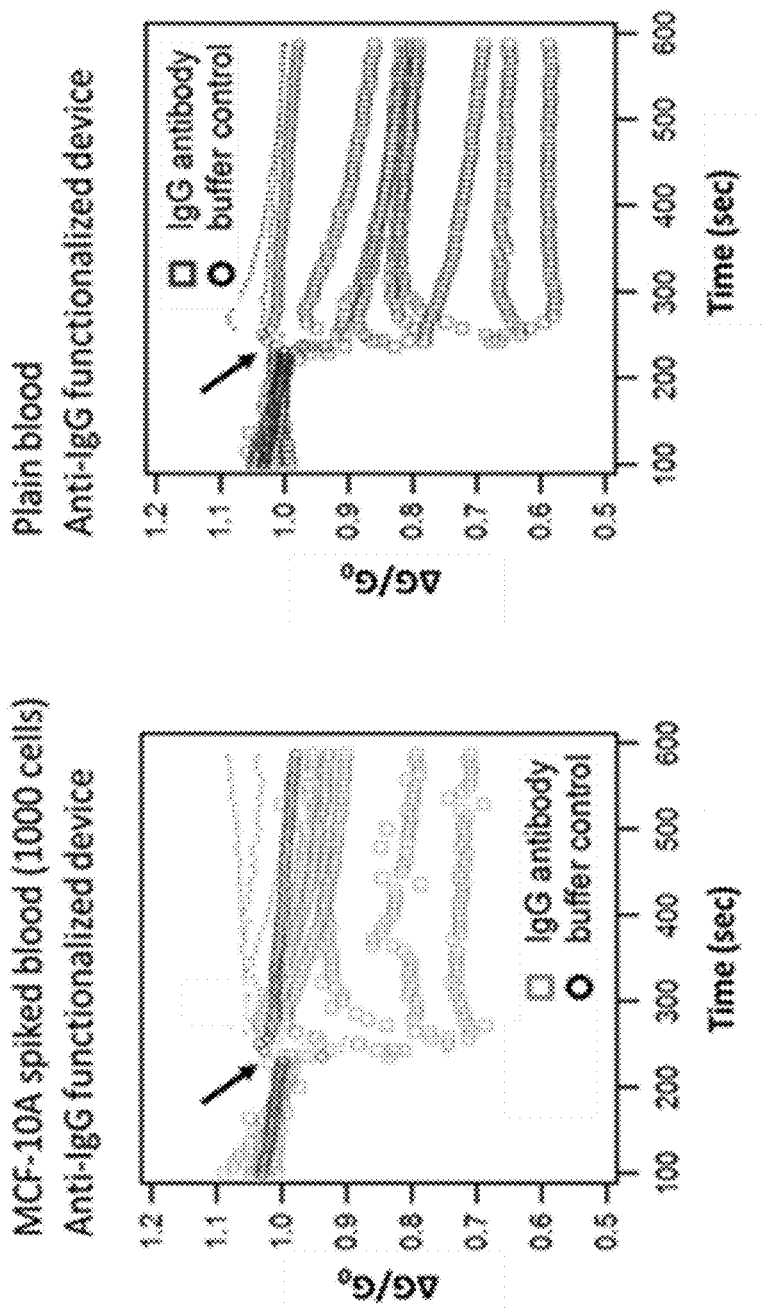

FIG. 10A-FIG. 10J present the device array data for 1000 cells/5 μL variation. Each figure correlates with one combination of sample type and device type with respect to design of experiment presented in Table 1, 10 replicates each. FIG. 10A, FIG. 10B, and FIG. 10C correlate to HER-2 device functionalization, FIG. 10D, FIG. 10E, and FIG. 10F correlate to EpCAM device functionalization, and FIG. 10G, FIG. 10H, FIG. 10I, and FIG. 10J correlate to IgG device functionalization. Plain blood samples are shown in FIG. 10C, FIG. 10F, and FIG. 10J. MCF-10A are shown in FIG. 10B. FIG. 10E and FIG. 10 I. MCF-7 are shown in FIG. 10D and FIG. 10H. SKBR-3 are shown in FIGS. 10A and 10G. The control buffer signal is shown in black circular marks in each panel as point of reference.

Figures 11A, 11B, 11C:
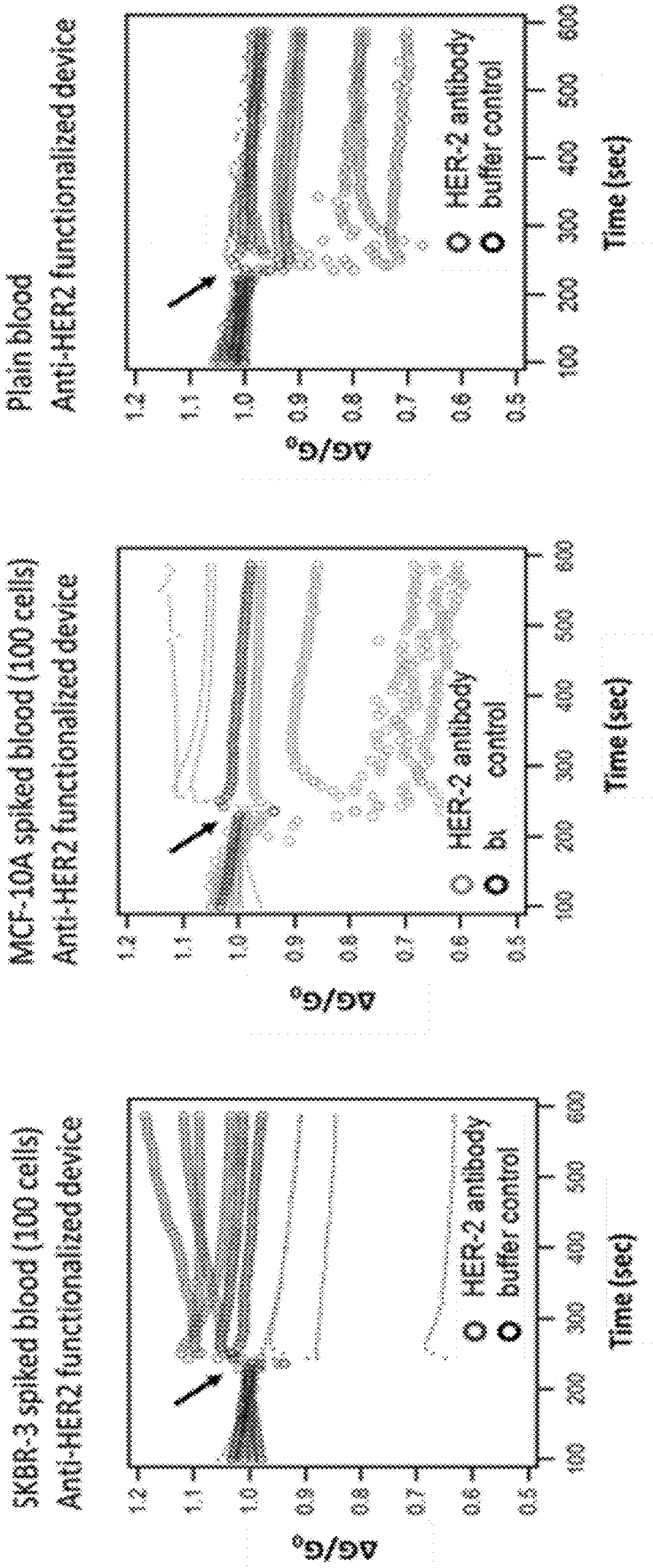
Figure 11F:
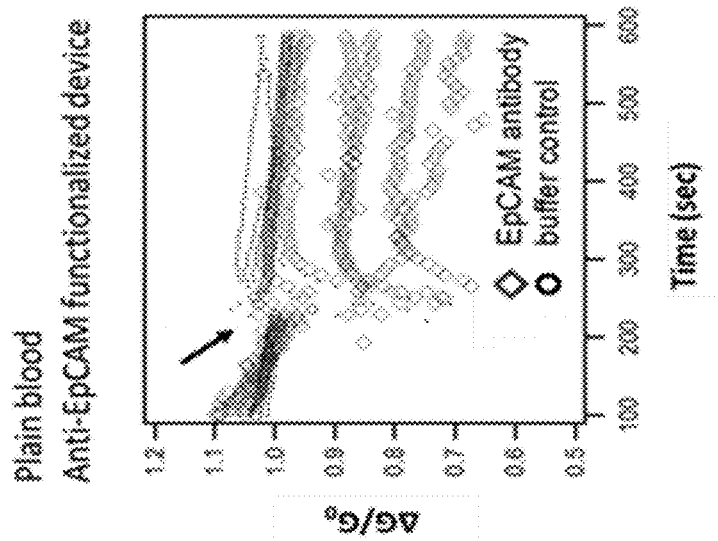
Figure 11E:
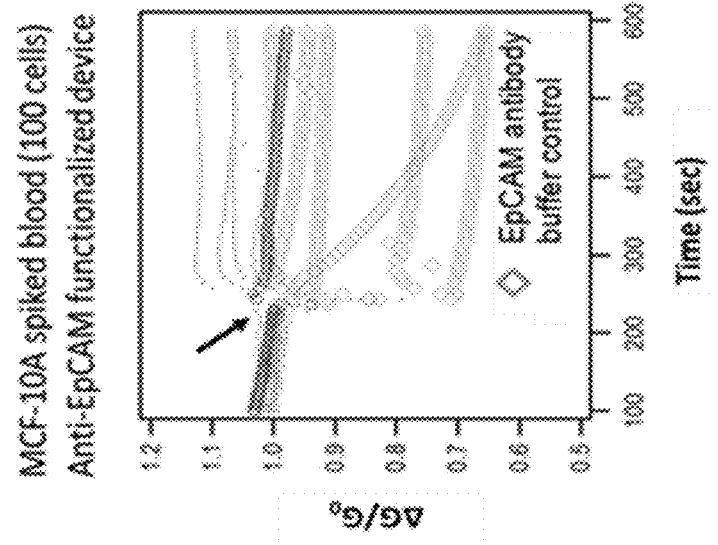
Figure 11D:
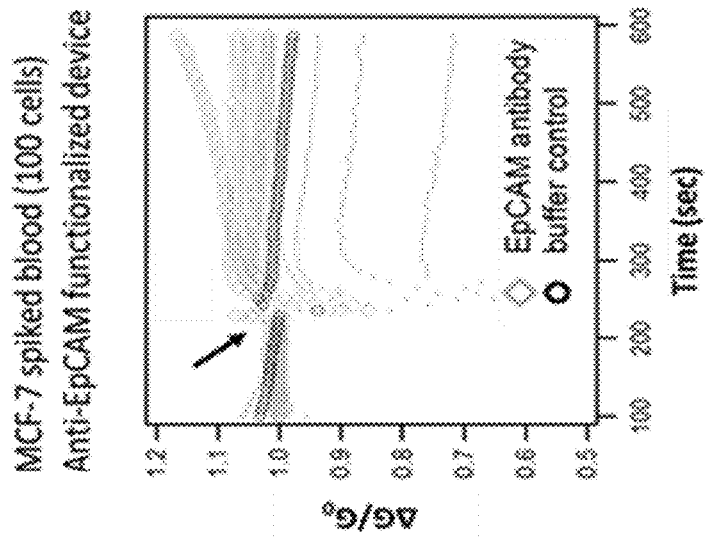
Figure 11H:
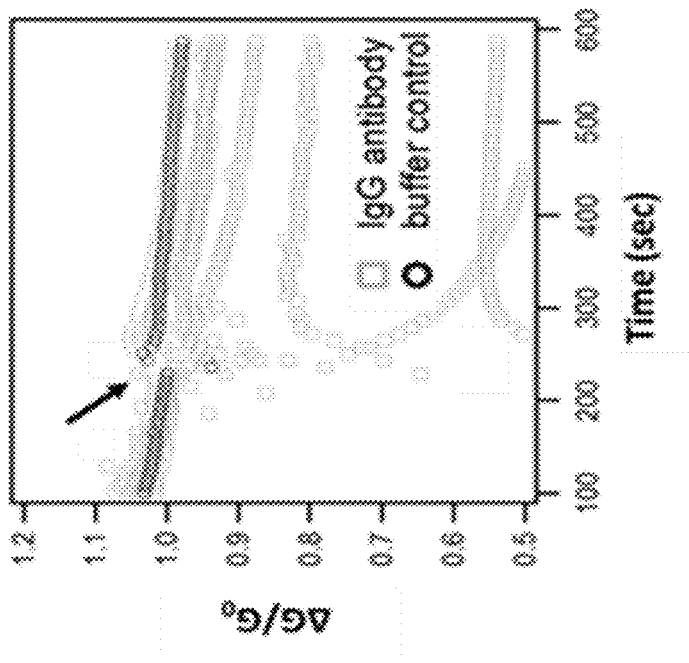
Figure 11G:
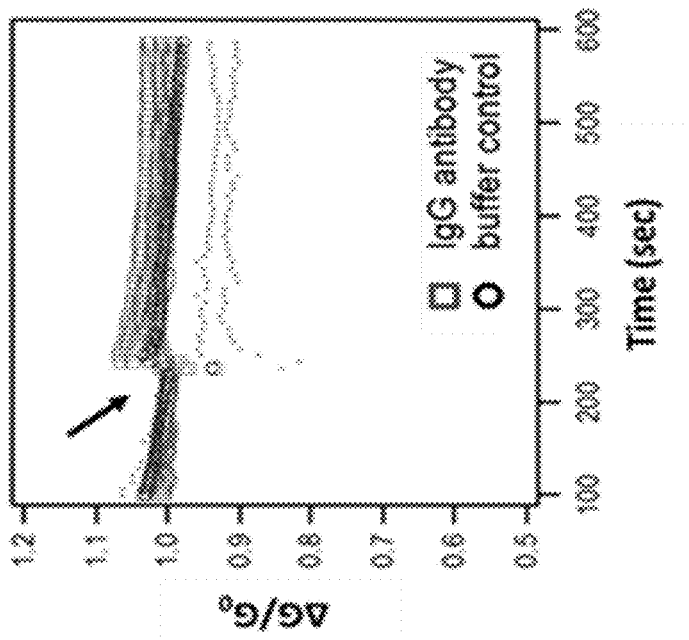
Figures 11I, 11J:
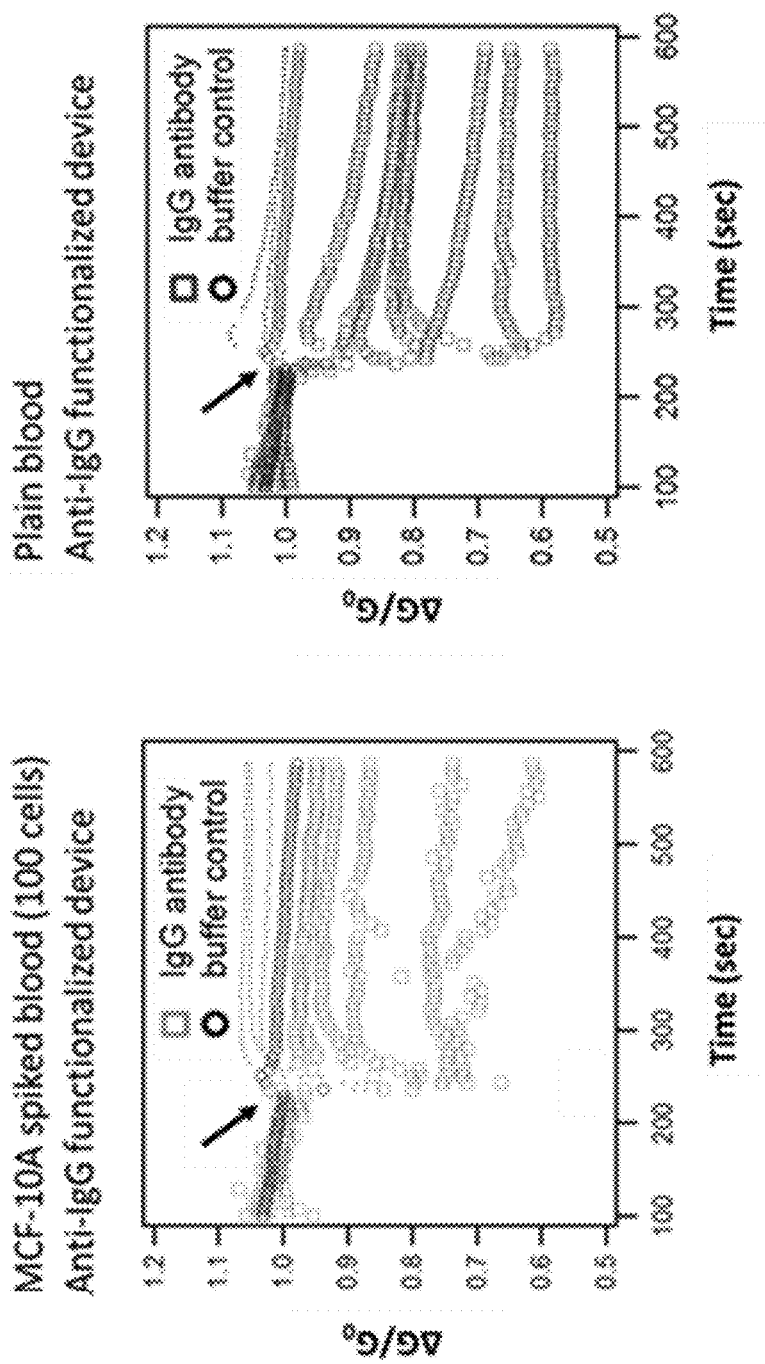

FIG. 11A-FIG. 11J present the device array data for 100 cells/5 μL variation. Each figure correlates with one combination of sample and device type with respect to design of experiment presented in Table 1, 10 replicates each. FIG. 11A, FIG. 11B, and FIG. 11C correlate to HER-2 device functionalization, FIG. 11D, FIG. 11E, and FIG. 11F correlate to EpCAM device functionalization, and FIG. 11G, FIG. 11H, FIG. 11, and FIG. 11J correlate to IgG device functionalization. Plain blood samples are shown in FIG. 11C, FIG. 11F, and FIG. 11J. MCF-10A are shown in FIG. 11B, FIG. 11E and FIG. 11 I. MCF-7 are shown in FIG. 11D and FIG. 11H. SKBR-3 are shown in FIGS. 11A and 11G. The control buffer signal is shown in black circular marks in each panel for point of reference.

Again, three types of signals were observed with respect to the buffer control: signal that increased, decreased, or did not significantly change with respect to the buffer control. The majority of signals in all 4 positive controls were located in "Zone 1" showing an increase in device conductance, with respect to the buffer control. On the other hand the majority of the signals, 11 out of the 13, in negative controls landed in "Zone 3", showing a decrease in their signal, device conductance, after addition of the sample droplet with respect to the buffer control.

Table 2 summarizes the zone classification results for all the data presented here. Overall, specific interaction indicated an increase in the device conductance whereas non-specific interaction resulted in a decrease or no change in device conductance. These results show spiked cancer cells can be discriminated in blood based on their effect on CNT electrical properties. In all the experiments the detection specificity for anti-Her2 devices were better than anti-EpCAM devices in these blood experiments.

Protein experiments were also conducted to ascertain the hypothesis using a streptavidin-biotin model system for signal rise. FIG. 12A and FIG. 12B present the normalized live response of six CNT devices, three functionalized with streptavidin (FIG. 12A) and three non-functionalized bare CNT devices (FIG. 12B). 5 μL of biotin solution, 1 ng/mL in 1×PBS, was added to each device at 60 seconds and the electrical current of the device was recorded for the remaining 240 seconds. The functionalized devices current increased after biotin introduction suggesting negatively charged biotin molecules interacting with streptavidin is equivalent to applying a negative gate voltage, thus increasing the nanotube-complex device conductance while, the bare devices show no significant change. Schematics in the right hand side of the figures illustrate the device functionalization state and its interaction with biotin molecule. This indicates that the primary effect of the nanotube-streptavidin-biotin binding is a charge-transfer reaction.

In general membrane potential of cancer cells are different from normal cells and recently they have been suggested as a valuable clinical biomarker for tumor detection. Electrophysiological analyses in many cancer cell types have revealed a depolarized Vm that favors cell proliferation and new data suggest level of Vm has functional roles in cancer cell migration. Vm changes because of alterations in the conductance of one or more types of ions. The Goldman-Hodgkin-Katz equation shows the Vm dependency on both the intracellular and extracellular concentrations of major ions (Na+/K+). Thus interaction of specific antibodies to the extracellular receptors affects Vm. MCF7, MCF10A and SKBR3 cells have all negative resting potential. For example, the MCF7 potential was reported to vary from −58.6 mV to −2.7 mV with the cell cycle. Extracellular EpCAM receptors on MCF7 cells interacting with anti-EpCAM antibodies on nanotube surface can thus lead to an increase in conductance of the nanotube-complex similar to

TABLE 2

Electrical Signal Classification Results

| Experiment # | Cell Concentration | Device Type | Sample Type | Zone 1 | Zone 2 | Zone 3 | Total |
|---|---|---|---|---|---|---|---|
| 1 | 1000 | HER-2 | SKBR-3 | 6 | 1 | 3 | 10 |
| 2 | 1000 | HER-2 | MCF-10A | 3 | 2 | 5 | 10 |
| 3 | — | HER-2 | Plain | 1 | 3 | 6 | 10 |
| 4 | 1000 | EpCAM | MCF-7 | 5 | 2 | 3 | 10 |
| 5 | 1000 | EpCAM | MCF-10A | 3 | 1 | 6 | 10 |
| 6 | 1000 | EpCAM | Plain | 3 | 2 | 5 | 10 |
| 7 | 1000 | IgG | SKBR-3 | 0 | 0 | 10 | 10 |
| 8 | 1000 | IgG | MCF-7 | 5 | 2 | 3 | 10 |
| 9 | 1000 | IgG | MCF-10A | 3 | 1 | 6 | 10 |
| 10 | — | IgG | Plain | 2 | 0 | 8 | 10 |
| 11 | 100 | HER-2 | SKBR-3 | 6 | 0 | 4 | 10 |
| 12 | 100 | HER-2 | MCF-10A | 3 | 0 | 7 | 10 |
| 13 | 100 | EpCAM | MCF-7 | 6 | 1 | 3 | 10 |
| 14 | 100 | EpCAM | MCF-10A | 3 | 2 | 5 | 10 |
| 15 | 100 | IgG | SKBR-3 | 3 | 5 | 2 | 10 |
| 16 | 100 | IgG | MCF-7 | 1 | 2 | 7 | 10 |
| 17 | 100 | IgG | MCF-10A | 3 | 0 | 7 | 10 | negatively charged proteins. These specific interactions are characteristically different compared to non-specific interactions.

Table 2 summarizes the zone classification quantitatively. All the specific interactions had maximum of 6/10 signals in "Zone 1", whereas non-specific interactions had 9/10 signals in combination of "Zone 2" and "Zone 3". This suggest that this classification scheme may be highly useful in clinic, where one can define a threshold of at least 5/10 devices in "Zone 1" as a "diagnostic gray zone" which may indicate the presence of cancer cells in blood on the device. While Table 2 presents the quantifiable data, the blocks can also be added in each zone in FIG. 5A and FIG. 5B to come to the same conclusion. One can then further analyze the devices for cell capture using optical and confocal microscopy if the threshold exceeds 5/10 devices. It should be noted that some devices for specific interactions do not increase in signal.

Dynamic Time Warping Classification

Dynamic Time Warping (DTW) is a dynamic programming algorithm that seeks to find an optimal global or local alignment of two series in the time domain to minimize the total distance between the series with respect to a traditional distance metric such as Euclidean distance metric. The DTW-distance can then be used as dissimilarity metric for developing kernel-based classifiers. A k-nearest neighbours kernel-based statistical classifier was developed using pairwise DTW-distances between samples. A kernel-based learning method was chosen as a parametric model for CTC evaluation. In order to test whether the HER-2 functionalized devices could discriminate between SKBR3 spiked blood samples and controls (plain blood and MCF10A spiked blood), a classifier was constructed and the area under the receiver operator curve (AUC) was estimated by 10-fold cross-validation. Algorithm parameters and series normalization method were also determined by cross-validation. The series normalization methods evaluated were: mean-variance normalization of the entire series, slope correction followed by normalization, and slope correction followed by scaling by the value at a fixed time-point. Mean-variance normalization was defined as $y_i = y_i - \bar{y}_i / s_{y_i}$ where $\bar{y}_i$ represents the mean of the ith replicate series and $s_{y_i}$ represents the standard deviation. Slope correction was conducted by fitting a linear model to the first 75 series sampling points to estimate the machine drift of the devices. In addition to evaluating slope correction followed by mean-variance normalization, slope correction followed by scaling the series by dividing by series value at a standardized time-point (50) was evaluated. Prior to normalization or scaling, the series were truncated to have length 150, with the length symmetric about the time-point of droplet deposition. Both high (1,000/5 µL) and low (100/5 µL) concentrations of spiked cells were evaluated, separately. A total of 30 replicates (10 replicates with 1,000 SKBR3 cells/5 µL spiked, 10 replicates with no cells added, and 10 replicates with 1,000 MCF-10A cells/5 µL spiked) were used in the construction of the classifier. To ensure balance between the SKBR-3 positive condition and negative condition, a random sample of 5 replicates with no spiked cells and 5 replicates with 1,000 MCF-10A cells/5 µL spiked was combined as SKBR3 negative. Whether the series observed with anti-HER2 antibody functionalized devices and SKBR3 spiked blood could be discriminated from IgG functionalized devices was then evaluated to determine if the anti-HER-2 antibody and SKBR3 spiked blood resulted in a specific as opposed to non-specific antibody-antigen interaction.

Cross validation (CV)-estimated AUC for the DTW distance based k-nn classifiers for the high concentration of SKBR3 cells with anti-HER-2 functionalized devices are shown in FIG. 13A. The highest AUC for this condition was observed for the 1-nearest neighbor classifier with slope corrected normalized series.

TABLE 3

Dynamic Time Warping: CV-Estimated Confusion Matrix for 1000 SKBR-3 Cells in Blood

| | Predicted Class | |
|---|---|---|
| True Class | Negatives (Not Spiked/ MCF-10A) | Positives (SkBr3 Spiked) |
| Negatives (Not Spiked/ MCF-10A) | 9 | 1 |
| Positive (SkBr3 Spiked) | 1 | 9 |

Class prediction using CV-estimation confusion matrix for high concentration SKBR-3 cells is presented in Table 3. AUC for discriminating a low concentration condition is shown in FIG. 13B. AUC for the discrimination tests between antibodies (anti-HER2 versus IgG) with SKBR3 cells spiked in blood is shown in FIG. 13C.

Devices functionalized with anti-HER2 antibody were able to discriminate between blood spiked with a high concentration of SKBR-3 cells (1,000/5 µL) and control blood (spiked with MCF-10A cells, or not spiked, plain blood). 10-fold cross-validation estimated AUC for the 1-nearest neighbor DTW-distance based classifier was 0.90 after slope correction and normalization. Table 3 presents the confusion matrix. One false negative and one false positive out of 10 positives and 10 negatives were observed in the cross-validation procedure, showing a cross-validation estimated sensitivity of ~90% and specificity of ~90%. Of the replicates identified as true positives, 6/9 series finished higher, "Zone 1", after the rebound that followed droplet injection than the initial period, indicating a favorable ΔG; of the replicates identified as true negatives, 7/9 series finished lower, "zone 3" after the rebound that followed droplet injection than the initial period.

Devices functionalized with HER2 antibody were unable to significantly discriminate (>50%) between blood spiked with a low concentration of SKBR-3 cells (100 cells/5 µL) and control blood using a kernel-based classifier. The signals can be analytically differentiated as presented in Table 2.

Good discrimination was achieved based on DTW from the cancer cell concentration of 1000/5 µL or 200,000/mL, which is at the high concentration end of the real patient range of 50-300,000/mL.

Fixing sample phenotype (blood spiked with 1000 SKBR3 cells) allowed for discrimination of antibody functionalization, anti-HER-2 vs. IgG functionalized device. 10-fold cross-validation estimated AUC for the 1-nearest neighbor DTW-distance based classifier was 0.70 after slope correction and normalization (FIG. 13C). Based on the results from fixing the sample phenotype and separately device phenotype, the significant difference seen in electrical signal with positive controls is a result of HER2 receptor, on the cell membrane, interaction with the anti-HER2 antibody on the surface of the nanotube device.

FIG. 6A presents the heatmap of the between signal DTW distances for the signals used in the classifier employed for discriminating the high concentration of SKBR3 cells. In the margins of this figure a dendrogram of the complete-linkage agglomerative hierarchical clustering of the same is shown.

Within the clusters determined by the complete-linkage agglomerative hierarchical clustering there is evidence of sample type confusion however this confusion was reduced when considering 1-nearest neighbor kernels for classification. The kernel-based DTW classifier partitioned the SKBR3 spiked blood and controls (MCF7 spiked blood and non-spiked blood) suggesting specific interactions are quite unique in their electrical signatures compared to non-specific interactions and establishes a relationship between electrical conductance data with biological and possibly proteomic features (presence or absence of cancer cells in blood versus presence or absence of Her2). FIG. 6B presents the Her2 clustering data. The classifier is thus able to naturally partition the SKBR3 cells in blood data overexpressing Her2. This type of clustering is useful for the clinic to stratify devices based on Her2/other receptor data.

Optical Microscopy and Enumeration of CTCs

In a static blood sample/droplet the cells inside the blood start to settle immediately due to the forces of gravity, resulting in cells coming in contact and interacting with the base substrate surface. One can tune the surface interactions for efficient capture of CTCs. The initial observations on the optical microscope of cancer cell spiked blood sample droplets on top of the devices showed that the spiked cancer cells as part of their settling process get buried under RBCs and on top of the CNT network established on silicon substrate, getting sandwiched in between.

Figure 7A:
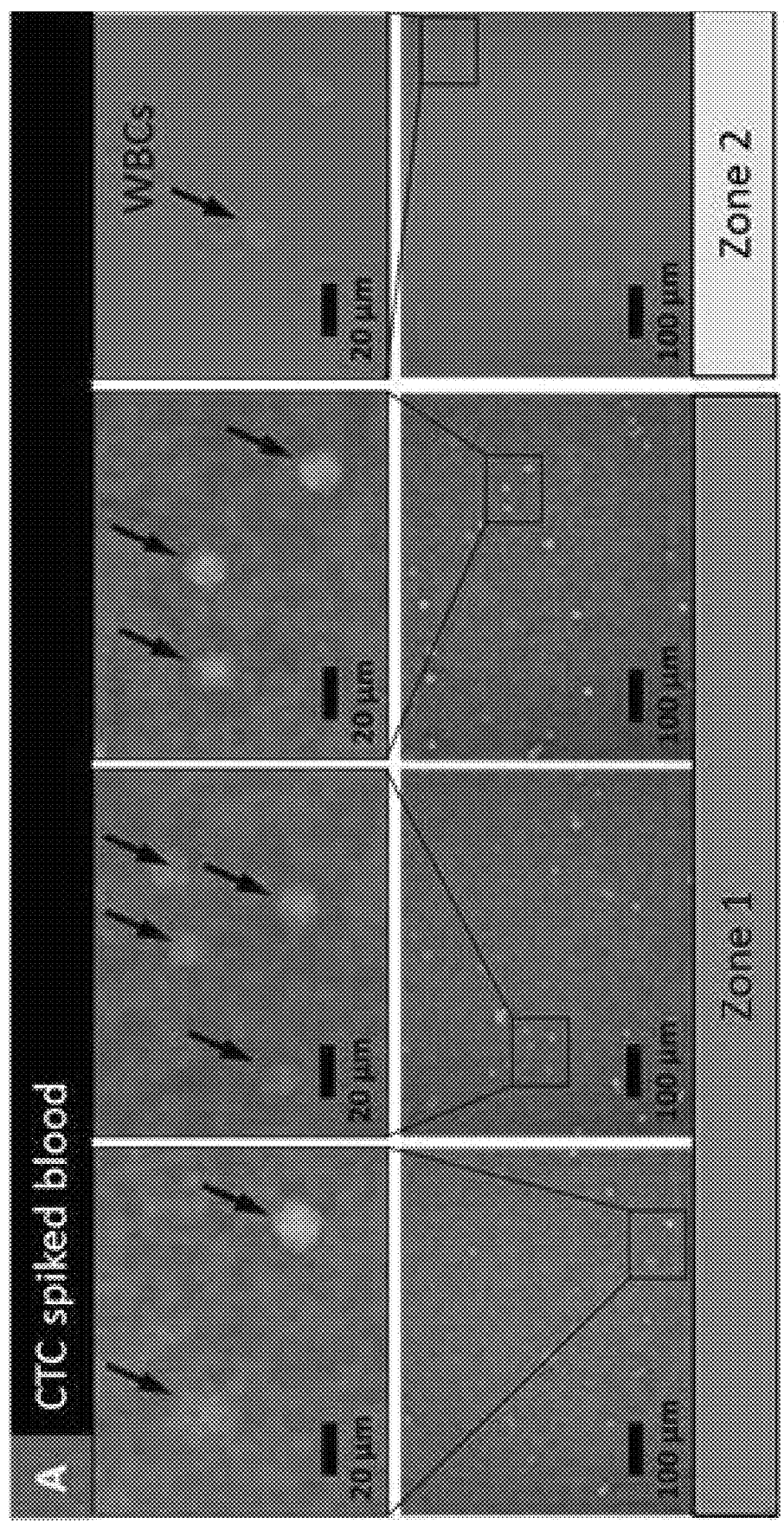
Figure 7C:
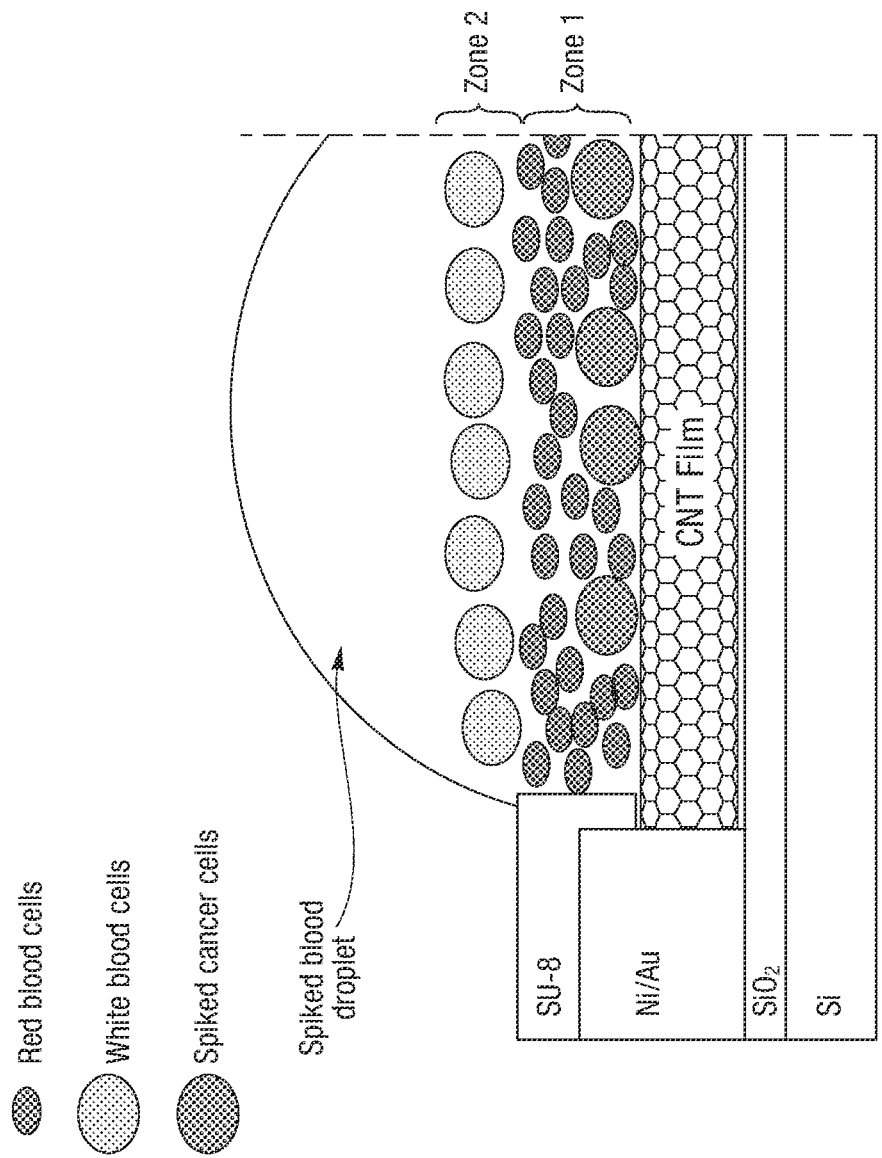

FIG. 7A shows optical microscopic images of spiked blood sample droplets on top of the device. Three devices of spiked cancer cell blood samples are shown. Spiked cancer cells are observed in the blood and marked with an arrow, one can clearly observe the cancer cells buried under the RBCs and on top of the CNT film. High concentration of RBCs is apparent on top of the marked cancer cells in "Zone 1". When the objective is focuses on "Zone 2" WBC's are seen in the spiked samples. FIG. 7B shows a plain blood sample. There are no cancer cells or WBCs observed in plain blood samples when the microscope is focuses in "Zone 1" plane. On the other hand when image is focused in the plane of "Zone 2" WBCs are apparent in the image (right panel), floating above the RBCs. FIG. 7C presents a schematic illustration of the mechanism of differential settling of blood sample on device observations under the microscope, showing the approximate arrangement of RBCs, WBCs, and spiked cancer cells and the classification of "Zone 1" and "Zone 2" accordingly.

Three examples of spiked cancer cell blood samples are presented in FIG. 7A at two different magnifications. Spiked cancer cells are observed in the blood and marked with an arrow, with the cancer cells buried under the RBCs and on top of the substrate. Cells that were imaged in "Zone 2" in the spiked blood samples are also shown. The size, shape and the number of cells seen in "Zone 2" is consistent with WBCs. A high concentration of RBCs is apparent on top of the marked cancer cells in "Zone 1". In FIG. 7B, optical microscopy of plain blood sample is presented at the same two magnifications. There are no spiked cancer cells seen as the microscope is focused in "Zone 1" plane. On the other hand, when the objective is focused on the "Zone 2" plane, WBCs are apparent and come into focus in the image (right panel), floating above the RBCs. A model of differential settling is presented in FIG. 7C in direct identification of spiked cancer cells and distinguishing from leukocytes using nanotube devices in an optical microscopy setting. The results of the settling of cancer cells to the bottom is also consistent with the rise in electrical signal which could come from the interaction of the cell surface receptors with the antibodies on the nanotube surface. Further, enhancement of enrichment can also be enabled through the presence of an electric field to separate the larger cancer cells displacing a volume in blood thereby changing the electric field.

As a result of the observations with regards to blood cell settling as illustrated in FIG. 7C, "Zone 1" was imaged and the captured spiked cancer cells further analyzed using optical microscopy. A number of devices with 1000 spiked cells and 100 spiked cell samples were selected and their respective optical microscope images were taken. 20 devices imaged at 20× magnification, and 15 devices, imaged at 5× magnification, were selected for further processing and analysis.

Spiked Breast Cancer Cell Enumeration in Blood

Figures 14A, 14B, 14C:
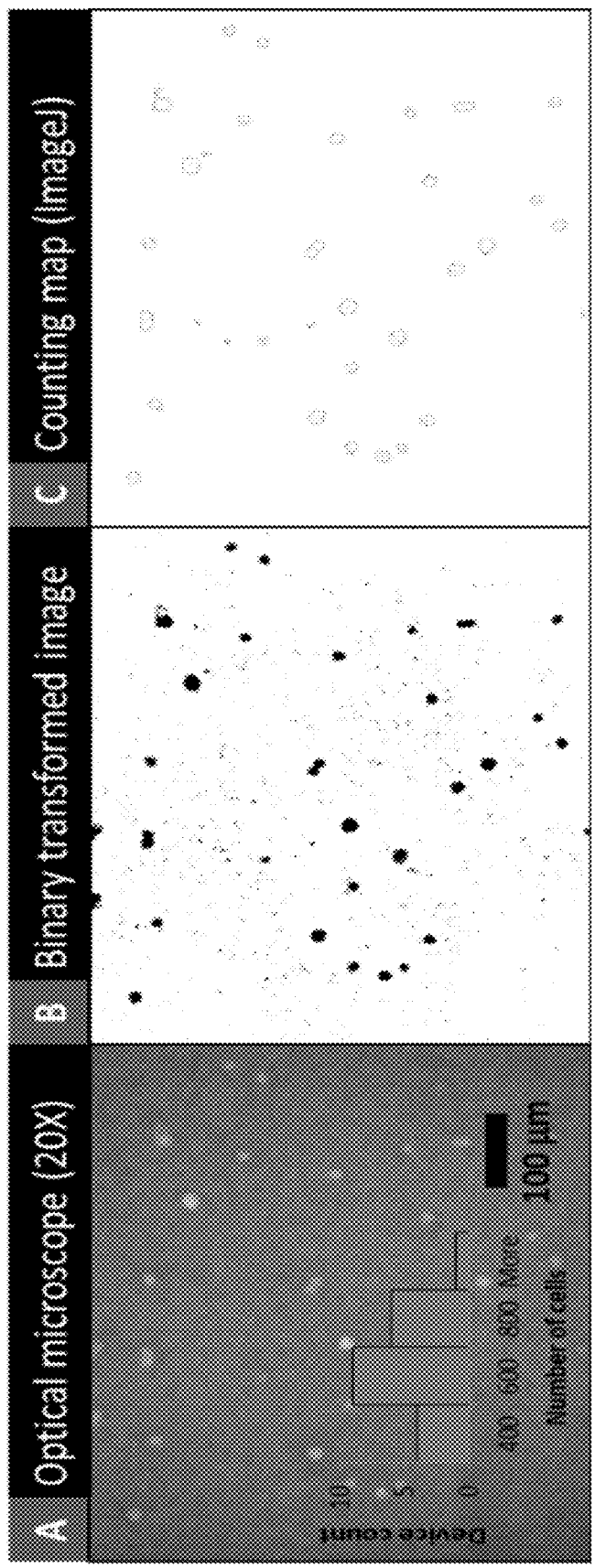
Figures 14D, 14E, 14F:
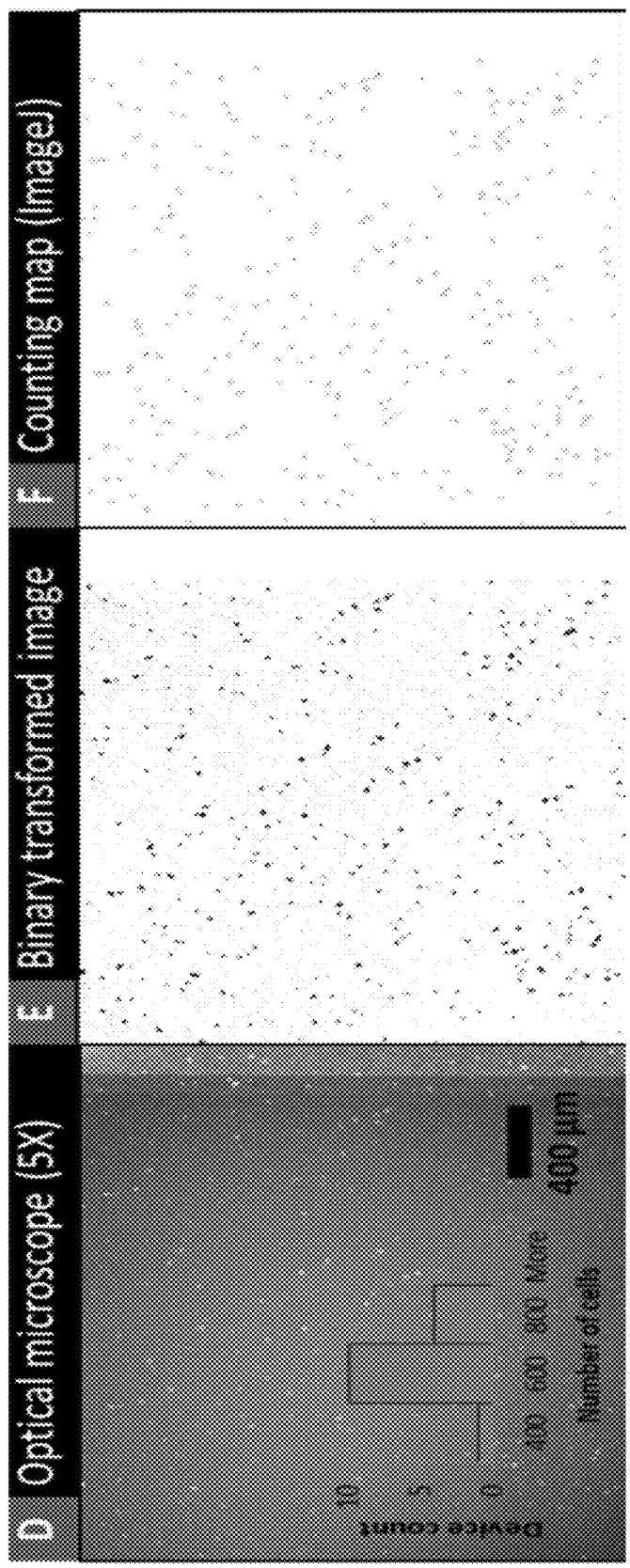
Figure 14G:
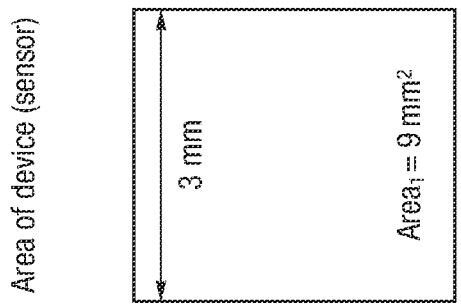
Figure 14H:
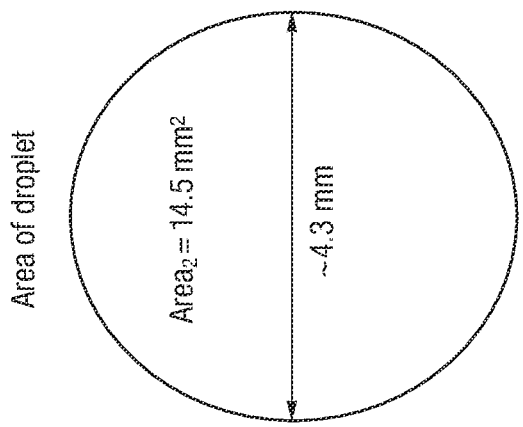
Figure 14I:
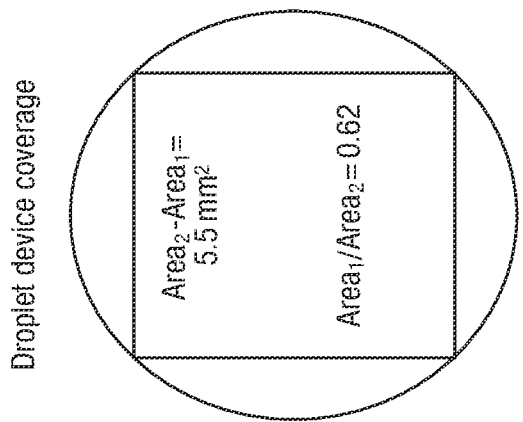

FIG. 14A-FIG. 14I present cell capture and enumeration. FIG. 14A and FIG. 14D present optical microscope image of devices with 1000 SKBR3 cells spiked blood sample droplet top at 20× and 5× magnification. The insert is the histogram of the number of devices versus number of cells counted in the active area (CNT) of the device. FIG. 14B and FIG. 14E show binary conversion of the optical microscope images, highlighting the spiked cells in black and separating them from the background. FIG. 14C and FIG. 14F present the ImageJ analyses of binary images, based on diameter and shape, showing cell count map of each original optical image. FIG. 14G and FIG. 14I demonstrate surface area comparison of the square shaped device vs. circular blood droplet covering the device. CNT device is only covered by ~62% of the total droplet area which gave rise to the electrical signal and optical microscopy was only done on this active area for these demonstrations.

FIG. 14A and FIG. 14D present an example set of 20× and 5× optical images taken for image analysis. ImageJ software was used to process each image. The histograms in each image present the number of cells counted in each device. Original optical images were converted to binary images and processed using NIH ImageJ software to distinguish spiked cells, shown in black circles, from the RBCs in the background by using the color threshold function as presented in FIG. 14B and FIG. 14E. Next, ImageJ software's particle analysis function was used to count the number of cells and cell diameter for each set of images knowing the scale bar for each image (FIG. 14C and FIG. 14F).

TABLE 4

Cell Count Data per Device Based on 20 × Images for 1000 Cell Count Spiked in Blood

| Device Number | Number of Cells | Cells/mm$^2$ | Average diameter (μm) | Number of Cells per Device |
|---|---|---|---|---|
| 1 | 33 | 78 | 10 | 706 |
| 2 | 31 | 74 | 11 | 663 |
| 3 | 24 | 57 | 10 | 514 |
| 4 | 24 | 57 | 15 | 514 |
| 5 | 15 | 36 | 14 | 321 |
| 6 | 33 | 78 | 14 | 706 |
| 7 | 32 | 76 | 11 | 685 |
| 8 | 22 | 52 | 13 | 471 |
| 9 | 16 | 38 | 13 | 342 |
| 10 | 32 | 76 | 13 | 685 |
| 11 | 36 | 86 | 12 | 771 |
| 12 | 24 | 57 | 14 | 514 |
| 13 | 39 | 93 | 15 | 835 |
| 14 | 30 | 71 | 16 | 642 |
| 15 | 30 | 71 | 14 | 642 |
| 16 | 25 | 59 | 15 | 535 |
| 17 | 35 | 83 | 15 | 749 |
| 18 | 49 | 117 | 14 | 1049 |

TABLE 4-continued

Cell Count Data per Device Based on 20 × Images for 1000 Cell Count Spiked in Blood

| Device Number | Number of Cells | Cells/mm² | Average diameter (μm) | Number of Cells per Device |
|---|---|---|---|---|
| 19 | 37 | 88 | 14 | 792 |
| 20 | 16 | 38 | 14 | 342 |
| Average | 29 | 69 | 13 | 624 |
| Std. Dev. | 8 | 20 | 2 | 178 |

All the data from these analyses, including number of cells per image, cells per unit of area (mm2), diameter of cells, and number of cells per device calculated based on cell counts and total device area, 9 mm2, are presented in the histograms in FIG. 14A-FIG. 14I and in Table 4.

The imaging was done on only ~62% active area of the device or the nanotube surface. In these experiments, blood did spread outside the active area of the device in some of the samples and CTCs in those areas were not counted, nor did they contribute to the electrical signal. These devices were initially designed for sensing experiments. An SU8 layer was used to isolate all the electrical layers except the active nanotube layer using an extra photo-lithography step. Even with only ~62% active area of device imaged and counted, this resulted in anywhere between 342-1049 cells captured, using optical microscopy on the active area of the nanotube device, resulting in a capture yield (normalized to 62%) of 55% to 100%. Even without normalization, the capture yield still represents 34.2% to 100%. The slightly greater than 1000 cells counted is a result of small variations in cells counted in spiking experiments using a hemocytometer. This error is common and has been reported in other CTC reports. The two different magnifications also give the same average number of cells counted per device, suggesting these are spiked cancer cells.

FIG. 15A and FIG. 15B present cancer cell capture and enumeration with optical microscopic images of 1000 SKBR3 spiked blood sample droplets on top of the device. 15 devices of spiked SKBR3 cells in blood is shown at 20× magnification. FIG. 15A shows the device imaged on the Zone 1 plane. 15 out of the 20 images analyzed to generate the data presented in Table 4 are shown here. FIG. 15B shows a plain blood sample. There are no cancer cells or WBCs observed in plain blood samples when the microscope is focused in "Zone 1" plane (first column). On the other hand when image is focused in the plane of "Zone 2" WBCs are apparent in the image (right panel). Scale bars on the first row correlate to all images in each column. Scale bars indicated in top row is the same for that column.

FIG. 15A and FIG. 15B show the reproducibility of this technique from device to device. 15 such devices are presented that were adsorbed with 1000 SKBR3 cells spiked in blood. "Zone 1" and "Zone 2" images are clearly distinguishable. Zone 1 shows the presence of spiked cancer cells in all the devices. Similarly Zone 1 imaging of plain blood, no spiked cells are seen. The WBCs are also seen in the plain blood in "Zone 2" (FIG. 15B). The images illustrate that blood does settle in all the devices in the same way and that this effect is reproducible. Table 4 presents the quantitative data from these processed images at 20× and 5× magnification respectively. The tables suggest hundreds of cells are captured in each of the devices. In Table 4, at 20× magnification anywhere from 342-1049 cells were captured in the active area suggesting a normalized capture yield of 55-100% as mentioned before. The cell count data in Table 4 indicate higher resolution and more accurate counts is possible in a small window area at the 20× magnification. The cellular diameters are also more representative.

TABLE 5

Cell Count Data per Device Based on 5 × Images for 1000 Cell Count Spiked in Blood

| Device Number | Number of Cells | Cells/mm² | Average diameter (μm) | Number of Cells per Device |
|---|---|---|---|---|
| 1 | 339 | 61 | 10 | 552 |
| 2 | 441 | 80 | 12 | 719 |
| 3 | 308 | 56 | 18 | 501 |
| 4 | 340 | 62 | 10 | 554 |
| 5 | 550 | 100 | 10 | 896 |
| 6 | 376 | 68 | 13 | 613 |
| 7 | 344 | 62 | 12 | 561 |
| 8 | 496 | 90 | 12 | 808 |
| 9 | 435 | 79 | 12 | 708 |
| 10 | 300 | 54 | 15 | 489 |
| 11 | 371 | 67 | 12 | 604 |
| 12 | 335 | 61 | 11 | 546 |
| 13 | 327 | 59 | 10 | 533 |
| 14 | 392 | 71 | 11 | 639 |
| 15 | 378 | 69 | 10 | 617 |
| Average | 382 | 69 | 12 | 623 |
| Std. Dev. | 68 | 12 | 2 | 111 |

Table 5 presents the 5× magnified cell count data. The cell count data in this table indicate one can get a more uniform distribution of the cell counts at the smaller magnification. Here, anywhere from 489-808 number of cells were captured, for a capture yield of 48.9% to 80.8%. Since the active area of 62% was only imaged, this would represent a normalized yield of 78.8% to 100%. The counts from both magnifications confirm the imaged cells are spiked breast cancer cells. Exceeding 100% is as a result of variation in spiking done manually using a hemocytometer as mentioned before. Similarly, FIG. 16A and FIG. 16B present representative images of the cell capture data for 100 SKBR3 spiked cancer cells in blood. All the regions are seen, namely CTC in "Zone 1" and WBC in "Zone 2". The spiked cancer cells were also 10 times sparser than the 1000 SKBR3 spiked blood images.

FIG. 16A and FIG. 16B present cancer cell capture with the optical images of part of the devices imaged that were adsorbed with 100 SKBR3 cells spiked blood sample at 20× magnification. 6 such devices are shown in FIG. 16A imaged in Zone 1 plane; Histogram of the number of cells counted in each device is present in bottom panel. 100% capture in 100 SKBR3 cells spiked in blood was observed. FIG. 16B shows plain blood images.

TABLE 6

Cell Count Data per Device Based on 20 × Images for 100 Cell Count Spiked in Blood

| Device Number | Number of Cells | Cells/mm² | Average diameter (μm) | Number of Cells per Device |
|---|---|---|---|---|
| 1 | 5 | 12 | 17 | 107 |
| 2 | 5 | 12 | 12 | 107 |
| 3 | 2 | 5 | 11 | 43 |
| 4 | 4 | 10 | 8 | 86 |

TABLE 6-continued

Cell Count Data per Device Based on 20 × Images for 100 Cell Count Spiked in Blood

| Device Number | Number of Cells | Cells/mm² | Average diameter (μm) | Number of Cells per Device |
|---|---|---|---|---|
| 5 | 2 | 5 | 19 | 43 |
| 6 | 3 | 7 | 9 | 64 |
| 7 | 2 | 5 | 8 | 43 |
| 8 | 2 | 5 | 16 | 43 |
| Average | 3 | 7 | 13 | 67 |
| Std. Dev. | 1 | 3 | 4 | 27 |

Table 6 presents the cell count data and the diameters of the captured cells. Anywhere between 43 cells to 107 cells were imaged and counted on the active area of the device, suggesting a normalized capture yield of 69% to 100%. While the capture yield of 100% is seen, these are on an individual device level. Summing all the cell counts for the 20 devices presented in Table 4 suggest capture of 12,478 cells out of 20,000 cell spiked in 0.1 ml of blood or 62.39% capture yield, similar to the first CTC chip. Finally, the results in Table 4, Table 5, and Table 6 show that 100% yield was achieved in both 1000 and 100 cell spiked blood at different magnifications, suggesting that the imaged cells are indeed spiked cells.

Confocal Microscopy

Figure 8A:
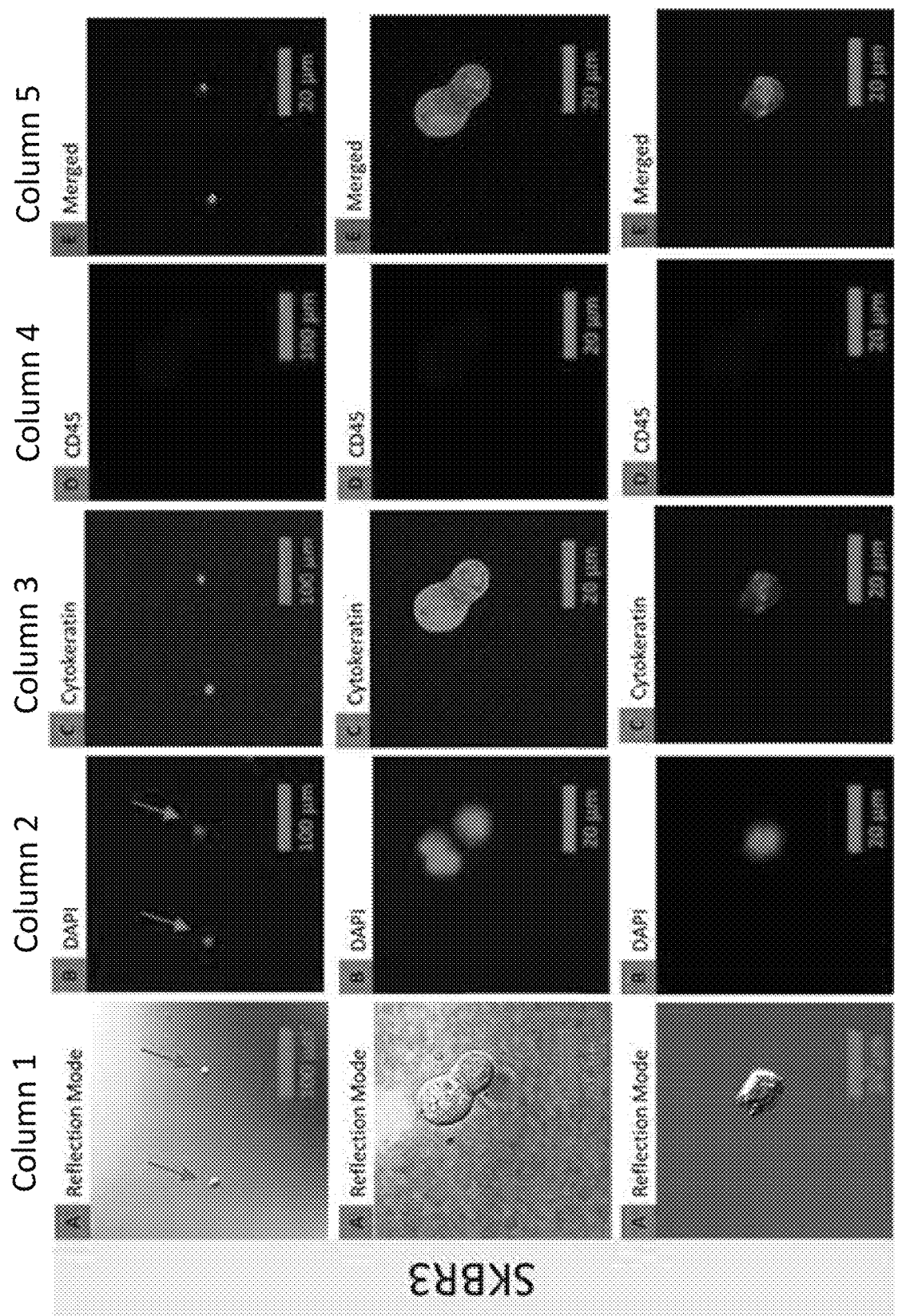
FIG. 8A and FIG. 8B present cell differentiation using Confocal Microscopy with SKBR3 cells captured on chips from 3 devices showing positive staining for DAPI, cytokeratin (CK-19) and negative for CD45 and two images of leukocytes captured showing positive for DAPI and CD45 while negative for cytokeratin. In both FIG. 8A and FIG. 8B, Column 1 shows a series of optical images; Column 2 from the left shows DAPI nuclear stain; Column 3 shows a CK19 stain for cancer cell; Column 4 shows CD45 for leukocytes and Column 5 shows a merged image of nuclear and cytoplasmic stains.
Figure 8B:
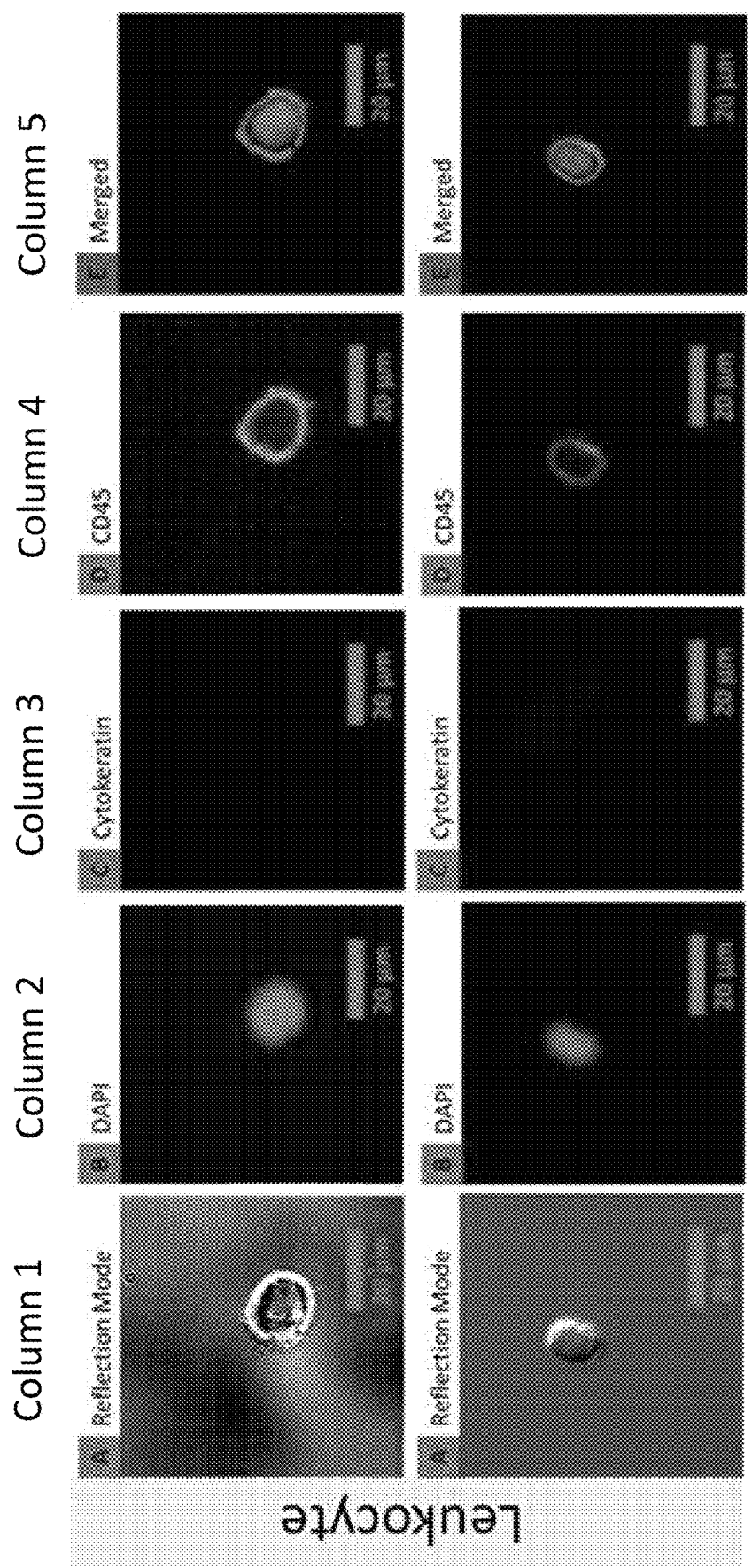

To confirm the captured cells were indeed spiked breast cancer cells, four anti-HER2 functionalized devices with adsorbed SKBR3 spiked blood that gave positive electrical signatures were further analyzed using confocal microscopy. The samples were washed three times to assess binding of cells and stained for cytokeratin, CD45 and DAPI. FIG. 8A demonstrates captured SKBR3 cells on the device stained for cytokeratin (CK-19 positive for epithelial cells and negative for hematological cells) and CD45 (negative for epithelial cells and positive for hematological cells). CTCs captured on the device were identified by staining with 4,6-diamidino-2-phenylindole (DAPI) for DNA content, and using rhodamine-conjugated anti-cytokeratin antibodies for epithelial cells, and fluorescein-conjugated anti-CD45 antibodies for hematologic cells. Cells captured by an anti-Her2 functionalized device that showed positive staining for CK-19 were identified as cancer cells, whereas CD45-positive cells were identified as leukocytes, as presented in FIG. 8B. The morphologic characteristics exhibited by the captured cells were consistent with malignant cells, including large cellular size in the merged image. Single cells could be identified in the merged image, suggesting that the nanotube-CTC chip is a viable technique for identification of CTCs from leukocytes using cytokeratin and CD45 antibodies.

Cells can also be removed from the active area of the device that gave positive electrical signatures for confocal microscopy and qPCR. Another way is to stratify all the devices that gave positive electrical signatures and remove all the cells from those devices and do confocal analysis in one step for enumeration. The ability to do staining and identify cancer cells from leukocytes shows the viability of this technology for CTC capture. Most of the leukocytes were washed away, with only one or two remaining to be imaged. These results also suggest that the leukocytes were not bound to the nanotube substrate, in line with the model proposed on differential settling of blood.

Example 2: Capture of Breast Cancer Cells Spiked in Buffy Coats

Rapid and label-free capture of breast cancer cells spiked in buffy coats using nanotube-antibody micro-arrays is described. Single wall carbon nanotube arrays were manufactured using photo-lithography, metal deposition, and etching techniques. Anti-EpCAM antibodies were functionalized to the surface of the nanotube devices using 1-pyrenebutanoic acid succinimidyl ester (PASE) functionalization method. Following functionalization, plain buffy coat and MCF7 cell spiked buffy coats were adsorbed on to the nanotube device and electrical signatures were recorded for differences in interaction between samples. A statistical classifier for the "liquid biopsy" was developed to create a predictive model based on Dynamic Time Warping (DTW) to classify device electrical signals that corresponded to plain (control) or spiked buffy coats (case). In training test, the device electrical signals originating from buffy versus spiked buffy samples were classified with ~100% sensitivity, ~91% specificity and ~96% accuracy. In the blinded test, the signals were classified with ~91% sensitivity, ~82% specificity and ~86% accuracy. A heatmap was generated to visually capture the relationship between electrical signatures and the sample condition. Confocal microscopic analysis of devices that were classified as spiked buffy coats based on their electrical signatures confirmed the presence of cancer cells, their attachment to the device and overexpression of EpCAM receptors. The cell numbers were counted to be ~1-17 cells per 5 μl per device suggesting single cell sensitivity in spiked buffy coats that is scalable to higher volumes using the micro-arrays.

The present disclosure provides devices and method for capture of breast cancer cells spiked in buffy coats using carbon nanotube micro-arrays functionalized with anti-EpCAM antibodies and their stratification based on their electrical signatures using classifier based on Dynamic Time Warping (DTW). Epithelial Cell Adhesion Molecule (EpCAM), is a mesenchymal marker that is overexpressed in all epithelial cancer cells. EpCAM is overexpressed in carcinomas and also is upregulated in metastases thereby making it a highly valuable diagnostic marker. A multiplexed micro-array of nanotube sensors functionalized with anti-EpCAM antibodies enables measurement of electrical signatures of specific and non-specific interactions as characteristic spikes in conductance versus time data. These signatures are then analyzed using Dynamic Time Warping (DTW) technique to develop heatmap with integrated dendrogram to enable classification of the electrical signatures and relate it to their sample condition (MCF7 spiked buffy or plain buffy), for the ease of reference, refers to cases and controls. The experiments demonstrated "spikes" in electrical device signatures in cell cultures and cancer cells spiked in buffy coats with natural partitioning between pain buffy and spiked buffy coats using nanotube-antibody arrays. To predict classification between cases and controls, the training set data indicated ~100% sensitivity, ~90% specificity, and ~96% accuracy in classifying devices that corresponded to un-spiked and spiked buffy coats based on their electrical signatures. A blinded test to classify case and control samples revealed ~91% sensitivity, ~90% specificity, and ~86% accuracy. Staining of captured cells on the device based on electrical signatures using confocal microscopy revealed the overexpression of EpCAM with each device capable of capturing anywhere from 1-17 cells per device suggesting single cell sensitivity. In some embodiments, the combination of multiplexed micro-arrays, sensitive nanotube elements and statistical data mining can enable devices for isolation of cells based on their mesenchymal biomarker profiles both in fine needle aspirates and for large volume samples in isolation and analysis of circulating tumor cells.

Results

FIG. 2B presents the schematic of the sensing technique. Biomolecular reactions are driven thermodynamically by the reduction in free energy of the system. For specific interactions, the reduction in free energy should be higher than non-specific interactions as presented in equation 1. Otherwise, non-specific interactions would prevail resulting in loss of cellular specificity and directionality in function. One can use a spectrum of energy domains to transduce the change in the free energy of the specific interactions into mechanics, electricity, thermal or magnetism.

$$\Delta G\text{specific} >>> \Delta G\text{non-specific} \qquad (1)$$

Since the reduction in free energy is universal for specific and non-specific pairs, this may also be true for detection of specific versus non-specific interactions in cells. Extracellular overexpressed receptors namely EpCAM interacts with their corresponding anti-EPCAM antibodies on the nanotube surface. The cooperative specific interaction of thousands of extracellular receptors with specific antibodies on nanotube surface creates spikes in the normalized electrical conductance versus time. Non-specific samples such as plain buffy coats also create such spikes in the electrical conductance versus time data with differences in their slopes. Whether such spikes in the signals could carry meaningful information about the sample condition/interaction that could be indicator of disease status is explored.

Fabrication of Nanotube Sensor Arrays.

FIG. 2A presents the wafer scale image of the 60 element array of nanotube network sensors. The sensor arrays were developed using a combination of vacuum filtration of carbon nanotube network film onto oxide coated wafers followed by multiple photo-lithography and reactive ion etching as presented in schematic (FIG. 3A-FIG. 3H). Vacuum filtration is one of the most preferred methods of making macroscopic and transparent networks of randomly oriented/highly aligned carbon nanotubes thin films and transistor devices. The film can be formed by using stock solutions of known concentrations. Vacuum filtration of SWNT suspension creates a concentration gradient due to the fluid velocity across the membrane. With appropriate bulk solution concentration and fluid velocity, one can form either isotropic or highly oriented nanotube films. While vacuum filtration has been used, in general, to make randomly oriented bucky papers, the isotropic-nematic transition of semiconducting nanotube films at ultra-low concentrations can be used. These semiconducting nanotube films are finding applications as thin-film transistors with high mobility and ON/OFF ratio's, nanotube liquid crystal elastomer based light-driven actuators and as chemical and biological sensors as presented here. Films were very low concentrations (1-4 µg) and most of the films were isotropic with the 2-4 µg samples partially transitioning into the nematic domains and also mostly single layers laying on the substrate as shown in the SEM image of FIG. 2A.

FIG. 18 presents the Raman spectroscopic micrograph of the nanotube network suggesting a very large G band (1590 cm-1), small D band (1340 cm-1) and large 2D band (2673 cm-1). This suggests very low amorphous carbon content. Further, the IG/ID ratio was measured for several networks measured IG/ID~30 suggesting a low density of defects and suitable for high-quality sensing applications. The Iso-semiconducting nanotubes had iodine as specified by the manufacturer (5% by mass using neutron activation analysis) in the form of iodixanol. This was observed in the shift in radial RBM mode $\omega r=174$ cm-1 suggesting iodine doped nanotubes due to poly iodide ions or I3- and I5-in the RBM mode at the same excitation wavelength. The iodine also decreased the tangential mode to 1590 cm-1 in these samples as compared to pristine nanotube samples (1593 cm-1) in line with past reports.

Following fabrication, the devices were investigated for their electrical resistance change with annealing. FIG. 19A presents the SEM image of the devices made from for different nanotube film concentrations. Films of three different concentrations were made, and devices were fabricated and tested for their electrical properties before and after annealing. It is observed that as the concentration increased so did the network density. At the film concentration of ~1 µg, the nanotube contacts were not established at some points, and this is reflected in their high electrical resistance. For samples with higher concentrations, 4 µg, uniform network density was observed. 4 µg films were used with more directional nanotubes with optimized electrical properties. The film electrical resistance before and after annealing was measured as presented in FIG. 19B. Annealing at 250 C decreased the resistance of the devices. It was observed that the decrease in electrical resistance of the device with annealing was directly related to the concentration of the nanotube films. Devices made with 1 µg films registered a larger decrease in electrical resistance of ~95%, compared to devices with larger film concentrations (~57% and ~47% decrease in resistance for 2 µg and 4 µg respectively). The electrical resistivity (ρ) was measured to be in the range of 50 kΩ-m for the low concentration 1 µg film to 180 Ω-m for the devices made from 4 µg film (R~106-108 Ω, 1=100 µm and W=80 µm). The large decrease in electrical resistance suggests healing and refining the nanotube network structure to enable stable electrical pathways associated with the device. FIG. 19C presents the distribution of nanotube device resistance versus number of counts for 58 devices suggesting narrow distribution of network resistance in the 106-107Ω range and quite repeatable and suitable for further sensing applications. A linear sheet conductance with nanotube film mass suggests samples above the percolation threshold.

TABLE 7

Film Resistance Summary

| CNT Film Concentration | 4 µg | 2 µg | 1 µg |
| --- | --- | --- | --- |
| Sheet Resistance Before Annealing (ohm/sq.) | 4.16E+06 | 3.30 + 07 | 5.82E+08 |
| Sheet Resistance After Annealing (ohm/sq.) | 2.25E+06 | 1.41E+07 | 2.40E+07 |
| CNT Film Resistance After Annealing (ohms) | 2.81E+06 | 1.76E+07 | 3.00E+07 |
| % Drop In Film Resistance After Annealing | 45.92% | 57.38% | 95.88% |

Table 7 presents the summary of the 4 point probe (1 mm probe spacing) measurements for the sheet resistance before and after annealing and final device resistance. In some embodiments, the devices were optimized for 4 µg nanotube films to provide stable network connectivity and stability were used for all the studies henceforth presented.

Understanding Semiconducting Nanotube Network for Chemical Sensing:

Series of experiments were conducted in Hg2+ and NH4+ ions to understand the change in electrical characteristics of the bare nanotube devices. HgCl2 in DI water was prepared to create Hg2+ ions with concentrations ranging from 30 pM to 13 μM. Similarly, NH4OH in DI water was prepared with concentrations ranging from 300 nM to 1.5 mM. FIG. 20A presents the real time monitoring of both NH4+ and Hg2+ ions with each spike is a measure of increasing concentration from 300 nm to 1.3 mM for NH4+ ions and 30 pM to 13 μM for Hg2+ ions respectively. It was found that both Hg2+ and NH4+ ions increased the conductance of the nanotube network as the concentration of ions increased. It is seen that for some intermediate concentrations, the amplitude of the spike decrease suggesting saturation of the sensor but they are also seen to recover as the amplitudes increase with time at higher concentrations. This is clearly observed in Hg2+ ion sensing. In past Hg2+ has been shown to increase the conductance of nanotube device, while NH4+ ions decreased the conductance of the device. The increase in conductance with concentration for both Hg2+ and NH4+ ion are as a result of doping. Typical electron-acceptor dopants such as I2, and Br2 are expected to transfer electrons from the carbon π states in the tubes to the dopant molecules, creating an increase in hole carriers in the SWNTs. This can increase the conductivity due to charging when positively charged molecules such as NH4+ and Hg2+ interact with the nanotube thereby increasing the current of the p-type nanotube. The shift in the RBM and G mode of the Raman spectrum presented (FIG. 18) also agrees with the presence of iodine as dopant in these nanotubes. An interesting result is that the doped nanotube devices did take the level of detection of both Hg2+ and NH4+ ions to ~30 pM and ~300 nM respectively, which is significantly higher in sensitivity compared to past reports on pristine nanotubes where the limits of detection has been shown to be ~10 nM for Hg2+. Voltage sweeps as presented in FIG. 20B shows a shift in threshold voltage towards more negative Vg suggesting p-type behavior. The real time Hg2+ and NH4+ chemical sensing therefore correlates well with the voltage sweeps. FIG. 20C presents the change in Ids vs Vg for different concentrations of Hg2+ and NH4+ ions. As the concentration increases, so does the current suggesting an increase in hole carrier density for both types of ions. A ΔG/Go vs log [A] is presented in FIG. 20D suggesting a Langmuir-adsorption isotherm with a linear response centered around [A]=1/K. The higher (ΔG/Go) for the doped nanotubes (y-axis) presented here in the Langmuir adsorption isotherm compared to past networks of mixed metallic and semiconducting nanotube also suggests the increased sensitivity of the iodine doped semiconducting nanotube sensors and lower limits of detection. The mechanism of sensing ions for both NH4+ and Hg2+ is therefore due to an increase in carrier density of iodine doped nanotubes. The same increase in conductance for the same type of charge also suggests similar mechanism and predictable sensor response of the doped nanotubes sensor devices.

Antibody Functionalization:

The prepared SWNT sensors were functionalized with anti-EpCAM antibodies through a pyrene linker molecule. The pyrene rings of the 1-pyrenebutanoic acid, succinimidyl ester (PASE) adsorb on to the sidewalls of the SWNT through π stacking and produce a stable nanotube-PASE composite. The ester on the other end of the PASE provides the attachment to the antibodies as presented in FIG. 21A schematic. Antibody conjugated gold nanoparticles (15 nm) were targeted to the PASE functionalized nanotubes and imaged in a scanning electron microscope (SEM) to assess their binding to nanotube. The antibody conjugated nanoparticles were observed to be arranged on the nanotube side wall as presented in FIG. 21B. A negative control experiment was conducted by targeting antibody conjugated gold nanoparticles to bare nanotube surface without PASE functionalization to the nanotube surface. The results in FIG. 21C conclusively suggest that antibody functionalized nanoparticles attached to the nanotube side wall by binding to PASE while no functionalization accrued between bare nanotubes and antibody conjugated nanoparticles without the presence of the PASE linker molecule. Overall the PASE conjugation provided a stable platform for all sensing in cell cultures and buffy coats.

Two other functionalization methods were also investigated, namely: (a) streptavidin-biotin conjugation chemistry and (b) Au-amine-polymer-conjugation chemistry (FIG. 28A and FIG. 28B) and compared with antibody-PASE functionalization (FIG. 21D). It was found that the antibody-PASE functionalization may be preferred with ~76 particles per μm2, followed by streptavidin-biotin conjugation chemistry of ~71 particles per μm2, followed by Au-amine-polymer functionalization of ~21 particles per μm2. Non-specific controls yielded about ~1-6 particles per μm2. Standard deviation of the particle count by each method was plotted suggesting high degree of control and reproducibility of the functionalization and attachment of antibody to the PASE molecule. The devices had channel length of 100 μm and width of 80 μm. For a 4 μg network distributed uniformly and assuming 1 antibody site per particle, this would translate into 608,000 sites for antibody binding to PASE for the entire device. Similarly, for the streptavidin-biotin chemistry, this would translate into 568,000 binding sites and for the amine-polymer-Au nanoparticle functionalization protocol, this would translate into 168,000 binding sites. For non-specific controls this would translate into 8000-48,000 binding sites. Typically, a cancer cell surface has 250,000 receptors overexpressed all over the surface compared to normal cells which has less than 10,000. With 608,000 sites, this is a ratio 2.4 antibody available per receptor for interaction.

Testing in Cell Cultures:

In these experiments several cell lines namely normal breast cell line (MCF10A), breast cancer cell lines (SKBR3, MCF7) were used. Anti-EpCAM antibodies were used as specific controls while anti-IgG antibody was used as non-specific controls. Both SKBR3 and MCF7 overexpress EpCAM while MCF10A normal cells do not. A representative micrograph of the testing protocol is presented in FIG. 29. First, a drop of 5-10 μl PBS is added to the sensor followed by a wait period of several hundred seconds, followed by a second PBS drop, followed by a wait period of several hundred seconds, followed by the addition of a spiked buffy or plain buffy coat. This ensures the sample is behaving the same way over a time period before addition of the actual sample.

Two differential signals were generated between positive and negative controls. The positive controls such as targeting EpCAM on SKBR3 (FIG. 22A) and MCF7 (FIG. 22B) produced characteristic spikes in the electrical signatures with positive slopes that stabilized after few seconds. It was also noted that the stabilized conductance levels even after 60 seconds were higher than initial value before the sample addition suggesting an irreversible change in the electrical signature or forward reaction kinetics for the formation of the antibody-receptor complex. Similarly, the negative controls namely targeting EpCAM in MCF10A (FIG. 23A) and targeting IgG in all the cells (FIG. 23B) and even PBS produced similar spikes with negative slopes and stabilized after several seconds. It was also noted that the final conductance after cell addition was higher than the initial conductance value and stabilized at that value. In determining the statistical significance, the average slope of ~0.5 seconds following the inflection point was calculated for each signal. Both data sets were determined to be random and of equal variance. A final p value of 0.0011<0.05 was calculated showing a statistically significant difference between all positive and negative controls as presented in Table 8.

TABLE 8

Statistical Comparison Between Specific and Control Signals in Cell Cultures

|  | Specific | | Non-specific | |
| --- | --- | --- | --- | --- |
|  | G1: EpCAM-SKBR3 | G2: EpCAM-MCF7 | G3: EpCAM-MCF10A | G4: Igg-(SKBR3, MCF7, MCF10A) |
| Calculated Slopes After Sample Droplet Addition | 0.0249 0.1205 0.0414 | 0.0498 0.0296 0.0943 | −0.0471 −0.0279 −0.0258 | −0.1761 −0.0432 −0.1197 |
| Average | 0.0623 | 0.0579 | −0.0336 | −0.1130 |
| Std. Deviation | 0.0417 | 0.0270 | 0.0095 | 0.0544 |
| P Value | G1 vs. G2: | | 0.9072 | |
|  | G1 vs. G3: | | 0.0340 | |
|  | G1 vs. G4: | | 0.0225 | |
|  | G2 vs. G3: | | 0.0107 | |
|  | G2 vs. G4: | | 0.0164 | |
|  | G3 vs. G4: | | 0.1120 | |
| Final P Value | Specific vs. Non-specific | | 0.0011 | |

It should be noted that the positive controls consisted of two different cell lines MCF7 and SKBR3 targeted for EpCAM mentioned as G1 and G2 respectively in Table 8. Similarly the negative control consisted of EpCAM-MCF10A, and IgG-(MCF7, MCF10A, SKBR3) mentioned as G3 and G4. The p values in the Table 8 suggest that there is a significant statistical difference between specific and non-specific electrical signatures. It is also observed that within the same group, the p values do not reflect a significant difference suggesting natural partitioning of specific and non-specific signals. This suggests that the nanotube sensor is capable of differentiating between two different cell populations which are similar except for their surface markers. The similar results over wide ranging cell lines and antibodies suggest specific interactions gave rise to characteristic spikes in electrical signatures due to their cooperative binding of antibodies to their receptors.

Testing in Buffy Coats and Development of a Statistical Classifier for Liquid Biopsy:

ANOVA balanced design was used to reduce any systematic variability. Factors in ANOVA design includes medium (Bare, Igg EpCAM) and three types of samples (PBS: control, Buffy: control 2 and Spiked Buffy: case) with fixed number of replicates. Dynamic Time Warping (DTW) was used for classification.

To demonstrate the ability of the devices to discriminate between buffy and spiked buffy signals, a training-test approach was used to building a k-nearest neighbor classifier using DTW. To evaluate if devices could differentiate between MCF7 positive samples and MCF7 negative samples, both were tested utilizing the devices. The negative samples consisted of a buffy coat sample from the biorepository without the presence of breast cancer cells. The positive samples consisted of the same buffy coat sample that was spiked with MCF7 breast cancer cells (10,000/µl) as a proof of concept. The drain current from the nanotube devices was recorded continuously throughout each experiment. A representative figure of the testing protocol is presented in FIG. 29. The resulting data consisted of time series with characteristic "spikes" occurring after the application of the sample as shown in FIG. 24A-24B for the training set.

Construction of the Classifier:

A set of training signals from the devices was used for selecting the tuning parameters for the classifier. An independent set of mixed signals was then classified using the classifier. Sensitivity, specificity, and the misclassification rate of the classifier on the test set were then used to evaluate performance.

To describe the construction of the classifier, the following notation can be used. A device signal is represented as a time series, $y=\{y_t, t \in T\}$ where T is a finite set that indexes time. To indicate that the signal is the ith replicate from the jth group (Buffy vs. Spiked buffy) the notation $y_{i,j}$ was used. Before a classifier could be constructed, the raw signals were processed so that the signals had comparable a sampling rate, length, and intensity. The signals $y_{i,j}$ were first averaged so that each signal had the same sampling rate of one sample per second. The signal was then truncated by removing series values between the first value and five seconds after signal most extreme peak—resulting in a new $t_0$ for each signal. Experimental variation in the timing of the replicate drops contacting the device resulted in non-uniform length time indices. For length standardization, the signals were then truncated at 253 seconds. The final processing step was mean and variance standardization so that each signal had mean 0 and variance 1.

To compare signals and develop a classifier, a measure of signal similarity is needed. The technique employed to develop a similarity measure in this analysis is known as Dynamic Time Warping (DTW).

DTW is a method of aligning two-time series so that a traditional distance metric (such as the Euclidean metric) can be used as a measure of similarity. To measure the similarity between two signals $y_1$ and $y_2$, two matrices $\Delta \in \mathbb{R}^{m \times n}$ and $\Gamma \in \mathbb{R}^{(m+1) \times (n+1)}$ were computed. The first matrix $\Delta$ has entries representing the pairwise distances between points in the series, that is:

$$\delta(t,t')=d(y_{1,t},y_{2,t'})$$

where d is a distance metric. For this analysis the Euclidean distance metric was used. Once this distance matrix was defined, the elements of $\Gamma$ were determined using a recurrence relation that weights steps through a cumulative distance matrix. Two formulations for this matrix were considered using the following recursions:

$$\gamma_1(i,j)=\min\{\delta(i,j)+\gamma_1(i-1,j),\delta(i,j)+\gamma_1(i-1,j-1),\delta(i,j)+\gamma_1(i,j-1)\},$$

$$\gamma_2(i,j)=\min\{\delta(i,j)+\gamma_2(i-1,j),2\times\delta(i,j)+\gamma_2(i-1,j-1),\delta(i,j)+\gamma_2(i,j-1)\}.$$

Once the cumulative distance matrix $\Gamma$ has been defined, a warping curve was sought that aligns the time indices for each time series:

$$\phi(k)=(\phi_s(k),\phi_s'(k)), k \in \{1, \ldots, K\}, \phi(k) \in \{1, \ldots, m\} \times \{1, \ldots, n\}.$$

This warping curve was chosen such that once $y_1$ and $y_2$ are aligned, the cumulative distance between the series is minimized. To find such a curve, the lowest scoring path through the cumulative distance matrix $\Gamma$ was found subject to the following constraints:

$$\phi(1)=(1,1)$$

$$\phi(T)=(m,n)$$

$$(\phi(k)-\phi(k-1)) \in \{(1,1),(1,0),(0,1)\} \forall k>1.$$

Constraint (1) and (2) ensure that the beginning and the end of the signals $y_1$ and $y_2$ are aligned. Constraint (3) ensures uniform length of step sizes and that the warping curve is monotonic increasing. An illustration of the alignment process for a pair of qualitatively similar and qualitatively different signals are presented (FIG. 30A-FIG. 30D and FIG. 31A-FIG. 31D) respectively. Once a warping path has been defined, the Dynamic Time Warping distance between two signals (not a formal distance metric) is given by:

$$d_{DTW}(y_1,y_2) = \Sigma_{k=1}^{T} \Delta(\phi(k)).$$

For each step pattern, a dissimilarity matrix using DTW distance as the dissimilarity measure was constructed for the signals using the DTW package in R.

A training-test approach was used to develop a k nearest neighbor (k-nn) classifier from the DTW distance dissimilarity matrices. The training set consisted of 10 Buffy signals and 28 Spiked Buffy signals. 10-fold cross-validation was employed using 10,000 bootstrapped samples from the training set to determine which step pattern (symmetric 1 vs symmetric 2) and a number of nearest neighbors yielded the lowest misclassification rate (FIG. 32). The misclassification rate is defined as:

$$\text{Err} = \Sigma_{i=1}^{N}(Y_i \neq \hat{Y}_i)$$

where $Y_i$ denotes the true class of the signal $y_i$ and $\hat{y}_1$ denotes the k-nn classifier predicted class the for $y_i$.

Once the optimal step pattern and classifier design had been selected, the classifier was evaluated on the 22 signals of the test set. The study personnel who conducted the classification on this test set were blinded to the true class (Buffy vs Spiked Buffy) of the signals.

Training Set Classification

A training validation test set approach was used to construct DTW distance based probabilistic modeling of surrounding observations (such as κth-nearest neighbors). The training data consisted of plain PBS (FIG. 23A as a reference, 10 buffy coat samples and 17 spiked buffy coat samples as presented in FIG. 23B and FIG. 23C. A κ-fold cross-validation parameter selection was conducted using 10-fold cross validation on 10,000 bootstrapped samples from the training set of 27 signals for which the class (buffy vs. spiked buffy) was known. The tuning parameters selected were those that minimized the mean and variance of the misclassification rate. The test set misclassification rate, classifier sensitivity, and classifier specificity were then used as criteria to measure the success of the devices in discriminating between positive and negative samples.

TABLE 9

Training Classification of Biosensor Signals Based on Dynamic Time Warping (DTW)

| | | Condition Training | | |
|---|---|---|---|---|
| | | Condition Positive | Condition Negative | |
| Test Outcome | Test Outcome Positive | True Positive = 17 | False Positive = 1 (Type I Error) | PPV = 94% |
| | Test Outcome Negative | False Negative = 0 (Type II Error) | True Negative = 9 | NPV = 100% |
| | | Sensitivity = 100% | Specificity = 90% | Accuracy = 96.3% |

The statistical table for training set is presented in Table 9. A positive predictor value (PPV)=94% and negative predictor value (NPV)=100% with accuracy=96.3% was obtained for training set. One data was misclassified and was false positive or type I error. No false negatives were observed in training set.

Blinded Test Classification

FIG. 24A and FIG. 24B present the electrical signals for the blind test. Based on the training set, the tuning parameters were selected, 22 test signals (of class unknown to the personnel constructing the classifier) were classified using the training signals as reference signals.

TABLE 10

Blinded Set Classification of Biosensor Signals Based on Dynamic Time Warping (DTW)

| | | Blind Test | | |
|---|---|---|---|---|
| | | Condition Positive | Condition Negative | |
| Test Outcome Positive | | True Positive = 10 | False Positive = 2 (Type I Error) | PPV = 83% |
| Test Outcome Negative | | False Negative = 1 (Type II Error) | True Negative = 9 | NPV = 90% |
| | | Sensitivity = 91% | Specificity = 90% | Accuracy = 86% |

Table 10 presents the corresponding classification table for the blind test. A PPV=83%, NPV=90% and accuracy=86% was observed. A misclassification rate of ~14% was observed in these blind testing. 3 samples over 22 samples were misclassified. Two samples that were misclassified were false positive or type I error and one sample that was misclassified was false negative or type II error. This suggests the classifier is capable of differentiating electrical signals between samples that were plain buffy coat or buffy coat with cancer cells which is the first accomplishment for any nanotube biosensor device.

Heatmap

FIG. 25 is the heat map of the between signal DTW distances for the signals used in the k-fold cross-validation tuning parameter selection and as reference signals for the classifier. 10-fold cross-validation on the bootstrap samples resulted in a final DTW distance based κ-nn classifier utilizing a symmetric 2 step pattern and 3 nearest neighbors. In the margins of this figure a dendrogram of the complete-linkage agglomerative hierarchical clustering of the same is shown. This demonstrates that on the training data, DTW distance as a dissimilarity measure, naturally partitions the sample data into two distinct clusters (with one misclassification) according to sample class. The statistical classifier naturally partitions the buffy versus spiked buffy coats suggesting specific interactions are quite unique in their electrical signatures compared to non-specific interactions and establishes a relationship between electrical conductance data with biological and possibly proteomic features (presence or absence of cancer cells in buffy coats versus presence or absence of mesenchymal marker EpCAM).

Cell Capture with Single Cell Sensitivity and Confocal Microscopy:

The devices that gave positive signatures were then further processed to assess the ability to capture spiked MCF7 cells from buffy coats. FIG. 26A and FIG. 26B are the images from 22 processed samples from the blind test with both buffy and spiked buffy coats. Each image was taken of the device immediately after taking the electrical signature measurement.

TABLE 11

Captured Cells on Each Device for Both Case and Controls Using Optical Microscope

| Device No. | Spiked (+) | Spiked (−) | Number of Cells |
|---|---|---|---|
| 1 | ✓ |  | 25 |
| 2 | ✓ |  | 22 |
| 3 | ✓ |  | 3 |
| 4 | ✓ |  | 14 |
| 5 | ✓ |  | 6 |
| 6 | ✓ |  | 9 |
| 7 | ✓ |  | 6 |
| 8 | ✓ |  | 19 |
| 9 | ✓ |  | 4 |
| 10 | ✓ |  | 19 |
| 11 |  | X | 0 |
| 12 |  | X | 0 |
| 13 |  | X | 1 |
| 14 |  | X | 0 |
| 15 |  | X | 0 |
| 16 |  | X | 1 |
| 17 |  | X | 0 |
| 18 |  | X | 0 |
| 19 |  | X | 2 |
| 20 |  | X | 2 |

For easier presentation, the spiked buffy coats are presented in FIG. 26A, the plain buffy coats are presented in FIG. 26B and Table 11 consisting of number of cells captured on the device in FIG. 26A and FIG. 26B. The cells could be counted after imaging in a Nikon Eclipse optical microscope in the buffy coat using imaging software. The images show the ability to capture 1 to 20 cells per device and their positive/negative electrical signatures assessed from the classifier. Buffy coat was mainly proteins and denatured hematologic cells, so the MCF7 cells were identified which were quite distinct as these were spiked cells. The single cells captured in the plain buffy coat are believed to be one or two hematologic or white blood cells that were bound to the device.

Six devices were removed and also imaged using confocal microscopy as presented in FIG. 27 (only 4 shown). The samples were washed three times to assess binding and stained for DAPI and EpCAM. A cover slip was placed on the device and imaged using confocal microscope. The images from devices as presented suggest single cell sensitivity as well as positive for EpCAM overexpression. The results suggest that the samples were bound to the nanotube device through cooperative binding of the receptors to the antibodies. Again, anywhere ~1-17 cells were observed in line with optical microscopy observations.

Methods:

CNT-Network Formation:

The first step in the process was assembling the nanotube network. A 9-9% weight, IsoNanotubes-Semiconducting single wall carbon nanotube mixture was purchased from NanoIntegris LLC. The diameter of the nanotubes was between 1.2-1.7 nm diameter and 300 nm to 5 μm in length. Nanotubes were suspended in surfactant solution at one mg/100 mL when received. 100, 150, 200, and 400 μL of the stock solution. 1, 1.5, 2, and 4 μg of CNT, were separately aspirated and then diluted in 85 mL of DI water and 15 mL of 1% w/v sodium dodecyl Sulfate (Sigma-Aldrich, Cat. No. 436143), for a final concentration of 1, 1.5, 2, and 4 μg/100 mL.

Vacuum Filtration

The 100 mL solutions each were vacuum filtered over a cellulose membrane, 0.05 μm pore size (Millipore, No. VMWP09025). Four CNT film networks were generated at four different concentrations. The vacuum filtration method self-regulates the deposition rate of nanotubes on the membrane to produce an evenly distributed conductive network. The CNT film network was then pressed onto a dry oxidized (300 nm thickness) 4" silicon wafer for 30 minutes. Next the wafer was transferred to an acetone vapor bath that dissolved the overlaying filter membrane.

Clean Room Processing

Patterning of the nanotube film and electrode and insulating layer fabrication were done by photolithography in the cleanroom. The S1813 photoresist was used to mask the nanotube film areas needed for the sensor elements. Exposed nanotubes were etched away in a March Reactive Ion Etcher (RIE) for 90 s at 200 W power and 10% O2. The S1813 photoresist was also used to mask the electrode pattern. Electrodes, 15 nm Ni and a 90 nm Au layers, were deposited by sputtering in a Leskar PVD 75 system, 300 W DC power. Lift-off process was conducted in an acetone bath to remove the excess Ni/Au layers. Lastly, the sensors were covered with SU8-2005, a 5 μm thick photopolymer layer. A window over each of the nanotube sensor elements was developed, but the electrodes remain insulated beneath the SU8.

Raman Spectroscopy

Raman analysis was done at an excitation wavelength of ~532 nm using a XploRA Raman spectrometer (Horiba Scientific). The laser beam is focused onto the surface of the CNT film on top of a Si wafer substrate through a 50× objective lens. This measurement was repeated six times at different locations of the sample. The RBM (172 cm-1), Si (518 cm-1), D (1340 cm-1), G (1590 cm-1), and 2D (2673 cm-1) peaks were identified throughout the sample.

Device Functionalization

Finished carbon nanotube sensors were functionalized with anti-EpCAM by a pyrene linker molecule. The pyrene rings of 1-Pyrenebutanoic acid, succinimidyl ester (PASE AnaSpec #81238) adsorb onto carbon nanotube sidewalls by it-stacking. The ester on the other end of the molecule provided an attachment point for antibodies. PASE (AnaSpec, Cat. No. 81238) were dissolved in methanol at one mM. Devices were incubated in the PASE solution for 2 hours at room temperature, and then rinsed with methanol and then DI water. Devices were then incubated in Anti-EpCAM (EMD Bioscience, Cat. No. OP187) or anti-IgG (EMD Millipore, Cat. No. 411550), 20 μg/mL in 1× Phosphate-buffered saline (PBS), for 2 hours at room temperature. After incubation, devices were rinsed in DI water 3×. Tween20 was used to block unfunctionalized nanotube sidewalls to minimize non-specific interactions. Devices were incubated with 0.5% Tween20 for 2 hours at room temperature. After incubation, devices were washed with water, then incubated in 5 µl droplets of PBS overnight in a humid chamber at 4° C. before testing.

Hg2+ and NH4+ Ion Experimentation

HgCl2 (Sigma-Aldrich, Cat. No. 215465) in DI water was prepared to create Hg2+ ions with concentrations ranging from 30 pM to 13 µM. Similarly, NH40H (Sigma-Aldrich, Cat. No. 338818) in DI water was prepared with concentrations ranging from 300 nM to 1.5 mM. Array of un-functionalized bare devices were prepared with initial 5 µL droplet of DI water suspended on top. 100 mV source drain bias and 0V gate voltage applied by reference Ag/AgCl electrode. Device current was monitored as ion concentrations were increased on the devices every 180 second. In addition voltage-sweep readings were taken after addition of each ion concentration.

Cell Culture and Preparation

The breast adenocarcinoma cell line, MCF7, MCF10 A and SKBR3 (ATCC, Cat. No. HTB-22; CRL-10317; HTB-30), was cultured under conditions as recommended by the supplier. MCF10 A is non-tumorigenic cells that are EpCAM negative and MCF7 and SKBR3 are EpCAM positive cell lines. Cells were grown for 3-4 days to reach ~80% confluence. The cells were then detached using Accutase solution (Sigma, Cat. No. A6964), centrifuged and resuspended in 1×PBS at 20,000 cells/µL. This solution was used to spike the healthy buffy coat sample (James Graham Brown Cancer Center, Study No. C020-01) at 1:1 ratio for a final MCF7 concentration of 10,000 cells/µL.

Confocal Microscopy:

After experimental data had been collected, the devices were saved and taken for staining and confocal imaging. The devices were first rinsed with PBS to remove excess cells and buffy coat fragments and then incubated with 4% paraformaldehyde (Santa Cruz Biotechnology Inc., Cat. No. sc-281692). After initial preparation device were stained with anti-EpCAM (EMD Bioscience, Cat. No. OP187) primary antibody, anti-mouse IgG-TR (Santa Cruz Biotechnology Inc., Cat. No. sc-2781) Texas Red conjugated secondary antibody, and DAPI (Molecular Probes, Cat. No. D1306) according to the standard confocal staining protocol. A coverslip was placed on top of each device and sealed before imaging. Confocal laser scanning microscopy images were obtained on a Nikon Eclipse T. with coverslip corrected objective focused at 600×.

Gold Nanoparticle Functionalization

Similar to device functionalization process, devices were prepared and functionalized. Instead of using anti-EpCAM, an antibody conjugated gold NPs (Nanopartz, Cat. No. C11-15-TX-50) were used to functionalize with the PASE linker molecule. The NPs were diluted 1:250 in 1×PBS and incubated on top of the device for 2 hours. Finally, devices were rinsed with water 3× and samples were taken to scanning electron microscopy (SEM) for imaging.

Device Testing

The testing platform was set up on Signatone probe station. Agilent 4156C Semiconductor Parameter Analyzer equipped with a custom LabVIEW interface was used for monitoring the sensors and data collection. 100 mV bias was applied and the source-drain current, ISD, was recorded for the duration of the test. The accuracy of the semiconductor parameter analyzer is 1 fA. The entire probe station assembly is placed on an optical table that is vibration isolated using air on all four legs. A metal box covers the entire assembly to avoid electromagnetic interference. The probes are connected to the parameter analyzer using a triaxial cable that is EM shielded. Throughout the testing the devices were maintained inside a humidified chamber to prevent evaporation of the sample droplet. The testing protocol started with a hydrated device, and a 5 µL droplet of 1×PBS, which was placed immediately after functionalization and left overnight. The bias was applied, and the sensor was monitored for the initial 3 minutes, then 5 µL droplets of the sample solution, 1×PBS or buffy coat suspension, was pipetted directly into the standing 5 µL droplets. Devices were monitored for 360 seconds after each addition of a new sample solution. The total duration of one test varied from 540 to 1980 seconds. To compare results among devices, ISD data were normalized to obtain the G/G0 values for conductance. The sensor element was also imaged on an optical microscope to confirm the presence of cancer cells. The spiked buffy coat samples consisted of ~10,000 MCF7 cells/L for these demonstrations. Such concentration was chosen to cover consistently the active sensor element surface with 0-30 cells at the sensor window for assessing cell capture per device.

Statistical Classifier:

Statistical classification was done using DTW package in R. The sensitivity, specificity, and misclassification rate were then computed, considering Spiked Buffy to be a positive test and Buffy to be a negative test. Sensitivity is defined as TP/P, where TP denotes the number of positive test outcomes, and P denotes the number of true positives. Specificity is defined as TN/N, where TN denotes the number of negative test outcomes, and N denotes the number of true negatives.

All patents, patent applications, and published references cited herein are hereby incorporated by reference in their entirety. It should be emphasized that the above-described embodiments of the present disclosure are merely possible examples of implementations, merely set forth for a clear understanding of the principles of the disclosure. Many variations and modifications may be made to the above-described embodiment(s) without departing substantially from the spirit and principles of the disclosure. It can be appreciated that several of the above-disclosed and other features and functions, or alternatives thereof, may be desirably combined into many other different systems or applications. All such modifications and variations are intended to be included herein within the scope of this disclosure, as fall within the scope of the appended claims.

What is claimed is:

1. A method for counting cells in a blood sample comprising:
    applying a blood sample onto a carbon nanotubes (CNT) device, wherein the blood sample comprises cells of pre-selected type and cells of non-pre-selected type;
    allowing the cells in the blood sample to settle on the CNT device, and
    detecting an electrical signal from the CNT device, wherein the electrical signal is indicative of a capture of the cells of pre-selected type or the cells of non-pre-selected type by the CNT device;
    analyzing the detected electrical signal to identify whether the cells of pre-selected type or the cells of non-pre-selected type are captured by the CNT device from the blood sample by distinguishing the electrical signal due to specific interactions from an electrical signal due to non-specific interactions, wherein the specific interactions are between the cells of pre-selected type and the CNT device and the non-specific interactions are between the cells of non-pre-selected type and the CNT device; and only upon the identification of the capture of the cells of pre-selected type, counting the captured cells of the pre-selected type in the blood sample.

2. The method of claim 1 wherein the cells of pre-selected type are breast cancer cells.

3. The method of claim 1 wherein the CNT device comprises:
a substrate;
a thin film of carbon nanotubes (CNTs) disposed on the substrate; the CNTS being functionalized with one or more antibodies capable of binding to the cell of pre-selected type to be captured; and
a plurality of conductive contacts disposed on the substrate and electrically coupled to the thin film, wherein the plurality of conductive contacts are configured to detect the capture of the cells of pre-selected type by the one or more antibodies.

4. The method of claim 3 wherein the film is formed from a single layer of carbon nanotubes.

5. The method of claim 3 wherein the one or more antibodies include with EpCAM and anti-Her2.

6. The method of claim 3 wherein the film includes a passivation layer so only the functionalized carbon nanotubes are exposed to the blood sample.

7. The method of claim 3 wherein the film has a density may be between 3 and 5 nanotubes per micrometer.

8. The method of claim 3 wherein the film is functionalized with 1-Pyrenebutanoic Acid Succinimidyl Ester (PASE) to conjugate one or more antibodies to the film.

9. A method for counting cells in a blood sample comprising:
applying a blood sample onto a carbon nanotubes (CNT) film functionalized with one or more capture agents, wherein the blood sample comprises cells of pre-selected type and cells of non-pre-selected type;
allowing cells in the blood sample to react with the one or more capture agents of the CNT film, and
receiving, from one or more electrical contacts in electrical connection with the CNT film, an electrical signal due to interaction between the one or more capture agents or the CNT film with the cell of preselected type or the cells of non-pre-selected type;
analyzing the electrical signal to identify whether the cells of pre-selected type in the blood sample are interacting with the one or more capture agents or the CNT film by distinguishing an electrical signal due to specific interactions from an electrical signal due to non-specific interactions, wherein the specific interactions are between the cells of pre-selected type and the capture agents and the non-specific interactions are between the cells of the non-pre-selected type and the capture agents or the CNT film; and
only upon the identification of the interaction by the cells of pre-selected type counting the captured cells of pre-selected type in the blood sample.

10. The method of claim 9 wherein the cells of pre-selected type are cancer cells and the cells of non-pre-selected type are blood cells.

11. The method of claim 9 wherein the one or more capture agents is selected from a group consisting of anti-epithelial-cell-adhesion-molecule (EpCAM), anti-human epithelial growth factor receptor 2 (anti-Her2), nonspecific immunoglobin (IgG) antibodies, PSMA, EGFR, her2-neu, her1, her3, G-protein coupled receptors and combinations thereof.

12. A method for counting cells in a blood sample comprising:
applying a blood sample onto an array comprising one or more carbon nanotubes (CNT) devices, wherein the blood sample comprises cells of pre-selected type and cells of non-pre-selected type, wherein each of the one or more CNT devices comprises;
a substrate;
a CNT film disposed on the substrate, the CNT film being functionalized with one or more capture agents capable of capturing the cell of pre-selected type; and
one or more conductive contacts disposed on the substrate and electrically coupled to the CNT film, wherein the plurality of conductive contacts are configured to detect a capture of the cells of pre-selected type by the one or more capture agents;
allowing cells in the blood sample to settle on the CNT film,
receiving, from one or more electrical contacts in electrical connection with the CNT film, an electrical signal due to interaction between the one or more capture agents or the CNT film with the cell of preselected type or the cells of non-pre-selected type;
analyzing the electrical signal to identify whether the cells of pre-selected type in the blood sample are interacting with the one or more capture agents or the CNT film by distinguishing an electrical signal due to specific interactions from an electrical signal due to non-specific interactions, wherein the specific interactions are between the cells of pre-selected type and the capture agents and the non-specific interactions are between the cells of the non-pre-selected type and the capture agents or the CNT film; and
only upon the identification of the interaction by the cells of pre-selected type counting the captured cells of pre-selected type in the blood sample.

13. The method of claim 12 wherein the cells of pre-selected type are cancer cells and the cells of non-pre-selected type are blood cells.

14. The method of claim 12 wherein the one or more capture agents is selected from a group consisting of anti-epithelial-cell-adhesion-molecule (EpCAM), anti-human epithelial growth factor receptor 2 (anti-Her2), nonspecific immunoglobin (IgG) antibodies, PSMA, EGFR, her2-neu, her1, her3, G-protein coupled receptors and combinations thereof.

* * * * *